United States Patent
Chow et al.

(10) Patent No.: US 9,259,390 B2
(45) Date of Patent: *Feb. 16, 2016

(54) PARENTERAL AND ORAL FORMULATIONS OF BENZIMIDAZOLES

(75) Inventors: Diana Shu-Lian Chow, Houston, TX (US); Pranav Gupta, Short Hills, NJ (US); Yulan Qi, Houston, TX (US); Dong Liang, Pearland, TX (US)

(73) Assignee: The University of Houston System, Houston, TX (US)

( * ) Notice: Subject to any disclaimer, the term of this patent is extended or adjusted under 35 U.S.C. 154(b) by 1075 days.

This patent is subject to a terminal disclaimer.

(21) Appl. No.: 12/220,374

(22) Filed: Jul. 24, 2008

(65) Prior Publication Data

US 2009/0048322 A1    Feb. 19, 2009

Related U.S. Application Data

(63) Continuation-in-part of application No. 10/640,467, filed on Aug. 13, 2003, now Pat. No. 7,419,996.

(51) Int. Cl.
*A61K 31/4184* (2006.01)
*A61K 9/107* (2006.01)
*A61K 9/00* (2006.01)

(52) U.S. Cl.
CPC ............ *A61K 9/1075* (2013.01); *A61K 9/0019* (2013.01); *A61K 31/4184* (2013.01); *A61K 9/0095* (2013.01)

(58) Field of Classification Search
CPC ............ A61K 9/0019; A61K 31/4184; A61K 9/1075; A61K 9/0095
See application file for complete search history.

(56) References Cited

U.S. PATENT DOCUMENTS

| | | | | |
|---|---|---|---|---|
| 5,169,846 A | * | 12/1992 | Crooks | 514/224.8 |
| 5,444,041 A | * | 8/1995 | Owen et al. | 514/6.5 |
| 5,840,737 A | * | 11/1998 | Phillips | 514/338 |
| 5,925,374 A | * | 7/1999 | McLaren et al. | 424/449 |
| 6,054,136 A | * | 4/2000 | Farah et al. | 424/400 |
| 6,316,497 B1 | * | 11/2001 | Liu et al. | 514/475 |
| 2003/0082215 A1 | * | 5/2003 | Lemut et al. | 424/400 |

* cited by examiner

*Primary Examiner* — Robert A Wax
*Assistant Examiner* — William Craigo
(74) *Attorney, Agent, or Firm* — Benjamin Aaron Adler

(57) ABSTRACT

Provided herein are drug delivery systems, such as self-nanoemulsifying drug delivery systems, self-emulsifying drug delivery systems and parenteral microemulsion formulations, suitable for parenteral or oral delivery to a subject. The drug delivery systems may comprise a benzimidazole derivative, e.g., mebendazole, an oil, a surfactant, a cosurfactant and a dipolar aprotic solvent in a microemulsion formulation. Also provided are methods for improving the bioavailability of a benzimidazole derivative during treatment of a pathophysiological condition by using a formulation combining a particular emulsion droplet diameter and ratio of the surfactant: cosurfactant therein, for increasing concentration and retention of a benzimidazole derivative in the lung via a parenterally administerable microemulsion with droplet size of about 35 nm to less than 100 nm and for defining hemolytically safe microemulsions of a benzimidazole derivative during a therapeutic treatment via a parenterally administerable microemulsion with a surfactant:cosurfactant content by weight of about 6% to 48%.

17 Claims, 29 Drawing Sheets

MZ (0.1 µg/mL, 100 µL = 10 ng)

Conditions:

Stationary Phase - $C_{18}$ Column, 300 x 3.9 mm (Waters Corporation)

Mobile Phase – Acetonitrile/0.05 M $KH_2PO_4$ (40:60 V/V; pH = 6.5)

Flow rate – 1.2 ml/min

Detection – UV at 254 nm

Integration – Milton Ray CI-4100 integrator

Linear range – 0.05 – 0.5 µg/mL

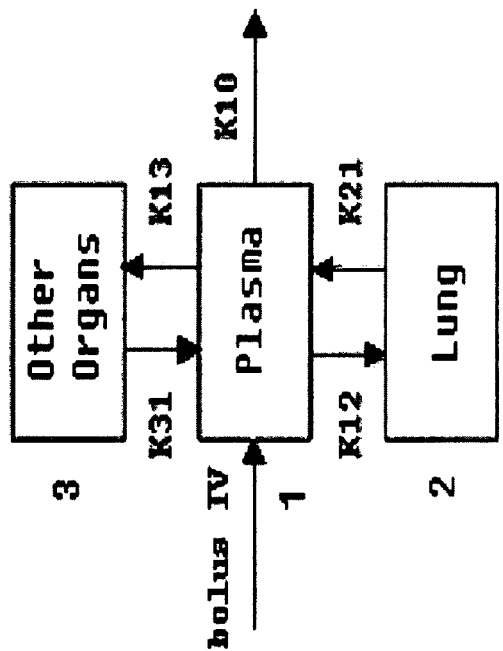

Compartments: 1–The Central Compartment
2–The First Peripheral Compartment
3–The Second Peripheral Compartment Microconstants: $k_{10}$–Elimination Rate Constant from Central Compartment
$k_{12}$–The First-Order Rate Microconstant from the Central Compartment to the First Peripheral Compartment
$k_{21}$–The First-Order Rate Microconstant from the First Peripheral Compartment to the Central Compartment
$k_{13}$–The First-Order Rate Microconstant from the Central Compartment to the Second Peripheral Compartment
$k_{31}$–The First-Order Rate Microconstant from the Second Peripheral Compartment to the Central Compartment

Fig. 16

PARENTERAL AND ORAL FORMULATIONS OF BENZIMIDAZOLES

CROSS-REFERENCE TO RELATED APPLICATION

This is a continuation-in-part of nonprovisional application U.S. Ser. No. 10/640,467, filed Aug. 13, 2003 now U.S. Pat. No. 7,419,996.

BACKGROUND OF THE INVENTION

1. Field of the Invention

The present invention relates generally to the fields of pharmacology and pharmaceutics. More particularly, it concerns pharmaceutical compositions that include a benzimidazole, a polyol, and a dipolar aprotic solvent. It also concerns pharmaceutical compositions that include a benzimidazole, an oil, a dipolar aproptic solvent, and a surfactant.

2. Description of the Related Art

The identification of improved methods of drug delivery is crucial in the treatment of a vast number of human diseases. In particular, even though scientific studies might have identified the potential usefulness of a certain drug in the treatment of a particular condition, treatment options may be limited if proper formulations of the drug to facilitate delivery of the agent to the diseased tissue are not identified.

One disease wherein pharmaceutics has played a significant role is cancer. Cancer is the second leading cause of death in the United States. Half of all men and one-third of all women in the United States will develop cancer during their lifetimes. Today, millions of people are living with cancer or have had cancer. The sooner a cancer is identified and treatment initiated, the greater are the chances for survival.

Pharmaceutical preparations that are effective against cancer comprise an emerging and expanding area of research and potential commercial development. Pharmaceutical agents are being developed that can delay or arrest development of cancer, and the development of precancerous lesions into cancers. Precancerous lesions include, for example, lesions of the breast that can develop into breast cancer, lesions of the skin that can develop into malignant melanoma or basal cell carcinoma, colonic adenomatous polyps that can develop into colon cancer, cervical dysplasia that can develop into cervical cancer, premalignant lesions of the oropharynx that can develop into head and neck cancer.

The search for drugs useful for treating and preventing neoplasias in their earliest stages is intensive because chemotherapy and surgery alone are often ineffective, and current cancer chemotherapy has severe side effects. Such preventive treatment is also potentially useful for recovered cancer patients who retain a risk of cancer recurrence, and even for cancer patients who would benefit from compounds that selectively induce apoptosis in neoplastic, but substantially not in normal cells.

Induction of apoptosis is one mechanism by which pharmaceutical agents can kill cancer cells. Apoptosis, sometimes referred to as "programmed cell death," naturally occurs in many tissues in the body. It plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin.

Standard chemotherapeutics can promote apoptosis not only in cancer cells, but also in normal human tissues. These agents often have particularly severe effect on tissues where apoptosis is especially pronounced (e.g., hair, gut, and skin). Thus, standard chemotherapeutics are inappropriate for cancer prevention, particularly if chronic administration is indicated.

Benzimidazoles (BZs) are a broad-spectrum class of anti-helmintics that display excellent activity against parasitic nematodes and, to a lesser extent, against cestodes and trematodes. BZs have also been shown to be very effective antiprotozoal agents that also have antifungal activity. It is currently believed that BZs exert their cytotoxic effects by binding to the microtubule system and disrupting its functions (Lacey, 1988; Friedman and Platzer, 1980). The suggestions that tubulin is a target for BZs has been supported by the results of drug-binding studies using enriched extracts of helminth and mammalian tubulin (Lacey, 1988). Moreover, competitive drug-binding studies using mammalian tubulin have shown that BZs compete for colchicine binding and inhibit growth of L1210 murine leukemia cells in vitro (Friedman and Platzer, 1978; Lacey and Watson, 1989). However, BZs are selectively toxic to nematodes when administered as antihelmintics but are not toxic to the host. In contrast, BZs suppress the in vitro polymerization of mammalian tubulin. Differences in both the affinity between the host and parasite macromolecules for BZ (Russell et al., 1992; Kohler and Bachmann, 1981) and the pharmacokinetics of BZs between the host and the parasite have been suggested as responsible for the selective toxicity of BZs (Gottschall et al., 1990) but the actual molecular basis of this selective toxicity remains unclear.

Mebendazole (MZ), or 5-benzoyl-2-benzimidazole carbamic acid methyl ester, is a member of the BZ class of compounds. Recently, MZ has been found to induce mitotic arrest and apoptosis by depolymerizing tubulin in non-small cell lung cancer cells. (Sasaki et al., 2002). MZ has also been found to elicit a potent antitumor effect on human cancer cell lines both in vitro and in vivo (Mukhopadhyay et al., 2002).

MZ was first introduced for the treatment of roundworm infections as a result of research carried out by Brugmans et al. (1971). It is the prototype of a series of broad-spectrum anthelmintics widely used in both animals and man (Michiels et al., 1982) as broad-spectrum anthelmintics for animal and human use (Van den Bossche et al., 1982). Related BZ derivatives with anthelmintic properties include albendazole and flubendazole.

MZ is highly effective in *ascariasis*, intestinal capillariasis, enterobiasis, trichuriasis, and hookworm (*Ancylostoma duodenale* and *Necator americanus*) infection as single or mixed infections. The drug is active against both larval and adult stages of the nematodes that cause these infections, and it is ovicidal for *Ascaris* and *Trichuris* (Keystone and Murdoch, 1979; Van den Bossche et al., 1982). Immobilization and death of susceptible gastrointestinal organisms occurs slowly, and clearance from the gastrointestinal tract may not be complete until a few days after treatment with MZ. Together with albendazole, MZ has shown some promise in the treatment of hydatid disease (Wilson et al., 1987).

MZ causes selective disappearance of cyoplasmic microtubules in the tegumental and intestinal cells of affected worms. Secretory substances accumulate in Golgi areas, secretion of acetylcholinesterase and uptake of glucose are impaired, and glycogen is depleted. These effects of MZ are not noted in host cells. MZ has a high affinity for parasite tubulin in vitro, but it also binds to host tubulin. The biochemical basis for its selective action is thus unclear (see Van den Bossche, 1981; Watts et al., 1982).

The conventional formulation of MZ is a tablet form. Tablets of MZ are poorly and erratically absorbed, and concentrations of the drug in plasma are low and do not reflect the dosage taken (Witassek et al., 1981). This is because MZ is highly lipophilic, with an aqueous solubility of less than 1.mu.g/ml. As a result, the conventional formulations of MZ result in low bioavailability of the drug and erratic absorption from the gastrointestinal tract. Many other BZs and BZ derivatives are also highly lipophilic and erratically absorbed from the gastrointestinal tract.

Therefore, there is a recognized need for improved oral pharmaceutical compositions of BZs and BZ derivatives, such as MZ, that result in greater bioavailability of the drug, are needed to treat systemic diseases such as cancer and deep-seated parasitic diseases with extraintestinal manifestations. In addition, parenteral formulations that result in greater release of BZs and BZ derivatives compared to conventional formulations would also be beneficial in treating these systemic conditions. Pharmaceutical compositions such as these would result in greater concentration of the drug in the bloodstream, and consequentially greater efficacy and therapeutic benefit. The present invention fulfills this long-standing need and desire in the art.

SUMMARY OF THE INVENTION

The present invention is based on the development of novel formulations BZ and BZ derivatives that result in improved drug solubility, improved drug release from the formulation, and improved bioavailability. Higher concentration of BZ or BZ derivative in the blood would result in greater therapeutic effect of this class of agents for use in the treatment of disorders in which treatment with BZs or BZ derivatives would be beneficial. For example, in the case of MZ, these diseases would include hyperproliferative diseases such as cancer, and extraintestinal and deep-seated parasitic disease such as hydatid disease.

The inventors have formulated MZ using co-solvency and microemulsion approaches which have yielded a drug concentration of 1.4-3.5 mg/ml, which is a 1,400-3,500 fold increase in solubility compared to conventional formulations of MZ. The inventors have assessed the formulations of MZ by in vitro USP dissolution, in vivo bioavailability studies in rats, and cell growth inhibition in cell line cultures of numerous types of cancer cells. A substantial improvement in release of the MZ from the formulations was demonstrated compared to an unformulated suspension, and bioavailability was improved 130 fold. An enhanced $IC_{50}$ of MZ from the formulations for cell growth in lung cancer cell lines was demonstrated compared to control formulations dissolved in dimethylsulfoxide and the formulations exhibited favorable characteristics in preclinical pharmacokinetic and pharmacodynamic studies. Therefore, the new BZ formulations are expected to have enhanced efficacy in the treatment of cancer and other hyperproliferative diseases.

Certain embodiments of the present invention are pharmaceutical compositions that include a BZ, a polyol, and a dipolar aprotic solvent. The definition of pharmaceutical composition is discussed in detail elsewhere in this specification, and encompasses a composition that does not produce an adverse, allergic or other untoward reaction when administered to an animal, or human, as appropriate.

Any BZ, BZ derivative, or combination of BZs is contemplated for use in the pharmaceutical compositions of the present invention. One of skill in the art would be familiar with this broad class of agents, and would understand that the pharmaceutical compositions of the present invention pertain to use of any member or members of this class of drugs. For example, the BZ included in the present pharmaceutical compositions may be a derivative having the formula:

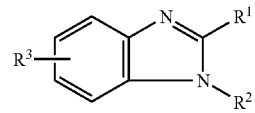

wherein $R^3$ is selected from the group that includes H, carboxyl (—$CO_2H$), hydroxyl, amino, chloro, difluormethoxy, benzoyl, phenyl-thio, pyridinyl, propyl-thio, diphenyl, methoxy(methoxy-dimethyl, p-yridinyl)methyl-(sulfonyl), fluorophenylmethyl-2-chloro, propenyl, chloroprophyl or esters (—$CO_2R^4$) wherein $R^4$ is selected from the group that includes alkoxy, haloalkyl, alkenyl, and cycloalkyl, wherein the alkyl groups have from 1-8 carbons, or $CH_3CH_2$ $(OCH_2CH_2)_n$—, or $CH_3CH_2CH_2(O\ CH_2CH_2CH_2)_n$, or $(CH_3)_2CH(OCH(CH_3)CH_2)_n$—, wherein n is from 1-3, wherein $R^1$ is OH, Cl, SH, carbamate or piperidin-4-yl, and $R^2$ is hydrogen, .alpha.-methylvinyl, 3-chloropropyl or piperidin-4-yl, or the pharmaceutically effective organic or inorganic salts thereof, or mixtures thereof.

In certain embodiments of the present invention, the BZ derivative is methyl 5-benzoylbenzimidazole-2-carbamate (mebendazole, MZ). Alternatively, in other embodiments, the BZ derivative may be methyl 5-(phenylthio)-2-benzimidazole carbamate (fenbendazole) or 5-methoxy-2-[[(4-methoxy-3,5-dimethyl-2-pyridinyl)methyl]sulfinyl]-1H-benzimidazole (omeprazole).

In certain other embodiments, the BZ derivative in the pharmaceutical compositions may be

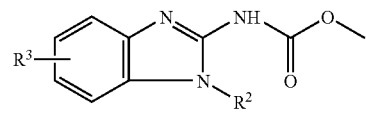

Alternatively, the BZ derivative of the pharmaceutical compositions may be

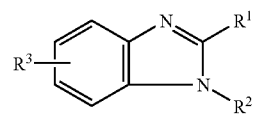

In still other embodiments, the pharmaceutical composition includes a BZ derivative that is

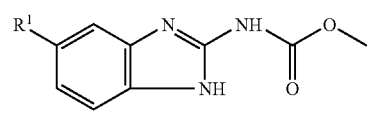

The pharmaceutical compositions of the present invention contemplate use of any polyol. One of ordinary skill in the art would be familiar with the class of agents known as polyols, and would understand that any of these agents may be included in the pharmaceutical compositions of the present invention. For example, the polyol may be polyethylene glycol (PEG) 200, PEG 300, PEG 400, PEG 600, 1,2-propylene diol, glycerol, or ethylene glycol. In certain embodiments, the polyol may be PEG 400. The pharmaceutical compositions of the present invention can include a single polyol, or more than one polyol.

The pharmaceutical compositions of the present invention include dipolar aprotic solvents. A dipolar aprotic solvent is a solvent with a comparatively high relative dielectric constant, greater than about 15, and a sizable permanent dipole moment, that cannot donate suitably labile hydrogen atoms to form strong hydrogen bonds. The term is something of a misnomer, since such solvents are usually not aprotic but protophilic and, at most, weakly protogenic. One of ordinary skill in the art would be familiar with the class of agents typically known as dipolar aprotic solvents, and would understand that any of these agents may be included in the pharmaceutical compositions of the present invention.

For example, the dipolar aprotic solvents include N,N-dimethylacetamide (DMA) or dimethylsulfoxide (DMSO). In certain embodiments, the pharmaceutical compositions include N,N-dimethylacetamide as the dipolar aprotic solvent. In certain other embodiments, the dipolar aprotic solvent is dimethylsulfoxide. In some embodiments, the pharmaceutical compositions include more than one dipolar aprotic solvent. For example, the pharmaceutical compositions may include N,N-dimethylacetamide and dimethylsulfoxide.

The pharmaceutical compositions of the present invention contemplate any ratio of polyol to dipolar aprotic solvent by weight. However, in certain embodiments of the present invention, the ratio of polyol to dipolar aprotic solvent by weight is 3:1. For example, the pharmaceutical compositions of the present invention may include PEG 400 and N,N-dimethylacetamide in a ratio of 3:1 by weight. Alternatively, certain embodiments of the present invention may include PEG 400 and dimethylsulfoxide in a 3:1 ratio by weight.

In some embodiments of the present pharmaceutical compositions, the ratio of polyol to dipolar aprotic solvent is 7:1 by weight. For example, the pharmaceutical may include PEG 400 and dimethylsulfoxide in a ratio of 7:1 by weight, or PEG 400 and N,N-dimethylacetamide in a ratio of 7:1 by weight.

In certain embodiments of the present pharmaceutical compositions, the composition includes water. Any amount of water is contemplated by the present invention. However, in certain embodiments, the relative ratio of polyol:dipolar aprotic solvent:water is 3:1:1 by weight. For example, some embodiments include a pharmaceutical compositions that may include PEG 400: N,N-dimethylacetamide:water in a 3:1:1 ratio by weight. Alternatively, other embodiments of the present pharmaceutical compositions include PEG 400: dimethylsulfoxide:water in a 3:1:1 ratio by weight.

In other embodiments of the present pharmaceutical compositions, the relative ratio of polyol:dipolar aprotic solvent:water is 7:1:2. For example, the pharmaceutical composition may include PEG 400:dimethylsulfoxide:water in a 7:1:2 ratio by weight.

Additional embodiments of the present invention pertain to pharmaceutical compositions that include (1) a BZ; (2) an oil; (3) a dipolar aprotic solvent; and (4) a surfactant. Members of the class of BZ and BZ derivatives are discussed above, and elsewhere in this specification. As discussed above, one of skill in the art would be familiar with this broad class of agents, and would understand that the pharmaceutical compositions of the present invention pertain to use of any member or combination of members of this class of drugs. For example, as discussed above, the BZ derivative may be MZ.

Any oil is contemplated for use in the present invention. One of ordinary skill in the art would be familiar with the wide variety of oils that are available for inclusion in pharmaceutical compositions. For example, the oil may be super refined corn oil, super refined cottonseed oil, olive oil, super refined peanut oil, super refined soybean oil, Captex 200, Captex 355, Miglyol 812, or Myvacet 9-45. In certain embodiments of the present pharmaceutical compositions, the oil is Captex 200. In certain other embodiments of the present pharmaceutical compositions, the oil is Myglyol 812. The pharmaceutical compositions of the present invention also contemplate compositions containing more than one oil or any combination of oils.

Any surfactant is contemplated for use in the present invention. One of ordinary skill in the art would be familiar with the wide variety of surfactants that are available for inclusion in pharmaceutical compositions of the present invention. For example, in certain embodiments, the pharmaceutical compositions of the present invention include Tween 80 as the surfactant. In other embodiments, the pharmaceutical compositions include Arelacel 80 as the surfactant. The pharmaceutical compositions of the present invention may include a single surfactant, or any combination of surfactants.

Surfactants of any hydrophilic-lipophilic balance (HLB) are contemplated for use in the present invention. The HLB of a surfactant is an empirical quantity, on an arbitrary scale, which is a measure of the polarity of a surfactant or mixture of surfactants. It is a widely known and used term which would be very familiar to one of ordinary skill in the art. In general, a high HLB surfactant is a surfactant with an HLB that is 7 or above 7, and a low HLB surfactant is a surfactant with an HLB below 7. More than one surfactant in the composition may provide for versatility, greater stability, and enhanced drug absorption. For example, some embodiments of the present invention include a combination of Tween 80 and Arelacel 80 as the surfactants.

In certain embodiments of the present pharmaceutical compositions, the surfactants used are only high HLB surfactants. Other embodiments of the present pharmaceutical compositions include only low HLB surfactants. Alternatively, the pharmaceutical compositions of the present invention include a mixture of both high HLB surfactants and low HLB surfactants.

As discussed above, the pharmaceutical compositions of the present invention may further be defined as including water. Any amount of water is contemplated in the present pharmaceutical compositions, as long as any amount of the previously defined components is present.

The pharmaceutical compositions of the present invention may further be defined as a microemulsion. A microemulsion is herein defined as a thermodynamically stable dispersion of one liquid phase into another, stabilized by an interfacial film of surfactant. This dispersion may be either oil-in-water or water-in-oil. Microemulsions are often clear solutions, as the droplet diameter may be approximately 100 nanometers or less. However, solutions that are not clear are encompassed within the definition of microemulsion used herein, and any droplet diameter is contemplated in this definition.

Examples of certain embodiments of the present invention include pharmaceutical compositions that include (1) MZ; (2) 10%-60% by weight of an oil; (3) 2%-30% by weight of a dipolar aprotic solvent; (4) 5%-50% by weight of a first surfactant; and (5) 5%-50% by weight of a second surfactant.

The pharmaceutical compositions of the present invention contemplate any concentration of MZ. For example, in certain embodiments the concentration of MZ is greater than 1.4 mg/ml. For example, the MZ concentration may be about 1.5 mg/ml, about 1.6 mg/ml, about 1.7 mg/ml, about 1.8 mg/ml, about 1.9 mg.ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, or any range of concentration or increments of concentration derivable therein.

In other embodiments, the concentration of MZ is 0.3-3.0 mg/ml. For example, the concentration of MZ may be about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, or any range of concentration or increment of concentration derivable therein. In other embodiments, the concentration of MZ is 0.5 mg/ml to 2.5 mg/ml or 0.3 mg/ml to 3.0 mg/ml.

In certain specific embodiments, the concentration of MZ is about 1.2 mg/ml. In other embodiments, the concentration of MZ is about 1.5 mg/ml. In still other embodiments, the concentration of MZ is about 1.7 mg/ml. In additional embodiments, the MZ concentration is about 1.8 mg/ml. In other embodiments, the MZ concentration is about 1.85 mg/ml. In other embodiments, the MZ concentration is about 1.9 mg/ml. In further embodiments, the MZ concentration is about 2.0 mg/ml. In still further embodiments, the MZ concentration is about 2.1 mg/ml. In certain other embodiments, the concentration of MZ is about 2.3 mg/ml. In further embodiments, the MZ concentration is about 2.6 mg/ml.

The concentration of BZ in the pharmaceutical compositions of the present invention may be determined by any method known to those of skill in the art. One of ordinary skill in the art would be familiar with the range of techniques used to determine concentration of a BZ or BZ derivative in a composition. For example, the concentration of BZ may be determined by HPLC. In certain embodiments wherein the BZ derivative is MZ, HPLC may be used to determine the concentration of MZ. Use of HPLC to determine concentration of MZ in a pharmaceutical composition of the present invention is discussed further in the specification below.

In some embodiments of the present invention, the pharmaceutical compositions may include water. Any amount of water is contemplated in the present invention, as long as the other required constituents are present. In addition, the pharmaceutical compositions of the present invention contemplate the presence of components in addition to those that have been delineated. A greater discussion of potential additional additives is discussed in the specification below.

Some embodiments of the present pharmaceutical compositions include Tween 80 as the first surfactant and Arelacel 80 as the second surfactant. For example, in some embodiments, the pharmaceutical compositions include 10%-60% by weight of Captex 200, 3%-30% by weight of N,N-dimethylacetamide, 5%-50% by weight of Tween 80, 5%-50% by weight of Arelacel 80, and 2%-20% by weight of water. In other embodiments, the pharmaceutical composition includes 28.9% by weight of Captex 200, 13.7% by weight of N,N-dimethylacetamide, 28.8% by weight of Tween 80, 28.8% by weight of Arelacel 80, and 13% water.

In certain other embodiments, the pharmaceutical composition includes 10%-60% by weight of Captex 200, 2%-20% by weight of dimethylsulfoxide, 10%-40% by weight of Tween 80, 10%-40% by weight of Arelacel 80, and 10%-20% by weight of water. For example, the pharmaceutical composition may include 50.1% by weight of Captex 200, 12.6% by weight of dimethylsulfoxide, 12.6% by weight of Tween 80, 12.6% by weight of Arelacel 80, and 12.1% by weight of water. The pharmaceutical composition may also include 42.6% by weight of Captex 200, 10.7% by weight of dimethylsulfoxide, 16.1% by weight of Tween 80, 16.1% by weight of Arelacel 80, and 14.5% by weight of water. In other examples, the pharmaceutical compositions includes 38.4% by weight of Captex 200, 9.6% by weight of dimethylsulfoxide, 19.2% by weight of Tween 80, 19.2% by weight of Arelacel 80, and 13.6% by weight of water. In further examples, the pharmaceutical composition includes 34.7% by weight of Captex 200, 8.7% by weight of dimethylsulfoxide, 21.7% by weight of Tween 80, 21.7% by weight of Arelacel 80, and 13.2% by weight of water.

The pharmaceutical compositions of the present invention may also include 10%-60% by weight of super refined soybean oil, 2%-20% by weight of dimethylsulfoxide, 10%-40% Tween 80, 10%-40% Arelacel 80, and 0.5%-15% by weight of water. For example, the pharmaceutical composition may include 56.5% by weight of super refined soybean oil, 14.1% by weight of dimethylsulfoxide, 14.1% by weight of Tween 80, 14.1% by weight of Arelacel 80, and 1.2% by weight of water. In other embodiments of the present invention, the pharmaceutical composition includes 44.2% by weight of super refined soybean oil, 11.1% by weight of dimethylsulfoxide, 16.6% by weight of Tween 80, 16.6% by weight of Arelacel 80, and 11.5% by weight of water. In further embodiments, the pharmaceutical composition includes 40.0% by weight of super refined soybean oil, 10.0% by weight of dimethylsulfoxide, 20.0% by weight of Tween 80, 20.0% by weight of Arelacel 80, and 10.0% by weight of water. In additional embodiments, the pharmaceutical composition includes 35.7% by weight of super refined soybean oil, 8.9% by weight of dimethylsulfoxide, 22.3% by weight of Tween 80, 22.3% by weight of Arelacel 80, and 10.8% by weight of water.

Embodiments of the present invention also include pharmaceutical compositions that include 10%-60% by weight of Miglyol 812, 2%-20% by weight of dimethylsulfoxide, 10%-40% by weight of Tween 80, 10%-40% by weight of Arelacel 80, and 5%-20% by weight of water. For example, the pharmaceutical composition may include 50.4% by weight of Miglyol 812, 12.6% by weight of dimethylsulfoxide, 12.7% by weight of Tween 80, 12.7% by weight of Arelacel 80, and 11.6% by weight of water. In other examples, the pharmaceutical composition includes 42.4% by weight of Miglyol 812, 10.6% by weight of dimethylsulfoxide, 15.9% by weight of Tween 80, 15.9% by weight of Arelacel 80, and 15.2% by weight of water. In other examples, the pharmaceutical compositions include 39.2% by weight of Miglyol 812, 9.8% by weight of dimethylsulfoxide, 19.6% by weight of Tween 80, 19.6% by weight of Arelacel 80, and 11.8% by weight of water. The pharmaceutical composition of the present invention may also include 34.7% by weight of Miglyol 812, 8.7% by weight of dimethylsulfoxide, 21.8% by weight of Tween 80, 21.8% by weight of Arelacel 80, and 13.0% by weight of water.

The present pharmaceutical compositions can be formulated by any method known to those of skill in the art. For example, in certain embodiments the pharmaceutical composition is formulated for parenteral administration to a subject. Parenteral administration is defined as administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

In other embodiments of the present invention, the pharmaceutical composition is further defined as being suitable for administration through the digestive tract or through non-invasive topical and regional routes. For example, the pharmaceutical preparation may be administered orally. In other embodiments, the pharmaceutical preparation is administered intranasally, topically, locally, by inhalation, by continuous infusion, or by localized perfusion by bathing target cells directly, via a catheter, or via lavage.

Embodiments of the present invention also include drug delivery systems comprising a benzimidazole derivative formulated in a microemulsion or nanoemulsion for improved release and bioavailability to a cell or tissue in a subject. These emulsions may comprise a self-nanoemulsifying drug delivery system or a self-emulsifying drug delivery system. In some embodiments the drug delivery system is defined as comprising the 1) benzimidazole derivative, 2) an oil, 3) a surfactant, 4) a cosurfactant, and 5) a dipolar aprotic solvent. In other embodiments the drug delivery system further may include water, particularly at a weight ratio of about 50%. In particular embodiments the benzimidazole derivative is methyl 5-benzoylbenzimidazole-2-carbamate (mebendazole) at a at a concentration of about 0.9 mg/ml to about 2 mg/ml.

The present drug delivery systems may have a formulation comprising an oil that is Captex 200 or Myglyol, for example, in a weight ratio of about 14% to about 42%. The formulation may comprise a surfactant that is Tween 80 and a cosurfactant that is Transcutol or Capmul MCM., for example, in individual weight ratios of about 6% to about 48% and with a surfactant:cosurfactant ratio of about 1:0.5 to about 1:1. The formulation may comprise a dipolar aprotic solvent that is dimethylsulfoxide, for example, in a weight ratio of about 5% to about 10%. The system may form an emulsion having a droplet diameter of about 35 nm to less than 500 nm. A self-nanoemulsifying drug delivery system may comprise droplets with a diameter of about 35 to less than 100 nm. A self-emulsifying drug delivery system may comprise droplets with a diameter of about 141 nm to less than 500 nm.

In certain embodiments the drug delivery system may comprise methyl 5-benzoylbenzimidazole-2-carbamate, about 4% to about 42% by weight of an oil, about 20% to about 41% by weight each of a surfactant and a cosurfactant in about a 1:0.75 to about 1:1 ratio, and about 5% to about 10% by weight of dimethylsulfoxide. In these embodiments the methyl 5-benzoylbenzimidazole-2-carbamate is at a concentration of about 0.9 mg/ml to about 2 mg/ml. In one particular example the drug delivery system may comprise about 4% to about 9% by weight of Captex 200 and about 20% to about 41% by weight each of Tween 80 and Transcutol or Capmul. In this particular example the drug delivery system further may comprise about 50% by weight of water. Also, the system may be the self-nanoemulsifying drug delivery system where the droplet diameter is about 35 to about 37 nm. In another particular example the drug delivery system may comprise about 42% by weight of Myglyol, about 27% by weight of Tween 80 and Transcutol and about 21% by weight of Capmul. In this other particular example the system may be a self-emulsifying drug delivery system where the droplet diameter is about 141-145 nm.

In still other embodiments of the present invention, the drug delivery systems are further defined as being suitable for improving the bioavailability of a benzimidazole derivative for treatment of a pathophysiological condition in a subject. Delivering the benzimidazole derivative to the subject, either parenterally or orally, improves its bioavailability because an efficacious combination of droplet diameter and surfactant: cosurfactant ratio within the emulsion comprising the system increases the half-life of the benzimidazole derivative within the tissue. In particular embodiments the droplet diameter is about 34 nm to about 143 nm and the surfactant:cosurfactant ratio is about 1:1. Thus, it is contemplated that the pharmaceutical compositions and drug delivery systems of the present invention are suitable to treat a pathophysiological condition such as cancer, for example, a lung cancer, or to treat a pulmonary infection with other antimicrobial agents.

In a related embodiment, the drug delivery systems are defined further as being suitable for increasing concentration and retention of a benzimidazole derivative within the lung of a subject in need thereof. Formulating a microemulsion comprising the benzimidazole derivative and other components of the drug delivery system with a droplet size within the microemulsion of about 35 nm to less than 100 nm provides for increased concentration and retention of the benzimidazole derivative within the lung upon parenteral administration of the microemulsion thereto.

In still further embodiments, the drug delivery systems are defined as being suitable for defining the hemolytic safety of microemulsions of a benzimidazole derivative during a therapeutic treatment regimen for a subject. Formulating a microemulsion comprising the benzimidazole derivative and other components of the drug delivery system with a low surfactant: cosurfactant content by weight of about 27% to about 42% results in a reduced hemolytic potential upon parenteral administration of the microemulsion to the subject.

Other and further aspects, features and advantages of the present invention will be apparent from the following description of the presently preferred embodiments of the invention given for the purpose of disclosure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 12G is the determination of hemolytic potential of PM1 formulation.

FIG. 16. Schematic Representation of a Three-Compartmental Model for Linking the Mbz Concentrations in Lung and in Plasma.

DETAILED DESCRIPTION OF THE INVENTION

Figure 1:
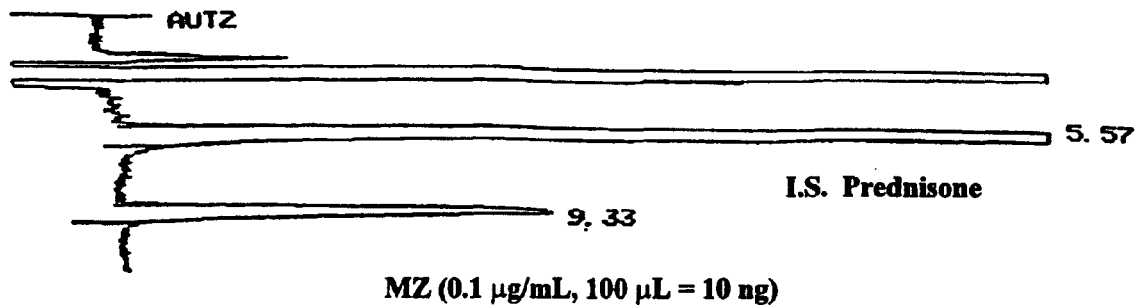
FIG. 1. Authentic HPLC chromatogram of MZ (0.1 μg/mL, 100 μL-10 ng).

As used herein, the term "a" or "an", when used in conjunction with the term "comprising" in the claims and/or the specification, may refer to "one," but it is also consistent with the meaning of "one or more," "at least one," and "one or more than one." some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

As used herein, the terms "pharmaceutical," "pharmaceutically," or "pharmacologically acceptable" refer to molecular entities and compositions that do not produce an adverse, allergic or other untoward reaction when administered to an animal, or human, as appropriate. The term "pharmaceutical" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents or anthelmintics, can also be incorporated into the compositions.

As used herein, the term "hemolytic potential" or "H10%" refers to the ratio of a microemulsion formulation to blood for which 90% of the blood cells are viable.

As used herein, the term "subject" refers to any recipient of a benzimidazole derivative via the pharmaceutical compositions or drug delivery systems described herein.

The present invention seeks to exploit the inventors' discovery by providing pharmaceutical compositions of BZs and BZ derivatives that have improved and predictable bioavailabilities. BZs and BZ derivatives often have limited and erratic oral bioavailability due to poor solubility of the compound in aqueous medium. As a result, these drugs cannot be efficiently delivered in convention dosage forms. For example, MZ has a solubility in aqueous medium of less that 1 μg/ml. The inventors have discovered certain oral and parenteral formulations of BZs and BZ derivatives, such as MZ, using co-solvency and microemulsion approaches, respectively. The parenteral formulation of MZ was developed to circumvent the drawback of extensive first-pass metabolism of MZ known to be associated with oral administration. These formulations can be applied for the therapy of diseases wherein BZs and BZ derivatives formulated for increased bioavailability may be efficacious, such as hyperproliferative diseases, neoplastic disease and extraintestinal parasitic diseases.

A. Benzimidazoles and Derivatives of Benzimidazoles

Benzimidazoles (BZs) are broad-spectrum antihelmintics that display excellent activity against parasitic nematodes and, to a lesser extent, against cestodes and trematodes. BZs have also been shown to be very effective antiprotozoal agents and to have antifungal activity. It is currently believed that BZs exert their cytotoxic effects by binding to the microtubule system and disrupting its functions (Lacey, 1988; Friedman and Platzer, 1980). The suggestion that tubulin is a target for BZs has been supported by the results of drug-binding studies using enriched extracts of helminth and mammalian tubulin (Lacey, 1988). Moreover, competitive drug-binding studies using mammalian tubulin have shown that BZs compete for colchicine binding and inhibit growth of L1210 murine leukemia cells in vitro (Friedman and Platzer, 1978; Lacey and Watson, 1989). However, BZs are selectively toxic to nematodes when administered as antihelmintics but are not toxic to the host. In contrast, BZs suppress the in vitro polymerization of mammalian tubulin. Differences in both the affinity between the host and parasite macromolecules for BZ (Russell et al., 1992; Kohler and Bachmann, 1981) and the pharmacokinetics of BZs between the host and the parasite have been suggested as responsible for the selective toxicity of BZs (Gottschall et al., 1990) but the actual molecular basis of this selective toxicity remains unclear.

Benzimidazoles and derivatives of benzimidizoles are defined herein to have the formula:

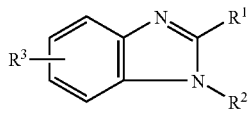

wherein R is selected from the group consisting of H, carboxyl (—CO$_2$H), hydroxyl, amino or esters (—CO$_2$R') wherein R' is selected from the group consisting of alkoxy, haloalkyl, alkenyl, and cycloalkyl wherein the alkyl groups have 1-8 carbons or CH$_3$CH$_2$(OCH$_2$CH$_2$)$_n$— or CH$_3$CH$_2$CH$_2$(OCH$_2$CH$_2$CH$_2$)$_n$ or (CH$_3$)$_2$CH(OCH(CH$_3$)CH$_2$)$_n$ where n is from 1-3 and the pharmaceutically acceptable organic or inorganic addition salts thereof; wherein R$^3$ is selected from the group consisting of H, carboxyl (—CO$_2$H), hydroxyl, amino, chloro, difluormethoxy, benzoyl, phenyl-thio, pyridinyl, propyl-thio, diphenyl, methoxy(methoxy-dimethyl,pyridinyl)methyl-(sulfonyl), fluorophenylmethyl-2-chloro, propenyl, chloroprophyl or esters (—CO$_2$R$^4$) wherein R$^4$ is selected from the group consisting of alkoxy, haloalkyl, alkenyl, and cycloalkyl, wherein the alkyl groups have from 1-8 carbons, or CH$_3$CH$_2$(OCH$_2$CH$_2$)$_n$— or CH$_3$CH$_2$CH$_2$(OCH$_2$CH$_2$CH$_2$)$_n$— or (CH$_3$)$_2$CH(OCH(CH$_3$)CH$_2$)$_n$—, wherein n is from 1-3, wherein R$^1$ is OH, Cl, SH, carbamate or piperidin-4-yl, and R$^2$ is hydrogen, alpha.-methylvinyl, 3-chloropropyl or piperidin-4-yl, or the pharmaceutically effective organic or inorganic salts thereof, or mixtures thereof. For R$^4$, the preferred alkyl groups are straight chain, the preferred the halogen is substituted on the terminal carbon, the preferred halogen is chlorine, the preferred cycloalkyl groups are those having 3-6 carbon atoms, and the cycloalkyl groups also include those which are substituted on an alkyl chain, 2-cyclopropylethyl, cyclopropylmethyl, 2-cyclopropylpropyl or 2-cyclopropylpropyl or cyclohexylmethyl.

BZs have some anti-tumor growth properties in vitro (WO 98/513304; WO 98/32440). The efficacy of BZs in vivo as an anti-tumor treatment has been limited to tumors already in regression following chemotherapeutic treatment.

Alternative benzimidazoles are: fenbendazole, albendazole, albendazole sulfone, oxibendazole, rycobendazole, thiabendazole, oxfendazole, flubendazole and carbendazim. Alternative anti-helminthic drugs are the imidazoles: niridazole and levimasole, the piperazines: piperazine and diethylcarbamazine, the isothiocyanates: amoscanate and CGP 6140. In addition, suramin, ivermectin, hycanthone, metrifonate, oxamniquine and praziquantel are anti-helminthic drugs.

B. Treatment of Cancers Using Benzimidazoles

There is evidence, as discussed above, that BZs or BZ derivatives may be useful in the treatment of hyperproliferative diseases, such as cancer. In particular, the use of BZs in the treatment of cancer is discussed in detail in U.S. patent application Ser. No. 10/043,877, which is specifically incorporated by reference herein. In addition, MZ has also been found to elicit a potent antitumor effect on human cancer cell lines both in vitro and in vivo (Mukhopadhyay et al., 2002; Liang et al., 2002). Mukhopadhyay et al., 2002, and Liang et al., 2002, are specifically incorporated by reference herein.

Of particular interest are patients that have wild-type tumor suppressor (e.g., p53) function. The tumor suppressor status of the tumor cells can be determined using any conventional methods, examples of which are described below. Patients may, but need not, have received previous chemo-, radio-, or gene therapies. Optimally, patients will have adequate bone marrow function (defined as peripheral absolute granulocyte count of >2000/mm$^3$ and platelet count of 100,000/mm$^3$), adequate liver function (bilirubin ≤1.5 mg/dl) and adequate renal function (creatinine <1.5 mg/dl).

Patients with cancer may be treated with a pharmaceutically acceptable form of BZ or a functional analog thereof. This administration could be in the form of, for example, an intratumoral injection, or indeed, any other method of application that is routinely used and well known to one of skill in the art, e.g., oral, systemic, local, regional. A biopsy of the lesions to be injected may be performed and the tissue stored for immunohistochemistry analyses.

The dose of BZ typically will be reconstituted into a pharmaceutically acceptable form immediately prior to administration. The dose of BZ will be determined depending on the clinical condition to be treated. For example, if the disease is cancer, the starting dose will be approximately 0.1 to 1 mg BZ/kg body weight. Of course, this may vary depending on the disease to be treated, the size of the tumor, the rate at which the tumor is growing, etc.

C. Pharmaceutical Compositions and Routes of Administration

1. Overview

The objective of the present invention was to develop both parenteral and oral formulations of BZ and BZ derivatives, such as MZ, in order to achieve improved and predictable bioavailabilities. The invention stems from the desire to overcome the problem of limited and erratic oral bioavailability due to poor solubility in aqueous medium of many BZs and BZ derivatives. The parenteral and oral formulations of BZs described in greater detail below were developed using co-solvency and self-emulsifying/microemulsion approaches, respectively. The parenteral formulation of BZ were developed to circumvent the drawback of the extensive first-pass metabolism of MZ and other BZs known to be associated with oral administration.

The inventors have investigated the solubility of MZ in various solvents, such as N,N-dimethylacetamide (DMA), DMSO, and polyethylene glycol-400 (PEG), as discussed in greater detail in the examples below. As primary solvents, the solvents would be miscible in secondary solvents, examples of which are normal saline, dextrose in water (5% or 10%), and water. These solvents are examples of vehicles in which BZs such as MZ could be suitably solubilized, yet be safe for human administration, alone or in combinations with other drugs. The solubility of BZ in individual solvent vehicles is shown in Table I below.

Virtually no MZ is absorbed through the intestinal tract after oral administration, making it impossible to even investigate its use as an oral antimicrobial against systemic infections. Parenteral administration would therefore be the logical approach to evaluate MZ and other BZs as therapy for deep-seated, systemic fungal infections and also in the treatment of cancer and other hyperproliferative diseases.

2. Effective Amount of BZs and BZ Derivatives

Pharmaceutical compositions of the present invention will include an effective amount of a BZ or a BZ derivative or a mixture thereof that is clinically determined to be useful in the treatment of the particular disease under consideration. For example, an effective amount of a BZ or a BZ derivative in a patient with cancer may be an amount that promotes expression of wild-type tumor suppressor genes, and/or inhibits angiogenesis. Alternatively, an effective amount of a BZ or BZ derivative or mixture thereof may be an amount that promotes death of parasites and/or regression of clinical findings associated with the infection. Such compositions will generally be dissolved or dispersed in a pharmaceutically acceptable carrier.

In cancer patients, the access to parenteral BZs such as MZ will be particularly important, since their intestinal absorption is often perturbed after chemotherapy, aggravating the already erratic intestinal absorption of various medications. The parenteral route will also make it possible to circumvent unpredictable first-pass metabolic effects in the liver, well known to alter the bioavailability of numerous pharmacologically active agents after oral dosing. Further, the availability of MZ for effective and reliable systemic administration will for the first time make it possible to clinically compare the activity of MZ against other treatments for cancer and deep-seated fungal infections.

3. Oral Administration

In addition to the compounds formulated for parenteral administration, such as those for intravenous, subcutaneous, or intramuscular injection, other pharmaceutically acceptable forms include, solutions suitable for oral administration. The term "oral administration" includes any form of administration of drug through the oral cavity and into the gastrointestinal tract. The pharmaceutical compositions of the present invention may be formulated for delivery to a subject by any means. For example, the compositions may be formulated as mouthwashes, mouthrinses, solutions for administration through a nasogastric tube, and the like.

4. Compositions Suitable for Parenteral Administration

As discussed in the summary of the invention, the active compounds of the present invention will often be formulated for parenteral administration, e.g., formulated for injection by any route other than through the digestive tract, such as via the intravenous, intramuscular, subcutaneous, or even intraperitoneal routes. The definition of parenteral administration is discussed further in the summary of the invention. Typically, the compositions can be prepared as injectables, either as liquid solutions or suspensions for any parenteral but intravenous routes; solid forms suitable for using to prepare solutions or suspensions upon the addition of a liquid prior to injection can also be prepared; and the preparations can also be emulsified.

5. Formulation Principles

Solutions of the active compounds as free base or pharmacologically acceptable salts can be prepared in water suitable for mixture with a surfactant, such as hydroxypropylcellulose or polysorbate. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include, for example, sterile aqueous solutions or dispersions, and formulations including sesame oil, peanut oil or aqueous propylene glycol or other solvent as discussed in the examples below. In all cases the form must be sterile and must be fluid to the extent that easy syringability exists. It must be chemically and physically stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. Preparation of cosolvency formulations and microemulsion formulations of BZs or BZ derivatives is discussed in greater detail in the examples below.

The proper fluidity can be maintained, for example, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In certain cases, the therapeutic formulations of the invention could also be prepared in forms suitable for topical administration, such as in gels, creams, and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in aqueous solution, for example, the solution should be suitably buffered if necessary. These particular solutions are especially suitable for intravenous, intramuscular, subcutaneous and intraperitoneal administration. Some variation in dosage will necessarily occur depending on the condition of the subject being treated. The person responsible for administration will, in any event, determine the appropriate dose for the individual subject.

6. Formulation of BZs and BZ Derivatives that are Sparingly Soluble in Water: Co-Solvency Systems Many BZs are only sparingly soluble in aqueous solutions. As discussed above, it is therefore an aspect of the current invention that the BZ compound be in a formulation which allows for an increased solubilization of the BZ or for a more effective dispersion.

Generation of some of the pharmaceutical compositions of the present invention are based on the principle of cosolvency (Spiegel and Noseworthy, 1963; Yalkowsky and Roseman, 1981). The examples show that pharmaceutical compositions of MZ can be generated without destroying its anti-cancer properties. Further, the animal studies provide evidence that the preferred vehicles are nontoxic and safe for administration and should be acceptable for human administration in the proposed concentrations and total doses to be utilized; indeed, DMA, DMSO, and PG have been used for solubilization of various pharmacologically active agents used in man (NIH Pub. 84-2141, 1984; Weiss et al., 1962; Kim, 1988). The parenteral administration of PEG has been studied in detail in a simian model (Lockard et al., 1979), and PEG has subsequently been used clinically as a (covalently bound) carrier of L-asparaginase in the treatment of lymphocytic leukemia and lymphoma (Keating et al., 1993). DMSO is also extensively used as a cryoprotective agent for low-temperature storage of human bone marrow and peripheral blood derived hematopoietic stem cell preparations to be used for transplantation after high-dose chemotherapy (McGann, 1978; Gorin, 1986; Davis and Rowley, 1990; Gorin, 1992). No serious adverse effects have been experienced from the use of these vehicles. The clinical use of normal saline, dextrose in water (5-70%), and aqueous lipid emulsion are well established means to alter the fluid and electrolyte balance and to supply parenteral nutrition. Normal saline and dextrose in water are extensively used to dilute various medications for parenteral use.

7. Formulation of BZs and BZ Derivatives that are Sparingly Soluble in Water: Microemulsion Systems The preparation and use of microemulsions in the formulation of drugs, proteins, and the like are known in the art. A microemulsion is herein defined as a thermodynamically stable dispersion of one liquid phase into another, stabilized by an interfacial film of surfactant. This dispersion may be either oil-in-water or water-in-oil. Microemulsions are often clear solutions, as the droplet diameter may be approximately 100 nanometers or less. However, solutions that are not clear are encompassed within the definition of microemulsion used herein, and any droplet diameter is contemplated in this definition.

Surfactants can be added to the aqueous solution to increase solubility and stability of a solution or dispersion. Surfactants, discussed in greater detail in the summary of the invention, are organic molecules which contain both hydrophilic and hydrophobic ends. The hydrophilic end, which is either polar or ionic, dissolves readily in water. The hydrophobic, or non-polar, end, however, does not dissolve in water and will move as far away from water as possible. When a small concentration of surfactant is added to water, the hydrophobic end will immediately rise to the surface or orient towards a less polar group. The addition of surfactants in a BZ solution increase the solubility and/or stability of the BZ-surfactant solution relative to the BZ alone.

D. Methods of Measuring Concentration of Drugs in a Composition

Following preparation of the pharmaceutical compositions of the present invention, it may be desirable to quantify the amount of BZ or BZ derivative in the pharmaceutical composition. Methods of measuring concentration of a drug in a composition include numerous techniques that are well-known to those of skill in the art. Selected examples include chromatographic techniques. There are many kinds of chromatography which may be used in the present invention: drug-specific assays, adsorption, partition, ion-exchange and molecular sieve, and many specialized techniques for using them including column, paper, thin-layer chromatography, gas chromatography, and high performance liquid chromatography (HPLC). One of ordinary skill in the art would be familiar with these and other related techniques.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods
Materials

Mebendazole (MZ, Lot 90K1145), polyethylene glycol (PEG) 400 (Lot 121H0052), N,N-demethylacetamide (DMA) (Lot 129H3498), and dimethylsulfoxide (DMSO) (Lot 94H0358) were purchased from Sigma Chemical Co. (St. Louis, Mo.). Propylene glycol (Lot 940629) and olive oil (Lot CAS8001-25-0) were obtained from Wood Scientific, Inc (Houston, Tex.). Triacetin was purchased from Lancaster Synthesis, Inc. (Windham, N.H.). Super refined cottonseed oil (Lot GAB-217NP), super refined peanut oil (Lot BSS-429NP) and super refined soybean oil (Lot SB4-393NP) were supplied by Croda (Mill Hall, Pa.). Captex 200 (C8/C10 diesters of propylene glycol, Lot 10505-6) and Captex 355 (C8/C10 triglycerides from coconut oil) were provided by Abitec Corporation (Janesville, Wis.). Miglyol 812 (C8/C10 triglycerides from coconut oil, Lot 1995050866) and Myvacet 9-45 (distilled acetylated monoglycerides; Lot 960225) were obtained from Eastman Chemical Products. Tween 80 (polyoxytheylene [20] sorbitan monooleate; Lot 32332) and Arelacel 80 (sorbitan monooleate NF, NLB=4.3, Lot 27255) were supplied by ICI Americans Inc. (Wilmington, Del.). Cremophor RH 40 (PEG-40 hydrogenated castor oil, HLB=13.5) was from BASF (Parsippany, N.J.).

HPLC Assay of MZ

An HPLC assay was developed to quantify MZ in the formulations and in the release samples. The assay used a reversed-phase .mu.Bondapak $C_{18}$ column (300×3.9 mm, 10 µm, Waters Corporation, Milford, Mass.) preceded by a C.sub.18 guard column. The mobile phase, which was filtered and degassed prior to use, consisted of acetonitrile/0.05 M potassium monobasic phosphate, pH 6.5 (40:60, v/v). Prednisone was used as the internal standard (IS). The flow rate was 1.2 ml/min. The solvent delivery system was a Consta-Metric 3500 LDC Analytical Model system. MZ and IS were detected with a SpectroMonitor 3200 programmable multi-wavelength UV detector set at 254 nm. Peak area ratios measured by a Milton Ray CI-4100 data module integrator (LDC Analytical) were used to construct standard curves and to determine the concentrations of MZ in the samples. The assay was later modified for the quantification of MZ in blood samples, as described below.

Evaluation of MZ Solubility in Various Solvent Media

The solubility of MZ in aqueous and in fourteen other solvent media, including six pharmaceutical solvents (methanol, PEG 400, propylene glycol, triacetin, DMA, and DMSO) and eight naturally occurring and synthetic oils (super refined cottonseed oil, olive oil, super refined peanut oil, super refined soybean oil, Captex 200, Captex 355, Myglyol 812, and Myvacet 9-45), were evaluated. The solubility of MZ in each solvent medium was determined by adding excessive amount of MZ to the medium, followed by shaking at room temperature for at least 48 hours. After the equilibrium was reached, an aliquot was withdrawn and filtered through a membrane with a pore size of 0.45 µm. The clear filtrate was diluted with an appropriate volume of DMA and analyzed by the developed HPLC assay.

Development of Parenteral Formulations Using Co-Solvency Approach

One hundred milligrams of MZ were dissolved in 11 ml of DMA by warming in a 60.degree. water bath. The solution was then mixed with PEG 400 at ratios of 1:1 to 1:7 (v/v). A final portion of water was added to obtain a final co-solvent formulation with volume ratios of DMA:PEG 400:water at 2:2:1, 1:3:1, and 1:7:2. Using this approach, ten co-solvent systems of various compositions and ratios were evaluated and optimized to achieve the maximal drug solubility for parenteral delivery. The MZ solubility in individual co-solvent formulations was determined by the HPLC assay. The optimal formulation was selected to be administered intravenously (I.V.) as the most bioavailable formulation reference in the preclinical bioavailability study of the selected lead oral microemulsion formulation.

Development of Microemulsion Formulations

Six self-emulsifying drug delivery systems (SEDDS) were prepared by mixing an oil, a low HLB surfactant, and a high HLB surfactant. In particular, 100 mg of MZ were dissolved in 5.5 ml of DMSO or DMA at 60° C. in a water bath. The solution was then mixed with Tween 80, Aralacel 80, and various types of oils at different ratios.

A clear, transparent formulation was indicative of the formation of a stable microemulsion. Phase diagrams were constructed with six different ratios of the ingredients for each system, by adding a small increment of an aqueous phase (deionized water) to the SEDDS until the system became turbid, reflecting a phase separation, to define the boundary of the composition region for stable microemulsions.

Once the region of stable microemulsions was identified on the phase diagram, microemulsions were prepared by mixing appropriate quantities of the four ingredients (oil, dipolar aprotic solvent, surfactant, and water) with a gentle hand shaking or stirring to ensure a through mixing. MZ, either dissolved in DMA or DMSO, was incorporated by mixing with the other ingredients.

Two optimal microemulsion formulations were selected for further assessment of in vitro drug release. One of the two optimal formulations was evaluated for cell growth inhibition in cell culture models, and for in vivo preclinical bioavailability in rats. The lead microemulsion formulation will be suitable for future evaluation of anti-neoplastic efficacy in mice as well.

Determination of Drug Release

The drug release characteristics of the two selected SEDDS formulation were comparatively evaluated with MZ powder and MZ solution in PEG 400. All four formulations were filled manually with a syringe into a hydrophilic airfill soft gelatin capsule (R. P. Scherer, Basking Ridge, N.J.) and the resulting hole was sealed thermally. USP XXII, Dissolution Apparatus 2 (VanKel Industrial, Inc.) was employed to characterize the release kinetics of MZ in vitro. Soft gelatin capsules containing the SEDDS, MZ solution, or MZ powder were individually placed in copper coils to keep the capsules at the bottom of their respective dissolution vessels. The vessels were filled with 500 mL of deionized water containing 0.5% Cremphor RH 40 (CMC=0.039%) at 37.degree. C. Cremphor RH 40 was used to maintain the sink condition of the releasing medium. The release medium was constantly stirred at 50 rpm by a Teflon-coated dissolution paddle. Serial release samples were withdrawn and filtered through a 0.45 µm Millipore filter and analyzed by the HPLC assay.

Studies of Cell Growth Inhibition in NSCLC and Skin Cancer Cells Using Formulation E4 and Placebo Cells were plated in 96-well plates at $5 \times 10^6$ cells/ml of Dulbecco's modified Eagle's medium (DMEM) containing 100 U/ml penicillin, 100 .mu.g/ml streptomycin, and 10% fetal serum albumin, and incubated at 37° C. in a 5% $CO_2$/95% air-humidified incubator for 24 hrs. Cells were incubated for 48 hours after a medium change with fresh DMEM containing serial dilutions of E4 formulation or placebo. Cell survival was monitored with MTT assay. Anti-tumor effects of MZ were also evaluated using cell viability assays (trypan blue counting).

EXAMPLE 2

Preclinical Bioavailability of Microemulsion E4

Animals

Male Sprague-Dawley rats (Harlan Sprague Dawley, Inc., Indianapolis, Id.), weighing 300-400 g, were used after a 7-day acclimation period. Animals were housed under a 12 h light/dark cycle. A permanent catheter was implanted in the right jugular vein of each rat on the day before the study, under the anesthesia with ketamine:acetopromazine:xylazine (50:3.3:3.3 mg/kg). Animals were fasted overnight, while water was allowed ad libitum. On the morning of the experiment, rats were placed in individual metabolism cages.

Dosage Forms

The rats were randomized into three groups of three or four each. Rats in Group 1 were injected intravenously through the jugular catheter with a single dose (3.25 mg/kg) of the P7 formulation in a cosolvent system. Group 2 received oral microemulsion formulation E4; at a single dose of 5 mg/kg by oral gavage using an animal feeding needle (18×3"W/2¼ mm Ball). Group 3 were dosed with MZ aqueous unformulated suspension at 50 mg/kg similarly by oral gavage. The MZ suspension was prepared at 10 mg/ml with a trace amount of glycerin as a wetting agent.

Blood Sampling

Serial blood samples approximately 0.6 ml each were collected in heparinized tube through the catheter at determined time intervals for up to 24 hours. The blood samples were immediately centrifuged at 14,000 rpm for 3 min and the supernatant, plasma, was transferred into a 1.7-ml microcentrifuge tube and immediately stored at −80° C. until the HPLC assay.

HPLC Assay of Plasma Samples

MZ concentrations in plasma samples were determined by the HPLC method described in Example 1 with the following modifications. Briefly, 300 µl of plasma were mixed with 300 µl of acetonitrile to precipitate proteins. The acetonitrile contained 2 µg/mL quinidine (QD) as internal standard. Prednisone was not used as IS for plasma samples, because it was interfered by the broad solvent front from plasma blank. The mixture of plasma and acetonitrile was vortexed and centrifuged, then 100 µl of the supernatant were withdrawn and injected directly onto the HPLC system. The mobile phase consisted of 35% (v/v) acetonitrile in 0.05 M aqueous solution of $KH_2PO_4$, pH 6.5. The flow rate was 1.2 ml/min, and the effluent was monitored at 313 nm (0.01 AUFS).

Pharmacokinetic Analysis

Pharmacokinetic parameters were determined by fitting the plasma concentration-time data for each rat by a WinNonlin program. The maximum (peak) concentrations and the time to achieve maximum concentrations (peak time) in plasma were determined from the computer fitted plot. Areas under the concentration vs. time profiles from 0 to the last time point (720 min) of the measured concentration ($AUC_{0 \to 720}$) was determined by the linear trapezoidal rule, and the AUC from the time of the last measured concentration to infinity ($AUC_{720 \to infin.}$) was determined by dividing the last determined concentration by the terminal phase elimination rate constant, which was initially estimated from the least squares slope of the terminal linear segment of the plot. The terminal phase half-life was calculated as 0.693 divided by the terminal phase elimination rate constant. Other non-compartmental pharmacokinetic parameters were generated by area/moment analysis. Total plasma clearance (CLT) was calculated from Dose/AUC, mean residence time (MRT) was calculated from AUMC/AUC, and steady-state volume of distribution ($V_{ss}$) was calculated from [(Dose AUMC)/$AUC^2$]. For oral administration, bioavailability (F) was determined by the following equation:

$$F=[AUC_{oral}/AUC_{iv}] \times [Dose_{iv}/Dose_{oral}] \times 100\%$$

Statistical Analysis

Differences between any two mean values were statistically evaluated using paired or unpaired Student's t-test subsequent to statistical verification that the associated variances were homogeneous or equal.

EXAMPLE 3

HPLC Assay of MZ

The retention times of MZ and the IS (prednisone) were 9.3 min and 5.6 min, respectively, under the HPLC eluting conditions aforementioned in Example 1. In particular, the stationary phase was a $C_{18}$ column, 300×3.9 mm (Waters Corp.), the mobile phase was acetonitrile/0.05 M $KH_2PO_4$ (40:60 V.V; pH=6.5), the flow rate was 1.2 ml/min, the detection was UV at 254 nm, for integration a Milton Ray CI-4100 integrator was used. An authentic HPLC chromatogram of MZ is shown in FIG. 1. Standard curves of MZ were established in the concentration range of 0.05 µg/ml to 5.0 µg/ml.

For the assay modified for plasma samples, the retention time for MZ and the IS (QD) were 10 and 7 min, respectively. On each day of plasma sample assay, a calibration curve was constructed to calculate the MZ concentrations in plasma samples. The linearity of the curve was established in a MZ concentration range of 0.05 to 2.5 µg/ml, with $r^2 \geq 0.998$. The calibration curve was plotted with peak area ratio of MZ/QD versus the known MZ concentrations spiked in rat plasma blanks.

EXAMPLE 4

MZ Solubility in Various Solvent Media

The solubility of MZ in water and in the fourteen tested solvents at 25° C. are compiled in Table I.

TABLE I

| Solvent Medium | Solubility (µg/mL) | Enhancement Factor |
| --- | --- | --- |
| Water | 0.025 | 1 |
| Methanol | 55 | 2,200 |
| PEG 400 | 528 | 21,120 |
| Propylene glycol | 196 | 7,840 |
| Triacetin | 34.8 | 1,392 |
| DMA | 4,000 | 160,000 |
| DMSO | 5,000 | 200,000 |
| Super refined cottonseed oil | 0.251 | 0 |
| Olive oil | 19.7 | 788 |
| Super refined peanut oil | 0.25 | 10 |
| Super refined soybean oil | 5.8 | 232 |
| Captex 200 | 13.3 | 532 |
| Captex 355 | 1.2 | 48 |
| Miglyol 812 | 40.6 | 1,624 |
| Myvacet 9-45 | 39.3 | 1,572 |

MZ is poorly soluble in water with the solubility of 0.025 µg/mL. The MZ solubility in other solvent media, except super refined cottonseed oil, super refined peanut oil, and Captex 355, were all significantly higher than its aqueous solubility, with enhancement factors ranging from 232 to 200,000 in the reference to MZ aqueous solubility.

The MZ was favorably soluble in the six pharmaceutical solvents (methanol, PEG 400, propylene glycol, triacetin, DMA, and DMSO) with enhancement factors of 1,392 to 200,000. PEG 400, DMA, and DMSO yielded the highest three solubilities among the six tested solvents. PEG 400 alone yielded a solubility of 0.528 mg/ml, still much lower than the target of 1.5 mg/mL.

DMA and DMSO freely dissolved MZ, but were not pharmaceutically acceptable to use as straight solvents. The $LD_{50}$ of these solvents in rodents are 3.1 gm/kg. intravenously and 7.92 gm/kg orally. The oral and parenteral pharmaceutical products so far approved by FDA contain no more than 40% of DMA or DMSO. Therefore, PEG 400, DMA, and DMSO were selected to formulate MZ parenteral co-solvent systems with various compositions and ratios.

The MZ solubilities in the remaining five oils (olive oil, super refined soybean oil, Captex 200, Miglyol 812, and Myvacet 9-45) were significantly higher than its aqueous solubility, with enhancement factors ranging from 232 to 1,624 (Table I). However, none of them alone could reach the target concentration of 1.5 mg/ml. All the five oils could be used to formulate MZ microemulsions.

EXAMPLE 5

Development of Parenteral Formulations: Co-Solvent Systems

Ten co-solvent systems, coded as P1-P10, containing PEG 400 and DMA or PEG 400 and DMSO with various ratios, were systematically evaluated for their capacity to dissolve MZ. The MZ solubility in individual co-solvent systems are tabulated in Table II.

TABLE II

| Formula Code | Composition (Ratio) | | | | MZ Solubility (mg/mL) | Comment |
| --- | --- | --- | --- | --- | --- | --- |
| | Solvent A | Solvent D | Solvent E | Water | | |
| P1 | 2 | 2 | 0 | 0 | 0.574 | Patent formula for Busulfan |
| P2 | 2 | 2 | 0 | 1 | 0.459 | Containing 40% of Solvent D |
| P3 | 3 | 1 | 0 | 0 | 2.284 | Optimal I.V. formulation with Solvent D |
| P4 | 3 | 1 | 0 | 1 | 1.827 | Containing 20% of Solvent D |
| P5 | 7 | 1 | 0 | 0 | 0.934 | |
| P6 | 7 | 1 | 0 | 2 | 0.747 | Containing 10% of Solvent D |
| P7* | 7 | 0 | 1 | 0 | 1.831 | Optimal I.V. formulation with Solvent E |

TABLE II-continued

| Formula | Composition (Ratio) | | | | MZ Solubility | |
|---|---|---|---|---|---|---|
| Code | Solvent A | Solvent D | Solvent E | Water | (mg/mL) | Comment |
| P8 | 7 | 0 | 1 | 2 | 1.440 | Containing 10% of Solvent E |
| P9 | 3 | 0 | 1 | 0 | 3.488 | |
| P10 | 3 | 0 | 1 | 1 | 2.790 | Containing 20% of Solvent E |

*The selected parenteral formulatio, P7

The developed parenteral formulations yielded MZ solubility in the range of 0.46-3.49 mg/ml, 18,360-139,520 times higher than its aqueous solubility. All the formulations except P2 yielded solubilities higher than that in straight PEG 400, in the range of 1.09-6.61 times the MZ solubility in PEG 400. Six among the ten formulations, P3, P4, P7, P8, P9 and P10, yielded MZ solubility higher than 1.44 mg/ml, and were considered promising and suitable for further in vitro and in vivo evaluations. Formulation P7 with MZ solubility of 1.83 mg/ml was selected for future in vivo bioavailability study, based on its lowest content of DMSO and thus the maximal safety among the six promising systems.

EXAMPLE 6

Development of Microemulsion Formulations: Determination of Ability to Incorporate Water Formulations Thirty-six microemulsions (A1-A6, B1-B-6, C1-C-6, D1-D6, E1-E6, and F1-F6) were formulated and their capacities to incorporate water and to dissolve MZ were evaluated. These systems contained an oil (super refined soybean oil, Captex 200, Miglyol 812, or Myvacet 9-45), a solvent (DMA or DMSO), a blend of a high HLB Surfactant Tween 80 and a low HLB Surfactant Arelacel 80 (in a ratio of 1:1 or 2:1), and an aqueous phase. Their compositions are given in Tables III-A-III-F. In these Tables, the following codes are used: J=super refined soybean oil; K=Captex 200; M=Miglyol 812; N=Myvacet 9-45; D=DMA; E=DMSO; O=Tween 80; P=Arelacel 80.

Figure 2:
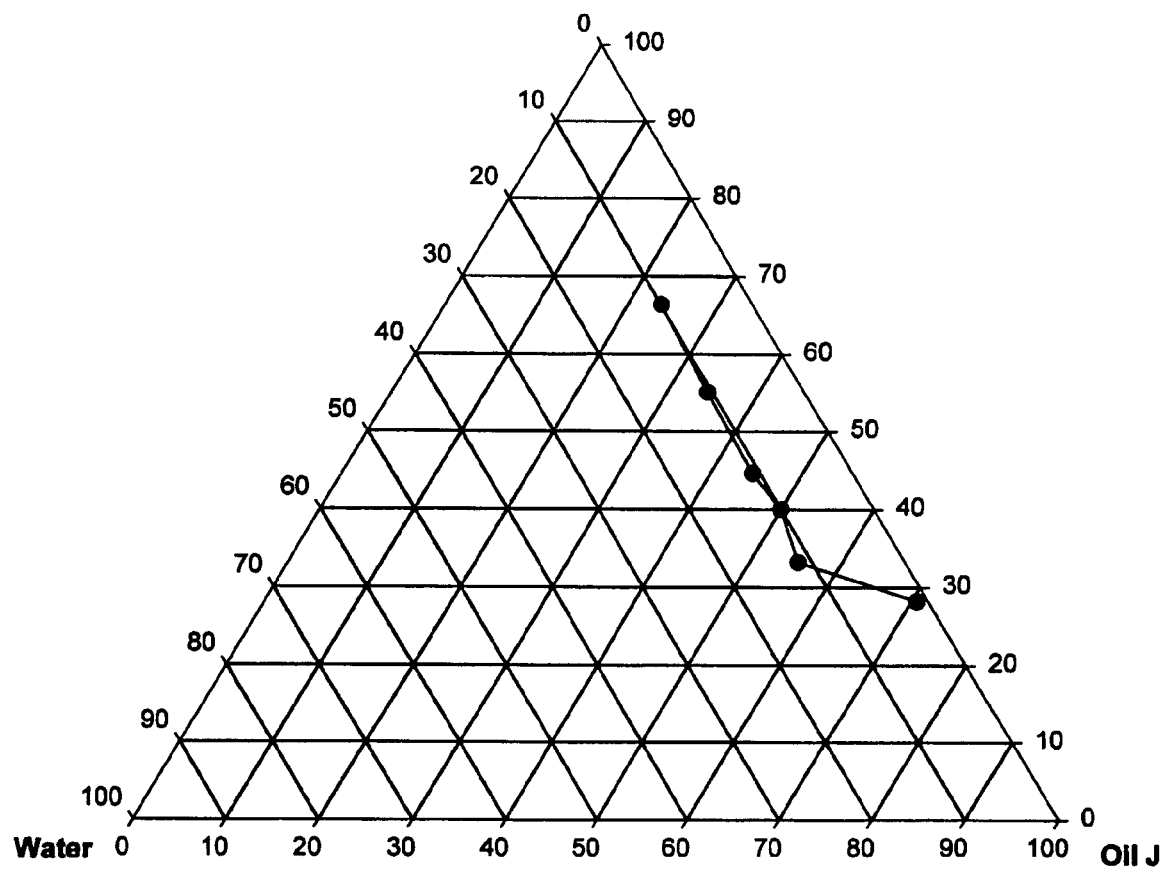
FIG. 2. Representative pseudo-ternary phase diagram of the microemulsion formulations described in Table III-E.

Among the formulated microemulsions, twenty-two formulations (A1-A3, B1-B3, $C_1$-$C_4$, D1-D4, E1-E4, and F1-F4) yielded MZ concentrations in the range of 1.5-2.64 mg/ml, meeting the target concentration of 1.5 mg/ml. When the maximum water that could be incorporated was taken into consideration, sixteen of the twenty-two microemulsion formulations, A3, B3, C1-C4, D3-D4, E1-E4, and F1-F4, that incorporated 10% (by weight) or higher of aqueous medium, were considered more stable than the rest formulations. Twelve microemulsions, $C_1$-$C_4$, E1-E4 and F1-F4 were the most promising formulations. Microemulsion E4 was selected for in vitro drug release and future in vivo studies of bioavailability and anti-neoplastic activity. In release study, formulation A4 was also comparatively evaluated. A representative pseudo-ternary phase diagram indicating the compositions of microemulsions E1-E6 is shown in FIG. 2.

TABLE III-A

| Formulation | Composition (% by Weight) | | | | | | | | | MZ |
| | Oil | | | | Solvent | | Surfactant | | $H_2O$ | Conc. |
| Code | J | K | M | N | D | E | O | P | Incorporation | HLB | (mg/mL) |
|---|---|---|---|---|---|---|---|---|---|---|---|
| A1 | — | 50.6 | — | — | 24 | — | 12.7 | 12.7 | 4 | 9.65 | 2.19 |
| A2 | — | 44.9 | — | — | 21.3 | — | 16.9 | 16.9 | 4.5 | 9.65 | 1.93 |
| A3 | — | 40.4 | — | — | 19.2 | — | 20.2 | 20.2 | 11 | 9.65 | 1.89 |
| A4 | — | 28.9 | — | — | 13.7 | — | 28.8 | 28.8 | 13 | 9.65 | 1.13 |
| A5 | — | 25.3 | — | — | 11.9 | — | 31.4 | 31.4 | 13 | 9.65 | 0.98 |
| A6 | — | 13.4 | — | — | 6.4 | — | 40.1 | 40.1 | 14 | 9.65 | 0.5 |

TABLE III-B

| Formulation | Composition (% by Weight) | | | | | | | | | MZ |
| | Oil | | | | Solvent | | Surfactant | | $H_2O$ | Conc. |
| Code | J | K | M | N | D | E | O | P | Incorporation | HLB | (mg/mL) |
|---|---|---|---|---|---|---|---|---|---|---|---|
| B1 | — | 47.9 | — | — | 22.8 | — | 16 | 8 | 5.3 | 11.4 | 2.25 |
| B2 | — | 41.9 | — | — | 19.9 | — | 20.9 | 10.6 | 6.7 | 11.4 | 2 |
| B3 | — | 36.2 | — | — | 17.2 | — | 24.1 | 12.1 | 10.3 | 11.4 | 1.8 |
| B4 | — | 24.8 | — | — | 11.8 | — | 33.1 | 16.5 | 13.9 | 11.4 | 1.29 |
| B5 | — | 24.4 | — | — | 11 | — | 32.5 | 16.3 | 15.9 | 11.4 | 1.3 |
| B6 | — | 11.1 | — | — | 5 | — | 46.5 | 23.3 | 14.1 | 11.4 | 0.58 |

TABLE III-C

| Formulation Code | Composition (% by Weight) | | | | | | | | H₂O Incorporation | HLB | MZ Conc. (mg/mL) |
|---|---|---|---|---|---|---|---|---|---|---|---|
| | Oil | | | | Solvent | | Surfactant | | | | |
| | J | K | M | N | D | E | O | P | | | |
| C1 | — | 50.1 | — | — | — | 12.6 | 12.6 | 12.6 | 12.1 | 9.65 | 2.64 |
| C2 | — | 42.6 | — | — | — | 10.7 | 16.1 | 16.1 | 14.5 | 9.65 | 2.31 |
| C3 | — | 38.4 | — | — | — | 9.6 | 19.2 | 19.2 | 13.6 | 9.65 | 2.06 |
| C4 | — | 34.7 | — | — | — | 8.7 | 21.7 | 21.7 | 13.2 | 9.65 | 1.85 |
| C5 | — | 26.5 | — | — | — | 6.7 | 26.7 | 26.7 | 13.4 | 9.65 | 1.42 |
| C6 | — | 17.2 | — | — | — | 4.3 | 32.5 | 32.5 | 13.5 | 9.65 | 0.92 |

TABLE III-D

| Formulation Code | Composition (% by Weight) | | | | | | | | H₂O Incorporation | HLB | MZ Conc. (mg/mL) |
|---|---|---|---|---|---|---|---|---|---|---|---|
| | Oil | | | | Solvent | | Surfactant | | | | |
| | J | K | M | N | D | E | O | P | | | |
| D1 | — | — | — | 50.6 | 24 | — | 12.7 | 12.7 | 0 | 9.65 | 2.25 |
| D2 | — | — | — | 44.9 | 21.3 | — | 16.9 | 16.9 | 0 | 9.65 | 2 |
| D3 | — | — | — | 36.4 | 17.3 | — | 18.2 | 18.2 | 9.9 | 9.65 | 1.8 |
| D4 | — | — | — | 33.1 | 15.6 | — | 20.7 | 20.7 | 9.9 | 9.65 | 1.64 |
| D5 | — | — | — | 25.5 | 12.1 | — | 25.5 | 25.5 | 11.4 | 9.65 | 1.29 |
| D6 | — | — | — | 16.9 | 8.1 | — | 31.4 | 31.4 | 12.2 | 9.65 | 0.87 |

TABLE III-E

| Formulation Code | Composition (% by Weight) | | | | | | | | H₂O Incorporation | HLB | MZ Conc. (mg/mL) |
|---|---|---|---|---|---|---|---|---|---|---|---|
| | Oil | | | | Solvent | | Surfactant | | | | |
| | J | K | M | N | D | E | O | P | | | |
| E1 | 56.5 | — | — | — | — | 14.1 | 14.1 | 14.1 | 1.2 | 9.65 | 2.14 |
| E2 | 44.2 | — | — | — | — | 11.1 | 16.6 | 16.6 | 11.5 | 9.65 | 1.88 |
| E3 | 40 | — | — | — | — | 10 | 20 | 20 | 10 | 9.65 | 1.87 |
| E4 | 35.7 | — | — | — | — | 8.9 | 22.3 | 22.3 | 10.8 | 9.65 | 1.8 |
| E5 | 27.4 | — | — | — | — | 6.9 | 27.6 | 27.6 | 10.5 | 9.65 | 1.15 |
| E6 | 19 | — | — | — | — | 4.7 | 33.2 | 33.2 | 9.9 | 9.65 | 0.79 |

*The selected Formulation E4 comprised of Oil J:Solvent E:Surfactant O:Surfactant P = 2 g:0.5 mL:1.25 g:1.25 g

TABLE III-F

| Formulation Code | Composition (% by Weight) | | | | | | | | H₂O Incorporation | HLB | MZ Conc. (mg/mL) |
|---|---|---|---|---|---|---|---|---|---|---|---|
| | Oil | | | | Solvent | | Surfactant | | | | |
| | J | K | M | N | D | E | O | P | | | |
| F1 | — | — | 50.4 | — | — | 12.6 | 12.7 | 12.7 | 11.6 | 9.65 | 2.14 |
| F2 | — | — | 42.4 | — | — | 10.6 | 15.9 | 15.9 | 15.2 | 9.65 | 1.88 |
| F3 | — | — | 39.2 | — | — | 9.8 | 19.6 | 19.6 | 11.8 | 9.65 | 1.67 |
| F4 | — | — | 34.7 | — | — | 8.7 | 21.8 | 21.8 | 13 | 9.65 | 1.5 |
| F5 | — | — | 27.2 | — | — | 6.8 | 27.3 | 27.3 | 11.4 | 9.65 | 1.15 |
| F6 | — | — | 18.4 | — | — | 4.6 | 32.8 | 32.8 | 11.4 | 9.65 | 0.78 |

MZ Release from Microemulsions A4 and E4

Figure 3:
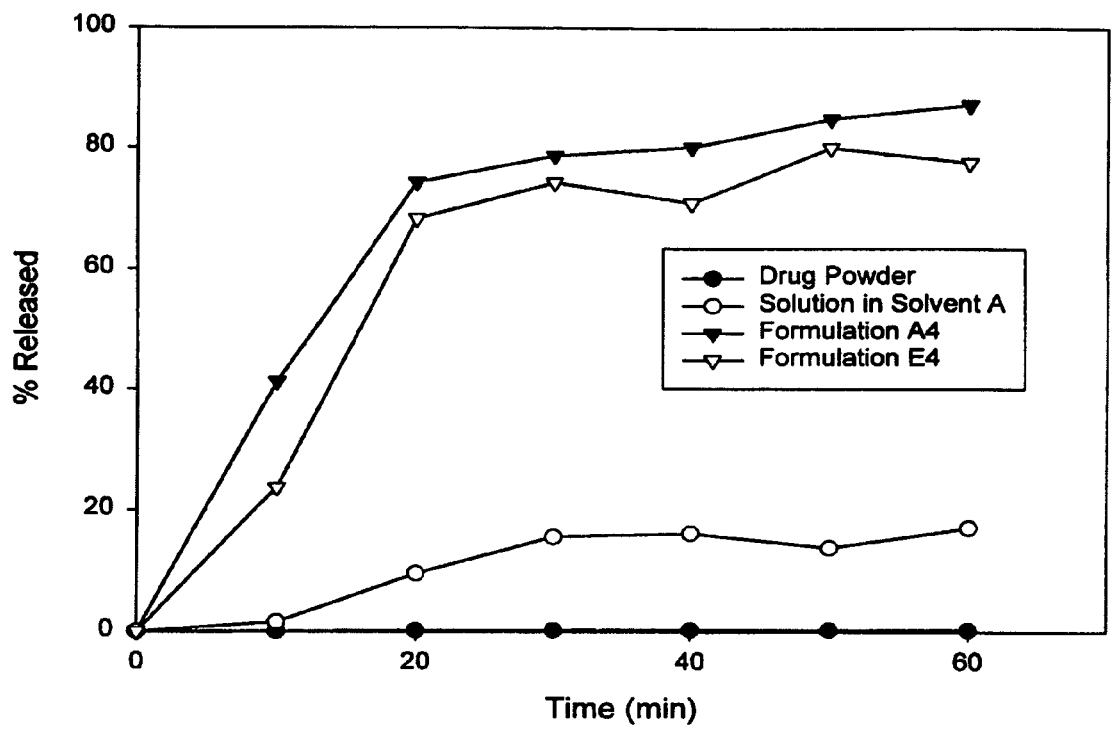
FIG. 3. In vitro release of MZ from microemulsion of formula codes A4 and E4.

The comparative in vitro release kinetics of MZ from drug powder, solution in PEG 400, microemulsion A4 (containing DMA), and microemulsion E4 (the selected oral formulation, containing DMSO), respectively, were evaluated and summarized in Table IV. The cumulative release profiles are presented in FIG. 3. MZ was readily released from the microemulsions A4 and E4, with 78.7% and 74.2%, respectively, dissolved in 30 minutes, greatly enhanced as compared with that of unformulated drug powder, 0.3% in 60 minutes. The MZ solution in PEG 400 was precipitated when in contact with the release medium after the capsule shell was disintegrated. The MZ dissolved slowly thereafter, and reached 17.1% dissolved in 60 minutes (Table IV).

TABLE IV

| Time (min) | MZ powder | Mean (SD) | MZ in PEG | Mean (SD) | Formulation A4* | Mean (SD) | Formulation E4** | Mean (SD) |
|---|---|---|---|---|---|---|---|---|
| | | | | Cumulative MZ Released (% Dose) | | | | |
| 10 | 0.01 | | 0.86 | | 3.9 | | 0.48 | |
| | 0.012 | | 1.1 | | 60 | | 26.7 | |
| | 0.083 | 0.04 | 2.7 | 1.55 | 59.8 | 41.23 | 43.9 | 23.69 |
| | | (0.04) | | (1.00) | | (32.33) | | (21.87) |
| 20 | 0.035 | | 9.0 | | 76.8 | | 72.2 | |
| | 0.22 | | 9.7 | | 67 | | 61.3 | |
| | 0.18 | 0.15 | 9.9 | 9.53 | 78.8 | 74.20 | 71.1 | 68.20 |
| | | (0.10) | | (0.47) | | (6.32) | | (6.00) |
| 30 | 0.14 | | 20.9 | | 74.9 | | 67.6 | |
| | 0.25 | | 10.2 | | 83.4 | | 74.3 | |
| | 0.28 | 0.22 | — | 15.56 | 77.7 | 78.67 | 80.8 | 74.23 |
| | | (0.07) | | (7.57) | | (4.33) | | (6.60) |
| 40 | 0.22 | | 24.3 | | 82.3 | | 71.0 | |
| | 0.23 | | 12.2 | | 78 | | 72.5 | |
| | 0.41 | 0.29 | 12.1 | 16.20 | 80.4 | 80.23 | 69.3 | 70.93 |
| | | (0.11) | | (7.02) | | (2.16) | | (1.60) |
| 50 | 0.2 | | 22.7 | | — | | 85.1 | |
| | 0.31 | | 10.4 | | 80 | | 73.9 | |
| | 0.35 | 0.29 | 8.3 | 13.80 | 89.7 | 84.85 | 81.3 | 80.10 |
| | | (0.08) | | (7.78) | | (6.86) | | (5.70) |
| 60 | 0.27 | | 27.5 | | 98.1 | | 75.4 | |
| | 0.27 | | 11.3 | | 77 | | 79.4 | |
| | 0.32 | 0.29 | 12.5 | 17.10 | 86.4 | 87.17 | 78.0 | 77.60 |
| | | (0.03) | | (9.03) | | (10.57) | | (2.03) |

*A4 Formulation - Oil K:Solvent D:Surfactant O:Surfactant P = 2 g:1 mL:2 g:2 g
**E4 Formulation - Oil J:Solvent E:Surfactant O:Surfactant P = 2 g:0.5 mL:1.25 g:1.25 g Preclinical Bioavailability Evaluation of E4

Eleven rats were used for the preclinical bioavailability evaluations of the lead oral microemulsion formulation in three independent runs. The rats were randomly grouped into three treatment groups: (a) I.V. dose of 3.25 mg/kg, n=3, (b) oral E4 microemulsion dose of 4.89 mg/kg, n=4, and (c) oral suspension dose of 50 mg/kg, n=4 (Table V). Table VI shows the pharmacokinetic parameters of MZ from P7, E4 and oral suspension formulations in rats.

TABLE V

| Rat No | Route | Dosage Form | Weight (g) | Dose (mg/kg) | Cmax (ng/mL) | AUC$_{0-720}$ (ng min/mL) | Tmax (min) | t$_{1/2}$ (min) | Bioavail. (%) |
|---|---|---|---|---|---|---|---|---|---|
| M | IV | Co-solvent | 300 | 3.25 | 10849 | 733042 | — | 104 | |
| N | IV | Co-solvent | 320 | 3.25 | 13747 | 876594 | — | 77 | |
| O | IV | Co-solvent | 320 | 3.25 | 7699 | 914010 | — | 120 | |
| | | Mean ± SD | 313 ± 12 | 3.25 | 10765 ± 3025 | 841635 ± 95766 | | 100 ± 22 | |
| A | Oral | Microemulsion | 325 | 4.89 | 867 | 526350 | 240 | — | 41.6 |
| E | Oral | Microemulsion | 365 | 4.89 | 794 | 327660 | 240 | 127 | 25.9 |
| F | Oral | Microemulsion | 375 | 4.89 | 697 | 337680 | 240 | 231 | 26.7 |
| G | Oral | Microemulsion | 360 | 4.89 | 1064 | 354270 | 120 | 129 | 28.0 |
| | | Mean ± SD | 356 ± 22 | 4.89 | 856 ± 155 | 386490 ± 93883 | 210 ± 60 | 162 ± 59 | 30.6 ± 7.4 |
| C | Oral | Suspension | 303 | 50 | 154 | 42165 | 300 | 115 | 0.33 |
| H | Oral | Suspension | 345 | 50 | 138 | 38970 | 360 | 102 | 0.30 |
| I | Oral | Suspension | 370 | 50 | 168 | 64140 | 360 | 191 | 0.50 |
| J | Oral | Suspension | 380 | 50 | 63 | 14940 | 240 | — | 0.12 |
| | | Mean ± SD | 350 ± 34 | 50 | 131 ± 47 | 40054 ± 20137 | 315 ± 57 | 136 ± 48 | 0.31 ± 0.16 |

TABLE VI

| Time (min) | Plasma Concentration (ng/ml) | | | | | | | | | | |
|---|---|---|---|---|---|---|---|---|---|---|---|
| | IV | | | E4 | | | | Suspension | | | |
| | M | N | O | A | E | F | G | C | H | I | J |
| 0 | 10849 | 13747 | 7700 | 0 | 0 | 0 | 0 | 0 | 0 | 0 | 0 |
| 5 | | 13365 | 7191 | | | | | | | | |
| 7 | | | 9162 | | | | | | | | |
| 15 | | 7553 | 12633 | 6272 | | | | | | | |
| 30 | 4599 | 6527 | 4601 | 646 | 502 | 216 | 534 | | | | |
| 60 | 2539 | 2846 | 3430 | 562 | 490 | 310 | 854 | | 22 | 26 | 35 |
| 75 | | | | | | | | 14 | | | |
| 90 | 1848 | 2371 | 2664 | | | | | | | | |

TABLE VI-continued

| Time (min) | Plasma Concentration (ng/ml) | | | | | | | | | | |
|---|---|---|---|---|---|---|---|---|---|---|---|
| | IV | | | E4 | | | | Suspension | | | |
| | M | N | O | A | E | F | G | C | H | I | J |
| 120 | 1654 | 1924 | 2235 | 842 | 555 | 533 | 1064 | 26 | 13 | 58 | 52 |
| 180 | 1078 | 1362 | 1587 | | | | | 71 | | | |
| 240 | 781 | 842 | 1274 | 867 | 794 | 697 | 840 | | 64 | 90 | 63 |
| 300 | 469 | 371 | 789 | | | | | 154 | | | |
| 360 | | 187 | | 779 | 567 | 558 | 449 | | 138 | 168 | 10 |
| 480 | | | | 787 | 374 | 550 | 232 | 43 | | 60 | 116 |
| 720 | | | | 556 | 83 | 164 | | 12 | | 12 | 46 |

Figure 4:
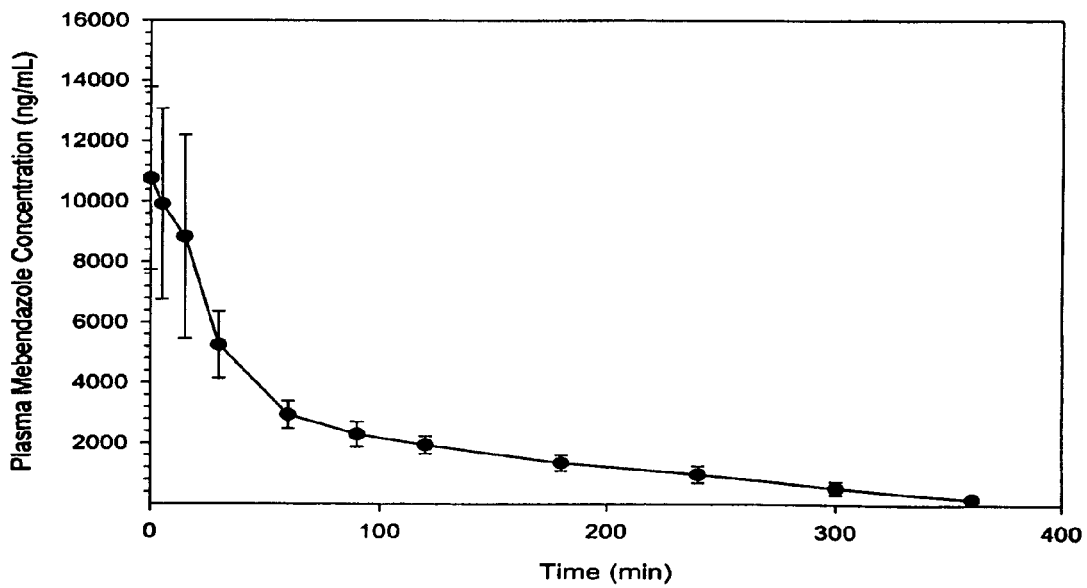
FIG. 4. Mean pharmacokinetic profile (n=3) of MZ after intravenous bolus administration of co-solvency formula P7 (3.25 mg/kg) to rats.
Figure 5:
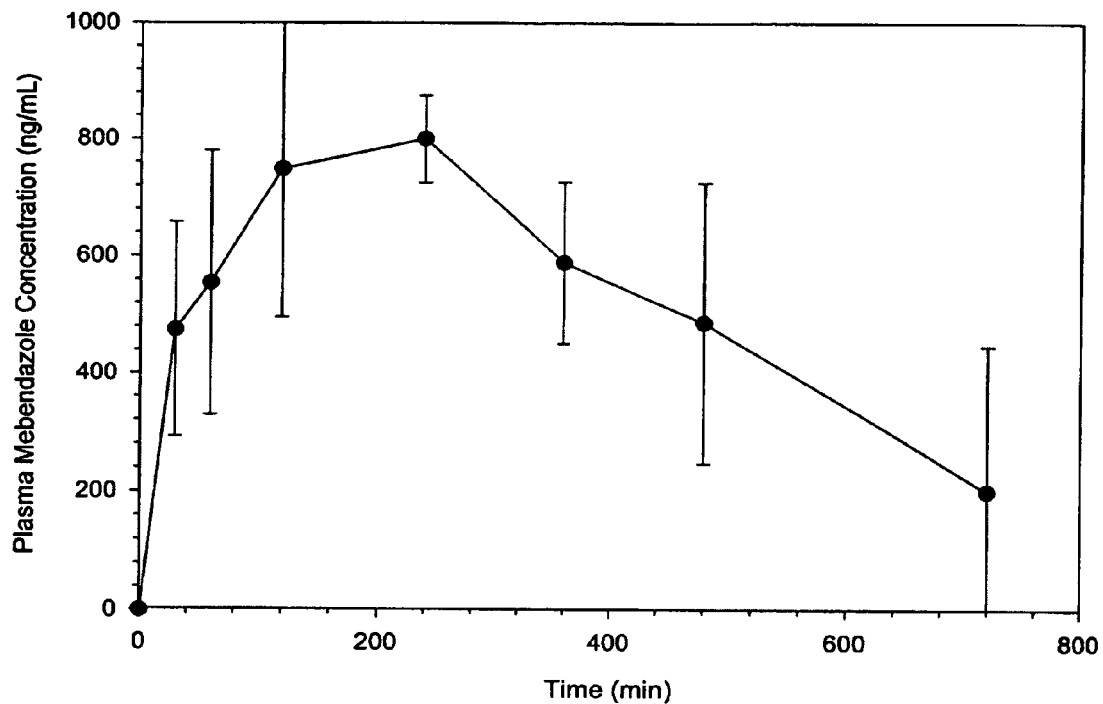
FIG. 5. Mean pharmacokinetic profile (n=4) of MZ after oral administration of microemulsion E4 (4.89 mg/kg) to rats.
Figure 6:
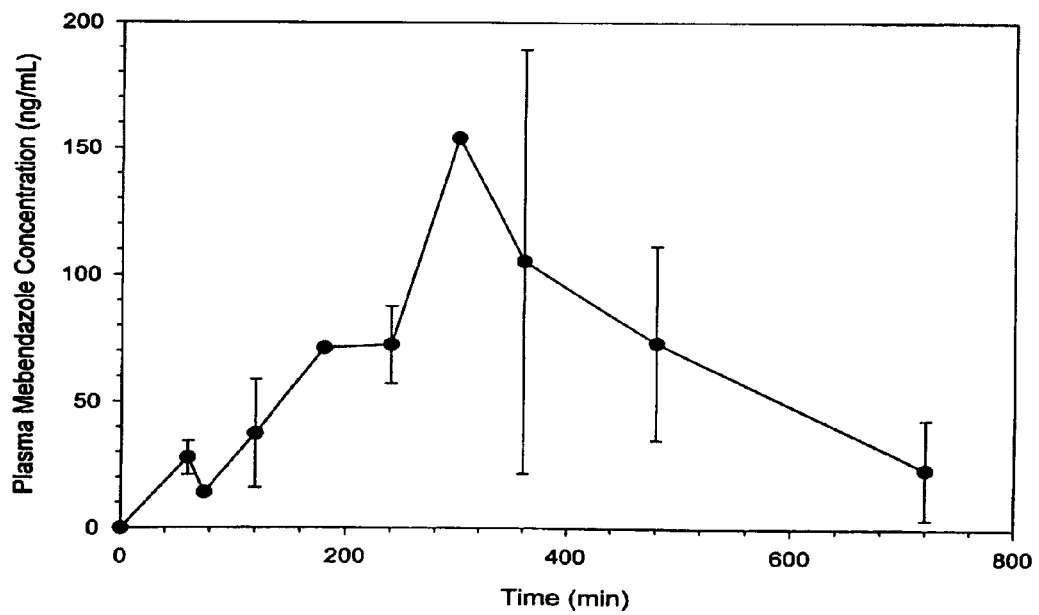
FIG. 6. Mean pharmacokinetic profile (n=4) of MZ after oral administration of suspension formulation (50 mg/kg) to rats.
Figure 7:
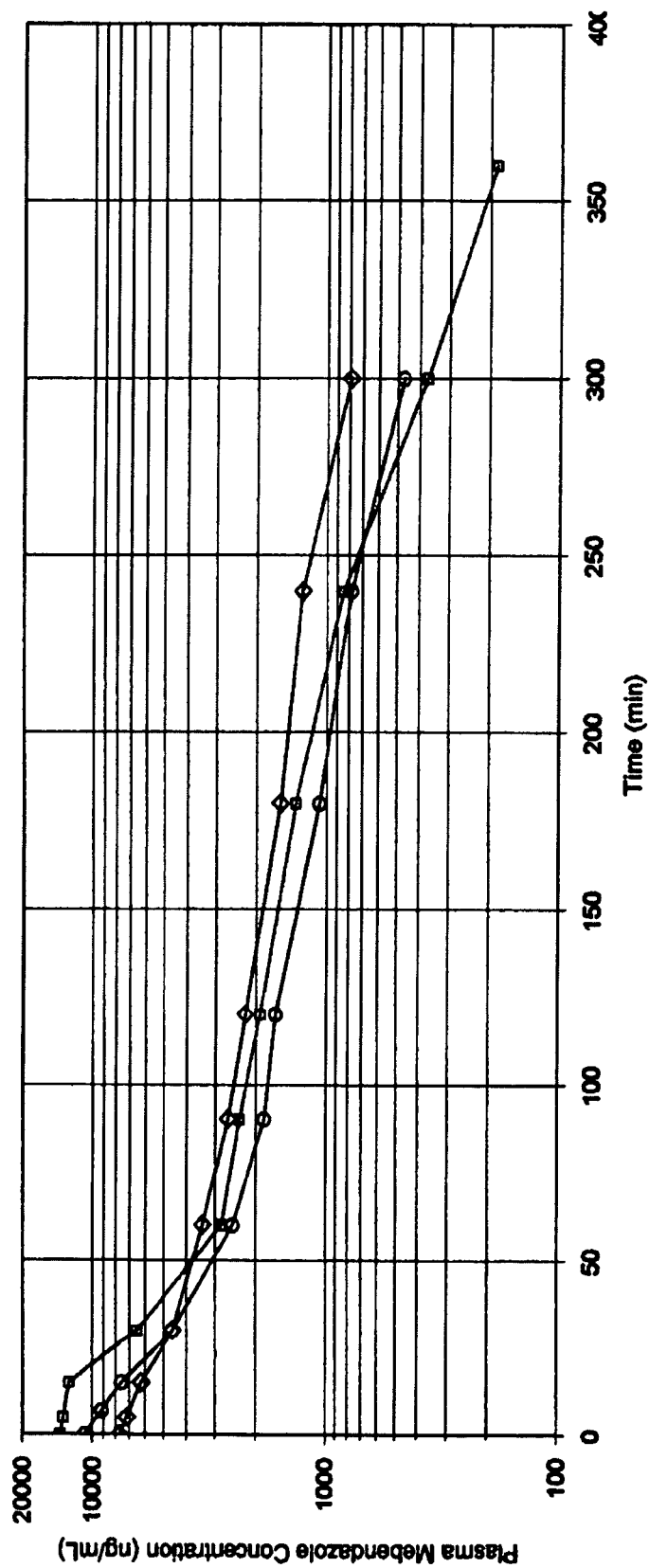
FIG. 7. Semi-logarithmic pharmacokinetic profiles of MZ after intravenous bolus administration of co-solvency formulation P7 (3.25 mg/kg) to rats.

The plasma-time profiles of MZ from I.V., E4 and unformulated suspensions were constructed. (FIGS. 4-6). The semi-log plot of the profiles of MZ after I.V. administration to individual rats (FIG. 7) were all bi-phasic with a rapid decline in mean concentrations from 7699 ng/ml to 2662 ng/ml within 90 min. The profile fitted a two-compartment model, indicating that the distribution of MZ in rats had a distinct tissue peripheral compartment. The distribution process appeared to be faster than the absorption process when MZ was given orally. The profiles of MZ from administrations of oral E4 and suspension did not exhibit any bi-phasic decline and fitted well into the typical 1-compartment model with an absorption process of first-order kinetics. The drug concentrations from suspension dosing (10-168 ng/ml) were substantial lower than those from E4 dosing (83-1064 ng/ml), even the suspension dose administered was 10 times higher.

The plasma profiles were analyzed by non-compartmental model with WinNonlin program to derive pharmacokinetic parameters for comparison. The MZ peak concentration from E4 was 856±155 ng/ml, 6.5 folds of that from suspension, 131±47 ng/ml. (Table V). The peak time from both dosing were comparable, 210±60 and 315±57 min, for E4 and suspension, respectively. The absorption half-lives were similar, 100±57 and 184±63 min, for E4 and suspension, respectively. The biological half-life was not statistically different from the different formulations (I.V. solution, E4 microemulsion and suspension) nor by the various routes of administration (I.V. and oral.), ranging from 100-162 min.

The systemic exposure of MZ after the different dosage forms were measured by $AUC_{0-720}$. When the values were normalized by the respective doses given, the absolute bioavailability of E4 and suspension in reference to I.V. dosing were 30.6% and 0.31%, respectively (Table V). The relative bioavailability of E4 in reference to the unformulated suspension was 98.7. It means that by formulating MZ into the microemulsion formulation, the bioequivalent dose of E4 was about {fraction (1/100)} of that of the unformulated suspension.

Cell Growth Inhibition in NSCLC and Skin Cancer Cell Lines

Figure 8:
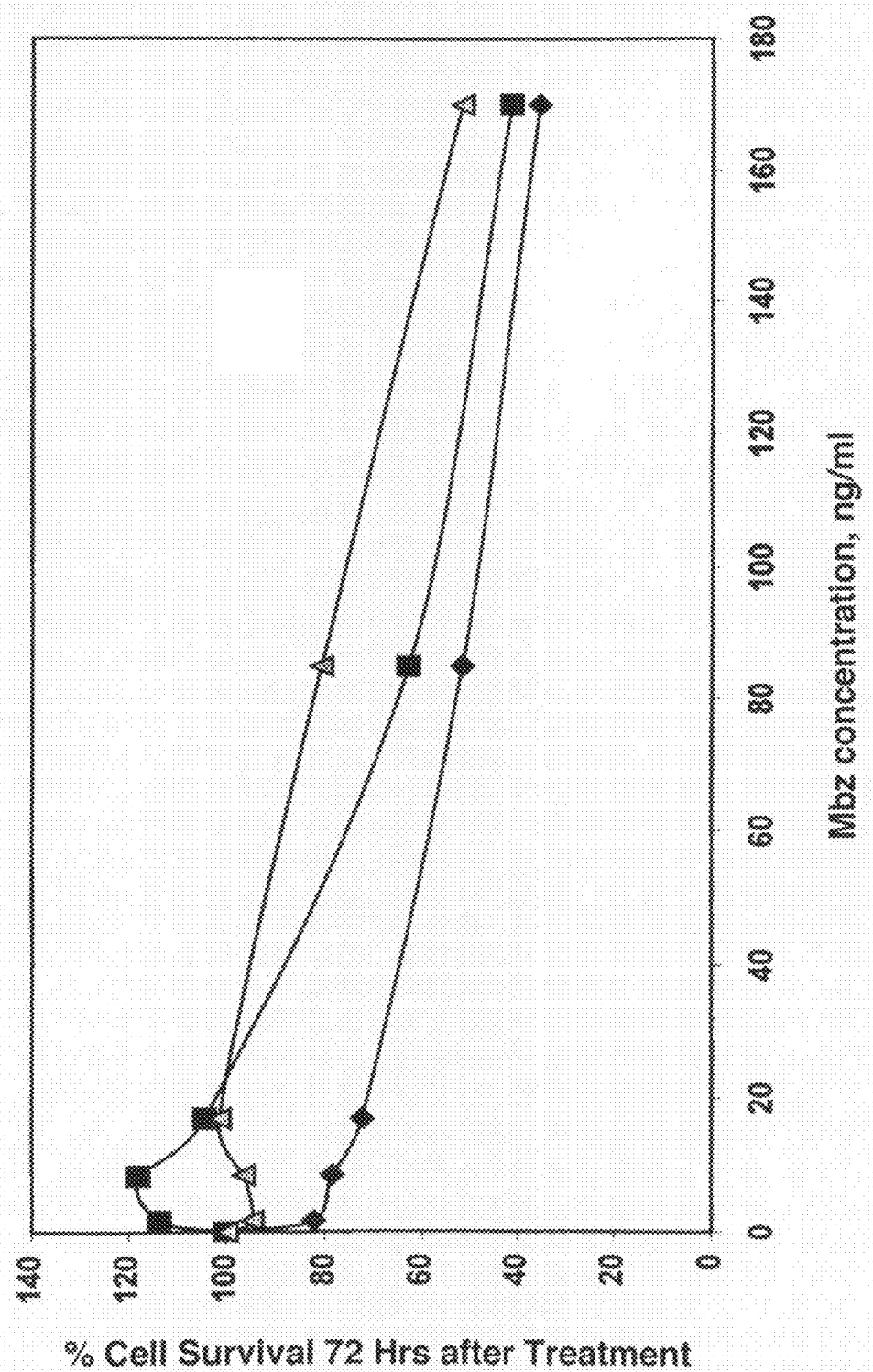
FIG. 8. Cytotoxicity of MZ E4-microemulsion in three skin cancer cell lines (SRB1, A375, 2237).
Figure 9:
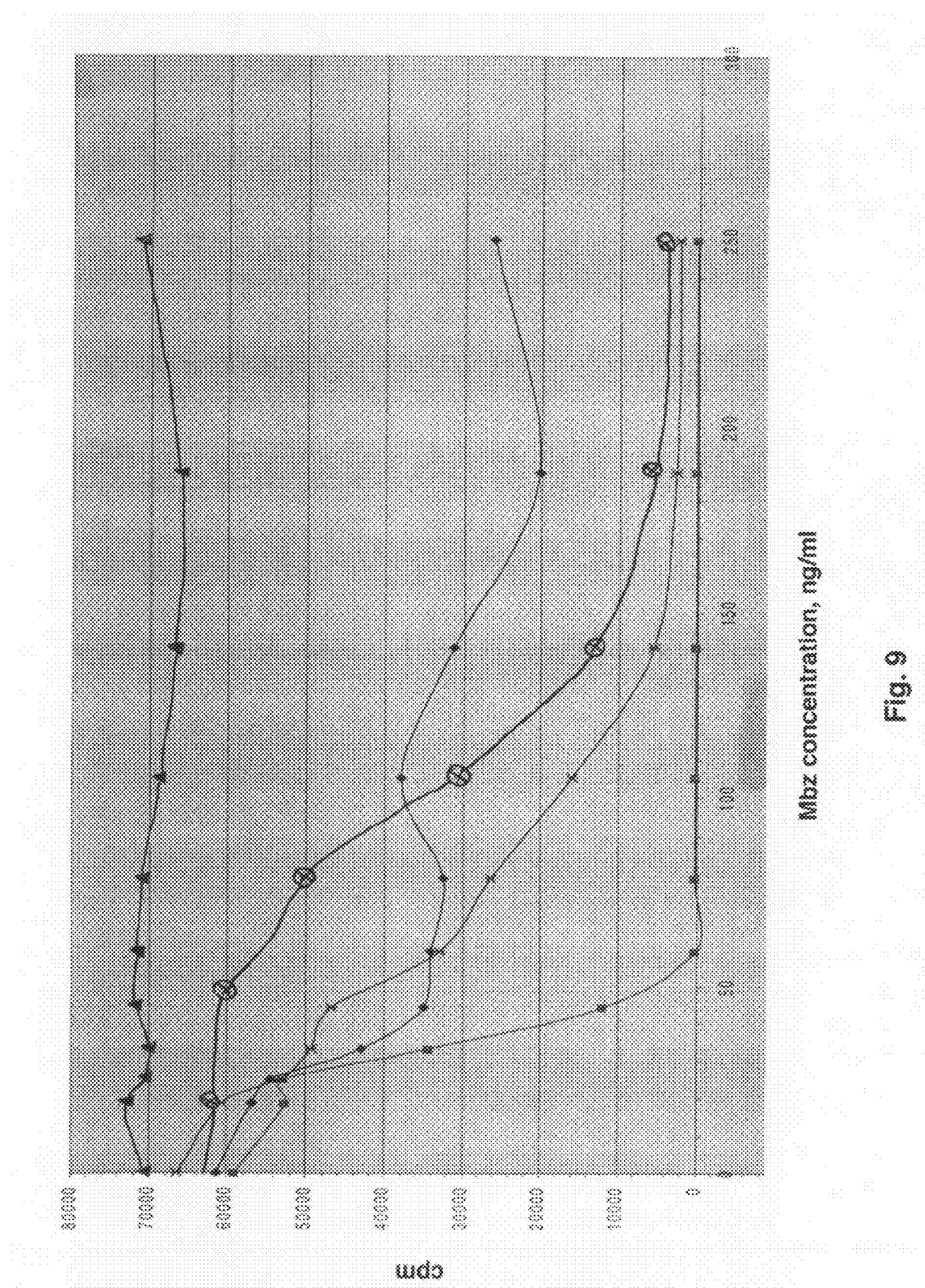
FIG. 9. Cell killing effects of MZ E4-microemulsion and MZ-DMSO versus placebos in H1299 cells.

The E4 formulation and placebo were used in studies of cell growth inhibition in skin cancer cell lines (SRB1, A375 and 2237) and non-small cell lung cancer (NSCLC) cell lines. The dose-response curves for cell growth inhibition were established for the range of 1.7-170 ng/ml for skin cancer cells (FIG. 8) and 2.5-250 ng/ml for NSCLC (FIG. 9). The IC.sub.50 of MZ in skin cancer cells was 91, 129, and 171 ng/ml for SRB1, A375, and 2237, respectively (FIG. 8). The IC.sub.50 of MZ from two microemulsion formulations in NSCLC cells was 8 and 10 ng/ml, respectively, which represented 8-9 fold enhancements, as compared with those of DMSO-dissolved MZ controls (FIG. 9). Thus, this study of enhanced anti-neoplastic activity in cultured cells provides evidence of the effective delivery of MZ by the E4 formulation. Thus, the developed microemulsion formulations exhibited favorable characteristics in drug release, preclinical efficacy in cultures, and preclinical pharmacokinetics in rats.

EXAMPLE 7

Optimized SNEDDS. SEDDS and Microemulsions for Parenteral Administration with Increased Bioavailability
Pre-Formulation Studies An HPLC assay for mebendazole was validated within the linear range of 0.02-10 μg/ml for both aqueous buffer and plasma samples. Mebendazole was identified to be a weak base, with log P of 2.51, belonging to Biopharmaceutical Classification Scheme II of drugs. Thus, for mebendazole, permeability is not a major factor limiting drug absorption; rather dissolution was identified to be the rate-limiting step for the systemic absorption of the drug. The pH-stability study indicated that the drug was sufficiently stable at room temperature in the pH range of 1-7, for a period of 33 days. Thus, no pH-related stability issues were identified for mebendazole that could limit drug absorption. The effective pH for the formulation of mebendazole was identified to lie in the range of 3-7.

Solubility of Mebendazole in Various Oils

The solubility of Mbz was determined in different vehicles and phase diagrams (FIGS. 10A-10B) constructed to define the microemulsion regions for selections of the lead SEDDS and SNEDDS. The solubilities of mebendazole in various natural and other oils are listed in Table VII and in various surfactants and cosurfactants in Table VIII. Oils and surfactants/cosurfactants selected for SNEDD and SEDD development are marked (*). Each value in Tables VII and VIII represents the mean±SD of three independent determinations.

TABLE VII

| Oil | Oil type | Solubility (μg/ml) |
|---|---|---|
| Super refined: | | |
| Cotton seed oil | Natural oil | 3.9 ± 0.1 |
| Sesame seed oil | Natural oil (*Sesamum Indicum*) | 1.7 ± 1.0 |
| Soybean oil | Natural oil (*Glycine soja*) | 5.8 ± 1.3* |
| Corn oil | Natural oil | 2.8 ± 0.5 |
| Peanut oil | Natural oil | 2.4 ± 0.9 |
| Shark liver oil | Natural oil | 6.1 ± 0.6 |
| Captex 200 | $C_8/C_{10}$ diesters of PG from coconut oil | 9.0 ± 0.9* |
| Myglyol | $C_8/C_{10}$ triglycerides from coconut oil | 15.2 ± 0.8* |
| Myvacet 9-45K | Distilled acetylated monoglyceride | 61.3 ± 1.2* |
| Olive oil | Natural oil | 2.7 ± 0.6 |
| Neobee M-5 | $C_8/C_{10}$ caprylic/capric triglyceride | 5.8 ± 1.4 |

TABLE VIII

| Surfactants/Cosurfactants (HLB) | S/CoS type | Solubility (μg/ml) |
|---|---|---|
| Labrafac CC (10.0) | Medium chain triglyceride EP ($C_8$-$C_{10}$ fatty acid) | 32.31 ± 5.0 |
| Labrasol (14.0) | Caprylocaproyl macrogol-8 glycerides | 605.53 ± 52.6* |
| Labrafil M 1944 CS (3-4) | Oleoyl macrogol-6 glycerides | 88.36 ± 32.4 |
| Labrafil M 2125 CS (3-4) | Linoleoyl macrogol-6 glycerides | 178.81 ± 22.6 |
| Aracel 80/Crill 4NF (4.3 | Sorbitan Oleate | 101.29 ± 2.0* |
| Capmul MCM (5.5-6.0) | $C_8$/$C_{10}$ mono-/diglyceride from coconut oil | 494.52 ± 60.4* |
| Cremophor RH 40 (14.0-16.0) | Polyoxyl 40 hydrogenated castor oil | 91.11 ± 31.6 |
| Cremophor EL (13.5) | Polyoxyethylenglycerol-triricinoleat | 346.51 ± 61.2* |
| Crillet 1-HP (16.7) | Polyoxyethylene (20) sorbitan monolaurate (Polysorbate 20) | 31.0 ± 5.1 |
| Crillet 4-HP (15.0) | Polyoxyethylene (80) sorbitan monolaurate (Polysorbate 80) | 370.18 ± 49.2* |
| Centrophase 152 | Soy lecithin (Mixed phospholipids) | 95.44 ± 4.6 |
| Triacetin | 1,2,3-propanetriol/glyceryl-triacetate/triacetyl glycerol | 54.44 ± 5.12 |
| Transcutol P | Diethylene glycol monoethyl ether | 299.1 ± 9.57* |

Figure 10A:
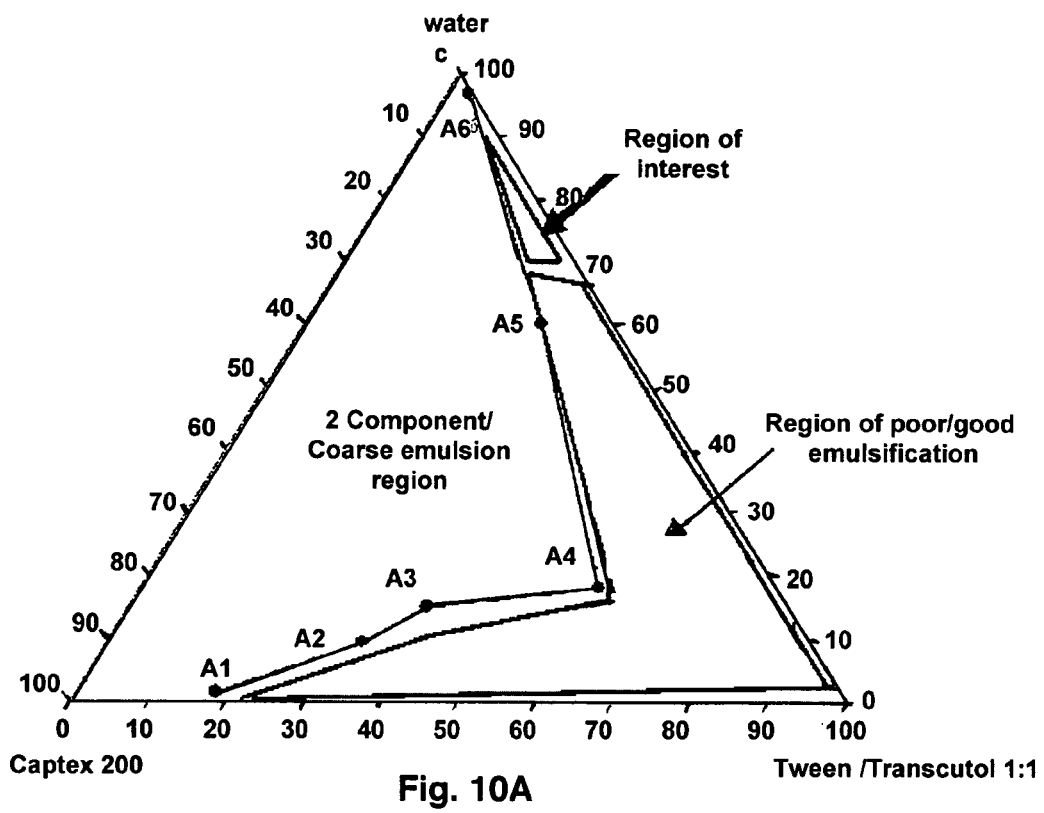
FIGS. 10A-10B. Representative pseudo-ternary phase diagrams for SNEDDs with captex 200/1:1 tween/transcutol/water (FIG. 10A) and myglyol/1:1 tween/transcutol/water (FIG. 10B) combinations.

FIG. 10A is a pseudo-ternary phase diagram for SNEDDs using a surfactant/cosurfactant combination. Points A1-A6, represent the different weight compositions of surfactant, cosurfactant, oil and water incorporated in the formulation to delineate the regions of microemulsion existence. The line joining the points A1-A6 is the boundary line. The area above the boundary line represents the region of phase separation, and the area below the line is the region of microemulsion existence. Various compositions were evaluated within the cordoned area of microemulsion existence to determine the region of efficient emulsification. Compositions marked under "region of interest" were those having a high efficiency of emulsification and can be diluted to maximum amounts of water without drug precipitation or phase separation. Compositions marked under the "region of interest" were then optimized to find the formulate Type IIIB system/SNEDDS with a droplet size of <50 nm and a targeted drug solubility of 1.96 mg/ml.

Figure 10B:
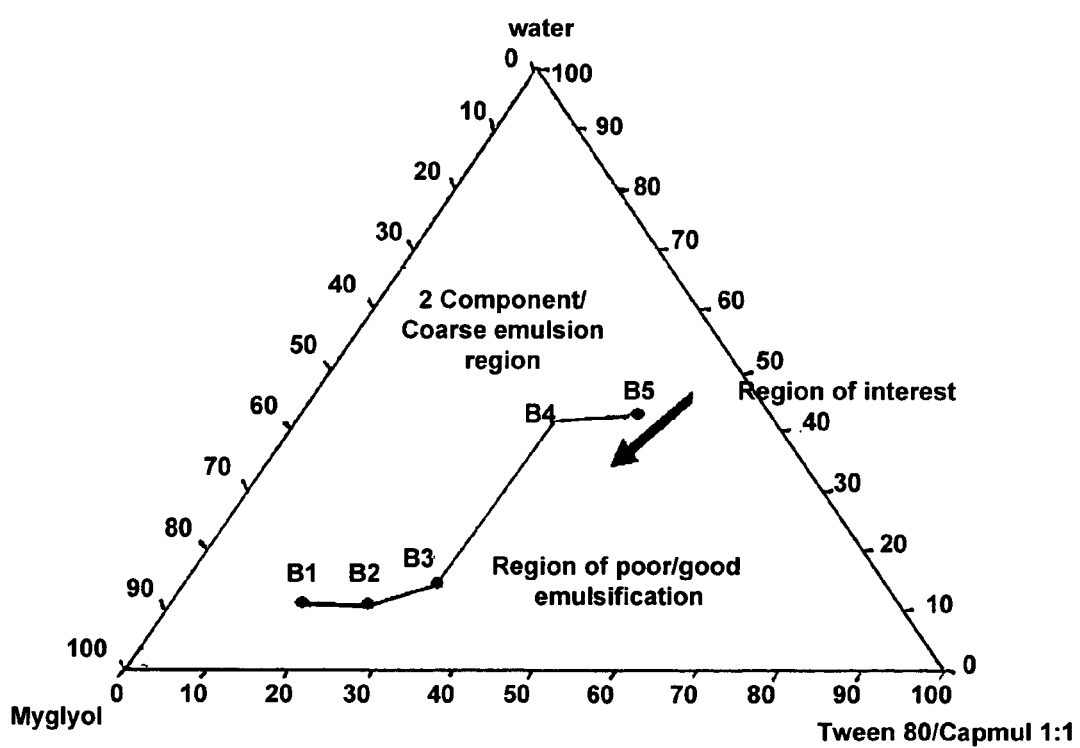

FIG. 10B is a pseudo-ternary phase diagram for SNEDDs using a high/low HLB surfactants combination. Points B1-B5, represent the different weight compositions of surfactant, cosurfactant, oil and water incorporated in the formulation to delineate the regions of microemulsion existence. The line joining the points B1-B5 is the boundary line. The area above the boundary line represents the region of phase separation, and the area below the line is the region of microemulsion existence. Various compositions were evaluated within the cordoned area of microemulsion existence to determine the region of efficient emulsification. Compositions marked under "region of interest" were those having a high efficiency of emulsification and can be diluted to maximum amounts of water without drug precipitation or phase separation. Compositions marked under the "region of interest" were then optimized to find the formulate Type II system/SEDDS with a droplet size of <200 nm and a targeted drug solubility of 1.96 mg/ml.

Table IX lists formulations or compositions for SNEEDs, SEDDs and parenteral microemulsions (PMs) utilizing the selected oils, surfactants and cosurfactants.

TABLE IX

|  | SNEDDS | SEDDS | PM-1 | PM-2 |
|---|---|---|---|---|
| Size (nm) | 35 | 143 | 37 | 478 |
| Drug conc. (mg/ml) | 1.96 | 1.96 | 0.95 | 0.95 |
| Compositions (% w/w) |  |  |  |  |
| Captex 200 (oil) | 9.0 | — | 4.5 | 18.0 |
| Myglyol (MCT) (oil) | — | 42.0 | — | — |
| Tween 80 (surfactant) | 40.5 | 27 | 20.25 | 13.5 |
| Capmul (cosurfactant) | — | 21 | — | — |
| Transcutol (cosurfactant) | 40.5 | — | 20.25 | 13.5 |
| DMSO (vehicle) | 10.0 | 10.0 | 5.0 | 5.0 |
| Water | — | — | 50.0 | 50.0 |

Captex 200/Tween 80/Transcutol and Myglyol/Tween 80/Capmul MCM systems led to the formation of efficient SNEDDS and SEDDS, respectively, that resulted in a high efficiency of emulsification and could be diluted with water to the maximum extents without phase separations. No change in the droplet size was observed at 10% w/w of mebendazole in the formulated SNEDDS and SEDDS, with mean droplet diameters of 34.8±2.1 nm and 143.0±2.0 nm and, respectively, which were similar to the droplet sizes of the placebo formulations.

Mebendazole Release Profiles

Figure 11A:
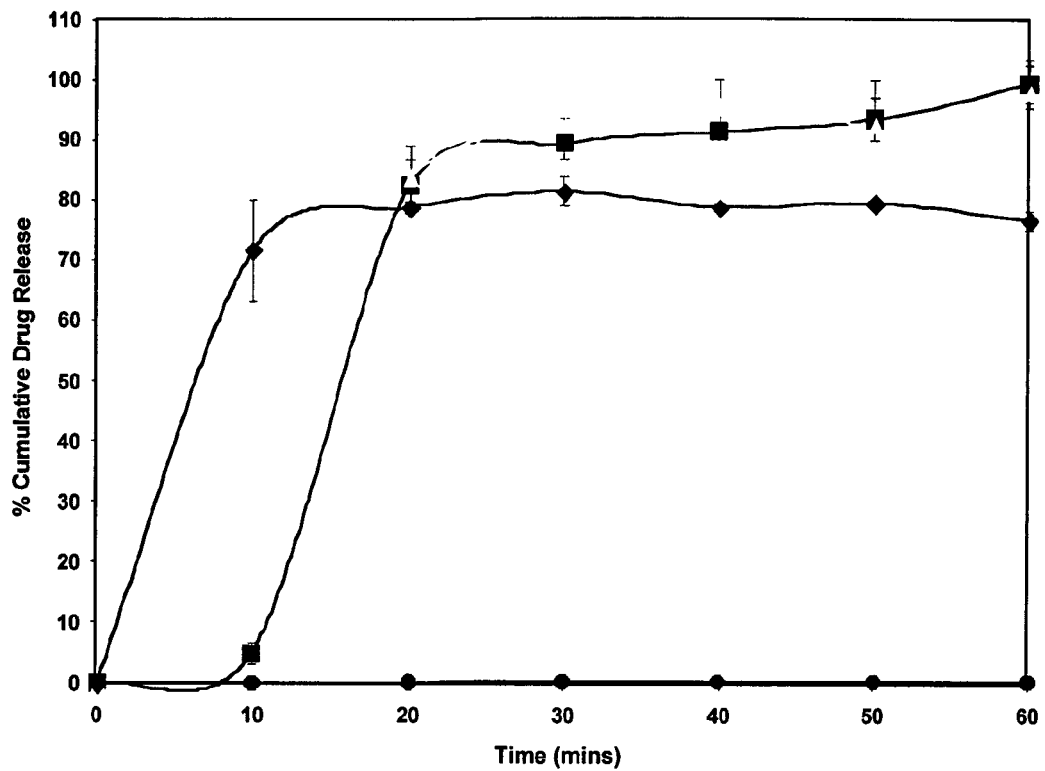
FIGS. 11A-11B. Comparative release profiles of mebendazole from SNEDDs (−▲−), SEDDS (−■−), cosolvent formulations (−◆−), and unformulated suspensions (−●−) (FIG. 11A) and from unformulated suspension and unformatted drug in media with placebo SNEDDs (−▲−) (FIG. 11B).

The rates of drug release was rapid, 0.053±0.002% $min^{-1}$ and 0.078±0.004% $min^{-1}$ for the SNEDDS and SEDDS, respectively, which were significantly greater than that of the unformulated suspension, 0.004±0.001% $min^{-1}$. Mebendazole was readily released from SNEDDs and SEDDs with 92.4 and 89.4% of drug released in 30 minutes, respectively, compared to 79.6 and 0.30% of drug release in 60 minutes from the co-solvent and unformulated suspension, respectively (FIG. 11A). Each point represents the mean±SD of three independent determinations. The release profiles of the SNEDDS and SEDDS were similar to each other.

Figure 11B:
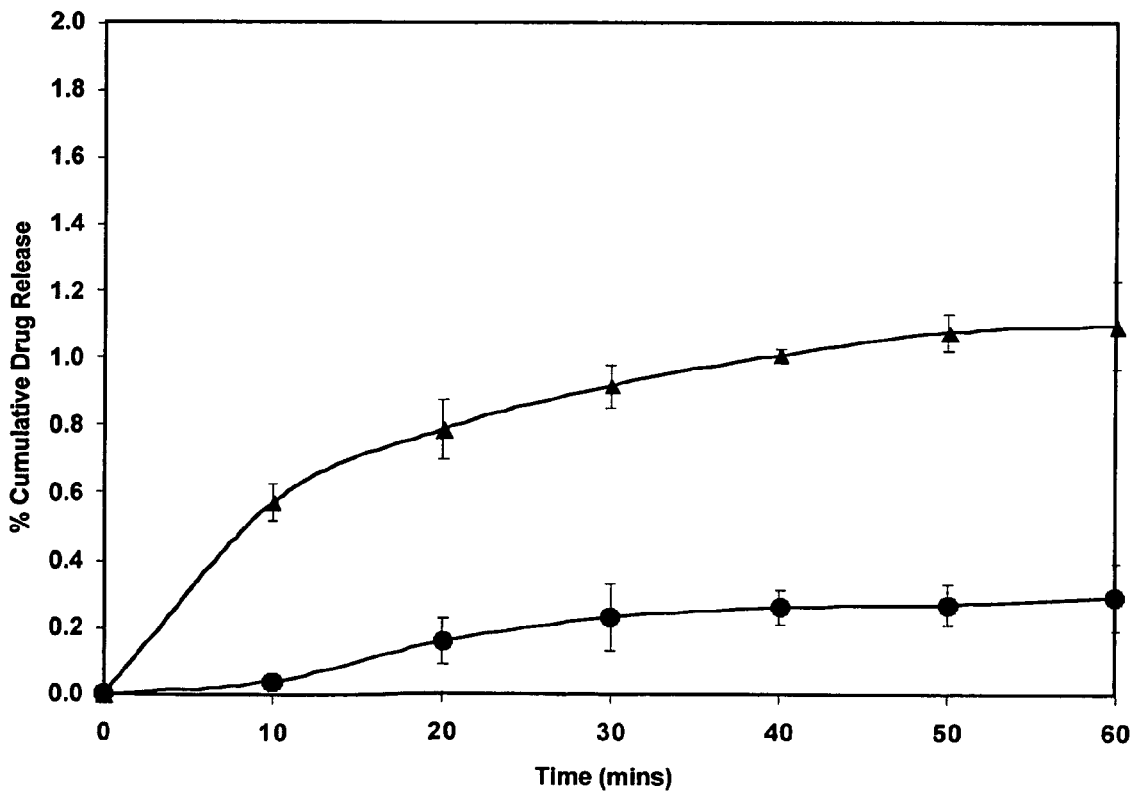

The extent of drug release from unformulated suspension in release media and unformulated drug in release media with placebo SNEDDS was 0.30% and 1.10%, respectively, at the end of 60 minutes (FIG. 11B). Each point represents the mean±SD of three independent determinations. The presence of placebo SNEDDS in the dissolution medium did not significantly enhance the rate or the extent of dissolution mebendazole to the extents of increase that were obtained from the SNEDDS and SEDDS. Therefore, the effects of wetting agent, glycerin, and the placebo SNEDDS cannot be accounted for the extents of increases of mebendazole dissolution from the SEDDS and SNEDDS. Hence, the enhanced dissolution observed with the SEDDS and SNEDDS is a formulation effect and not a solvent effect.

The extents of free drug released after 60 minutes were 77.9±3.6% and 74.7±9.4% from SNEDDS and SEDDS, respectively. The free drug molecules constitute 79.4% and 75.2% of the total released mebendazole, 98.1 and 99.4%, from SNEDDS and SEDDS, respectively (data not shown). Therefore, the majority of the drug molecules that were released from the SNEDDS and SEDDS were present in the free form.

Table X lists the $f_2$ similarity values, calculated using the equations described below, for the SNEDDs, SEDDs and cosolvent formulations. An $f_2$ value between 50-100 suggests that the two dissolution profiles are similar. The asterisk* depicts significance between groups compared after analysis by ANOVA using Tukey's post-hoc test, at a threshold of significance at p<0.05.

TABLE X

| $f_2$ Similarity Values Extent of Release | SNEDDS/ Cosolvent | SEDDS/ Cosolvent | SNEDDS/ SEDDS |
| --- | --- | --- | --- |
| 0-20 minutes | 71.0 | 77.1 | 92.6 |
| 20-60 minutes | 56.0* | 54.5* | 97.3 |
| Rate of Release 0-20 minutes | 75.6 | 78.5 | 94.9 |

Both the SNEDDS and SEDDS were physically stable in the GI fluids without any changes in their droplet sizes. Further, the drug was chemically stable in the GI fluids (SGF, SIF) for 4 hours. Increased dilutions did not affect the physical stability of the formulation or the chemical stability of the drug. SNEDDS and SEDDS formulations were also chemically stable with drug contents of 97.8±0.6% and 98.2±0.4%, respectively, and over a period of one and one-half year at room temperature.

The lead parenteral cosolvent formulation as a reference for oral bioavailability studies was stable for over a two-week period having drug concentrations of 2.0±0.1 (n=6) mg/ml and incorporated the least amount of DMSO (10% w/w). The absolute oral bioavailabilities of the SNEDDS, SEDDS and the unformulated suspension administered orally were 70.7%, 37.4% and 0.3%, respectively, in reference to the I.V. cosolvent formulation. The relative bioavailabilities of SNEDDS and SEDDS, in reference to the unformulated suspension were 228% and 120%, respectively, while the SNEDDS formulation had approximately two fold higher oral bioavailability compared to SEDDS. The SNEDDS and SEDDS formulations were designed rationally to identify the relative contributions of the effects of particle size and lipid digestion on the bioavailability enhancement processes. The particle size was the driving factor for enhanced absorption from SNEDDS of 35 nm, while lipid digestion played an important role in enhancing bioavailability for the SEDDS.

Table XI provides a summary of vital pharmacokinetic parameters of mebendazole in rats after oral administration of SNEDDS, SEDDS, unformulated suspensions and parenteral cosolvent formulations.

Mean Plasma-Concentration Time Profiles

Figure 12A:
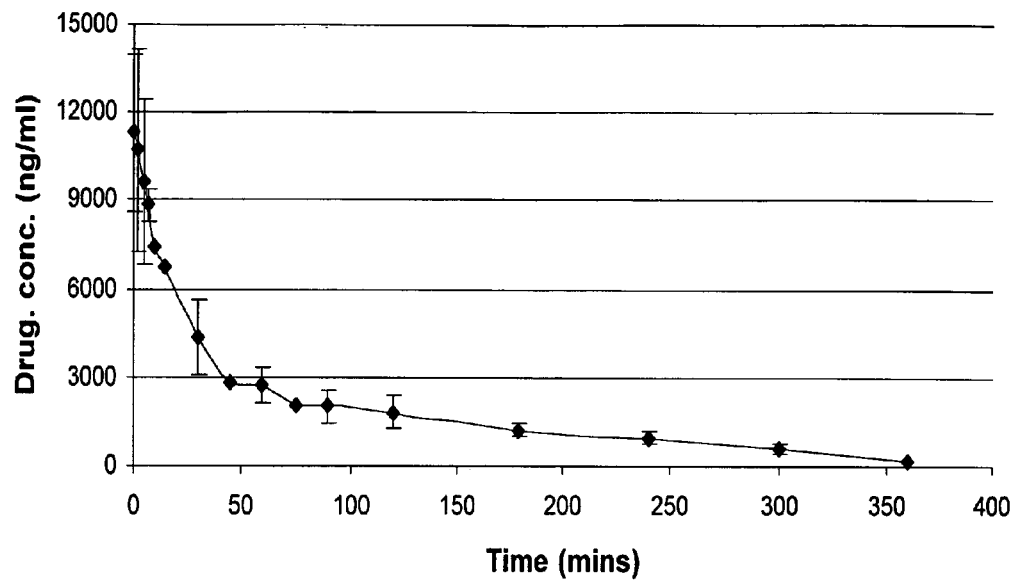
FIGS. 12A-12G. Mean plasma-concentration time profiles of mebendazole in Sprague-Dawley rats after i.v. bolus of parenteral cosolvent formulation (FIG. 12A), after oral administration of SNEDDS (FIG. 12B), SEDDS (FIG. 12C) and unformulated suspension (FIG. 12D) and after i.v. bolus of parenteral microemulsions PM1 (FIG. 12E) and PM2 (FIG. 12F).
Figure 12B:
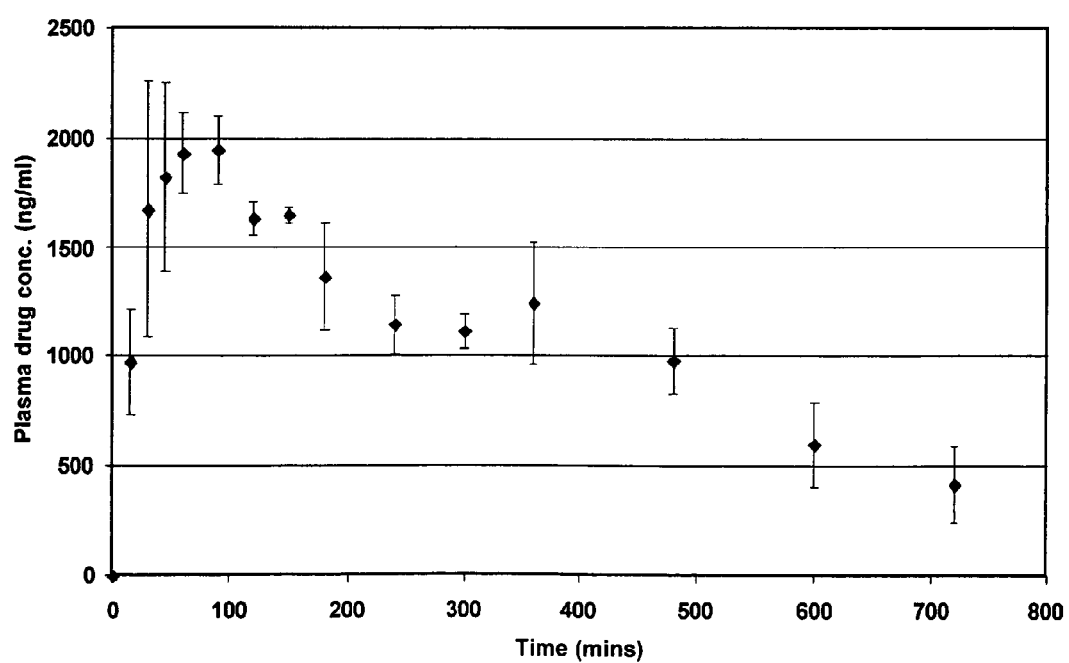
Figure 12C:
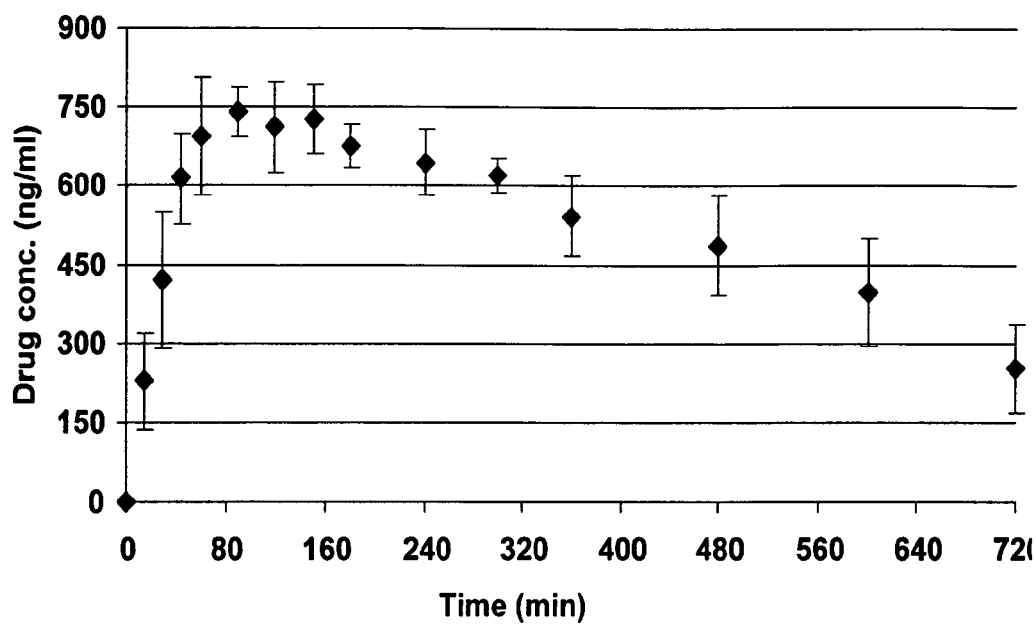
Figure 12D:
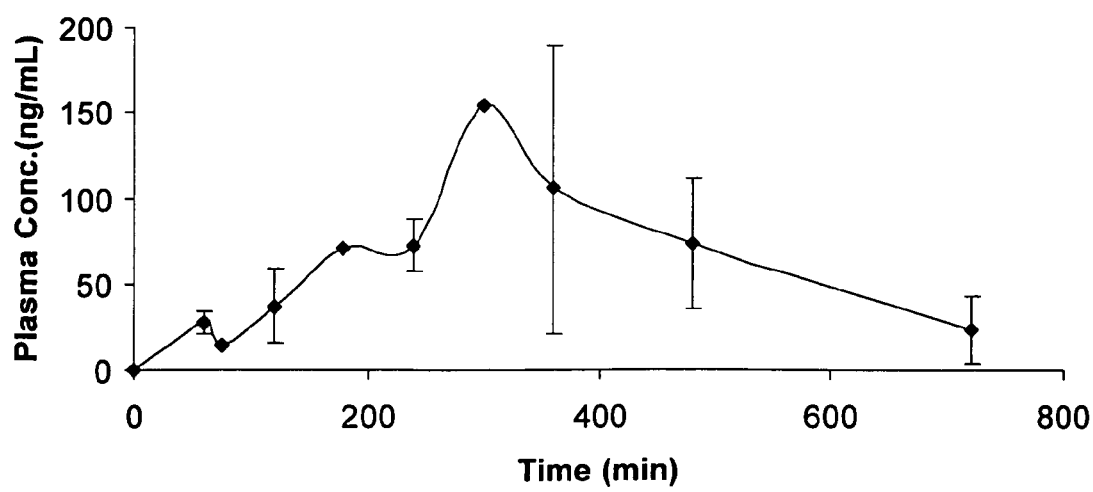
Figure 12E:
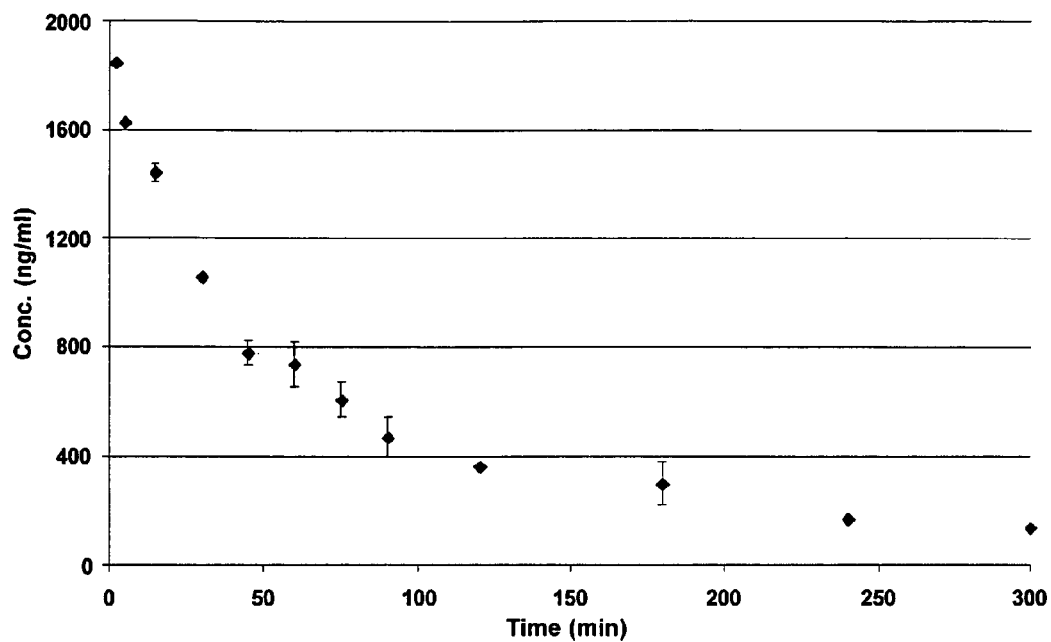
Figure 12F:
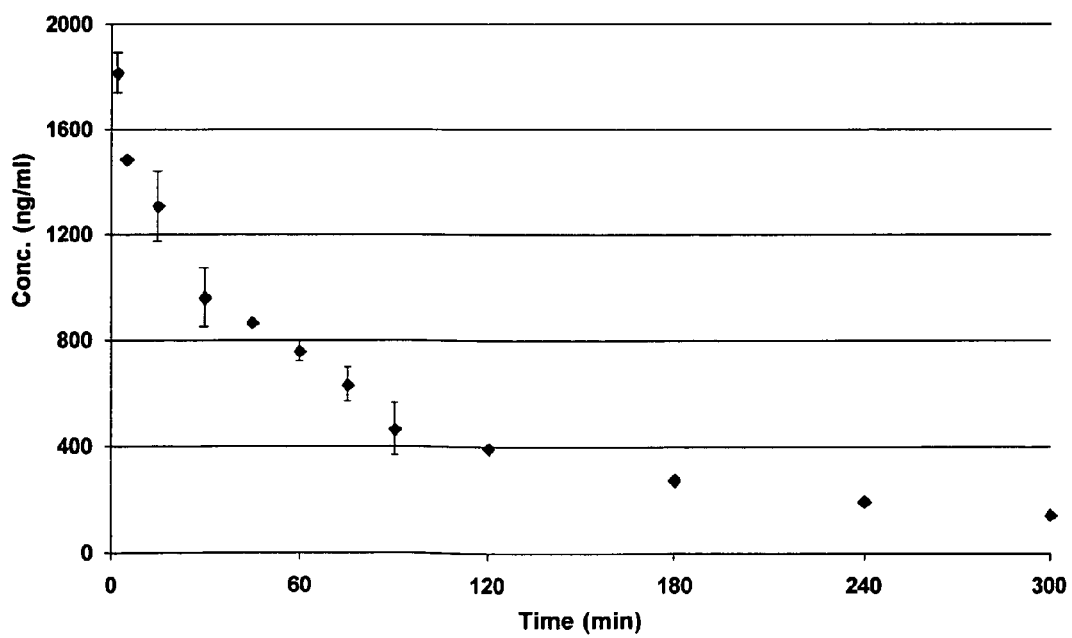
Figure 12G:
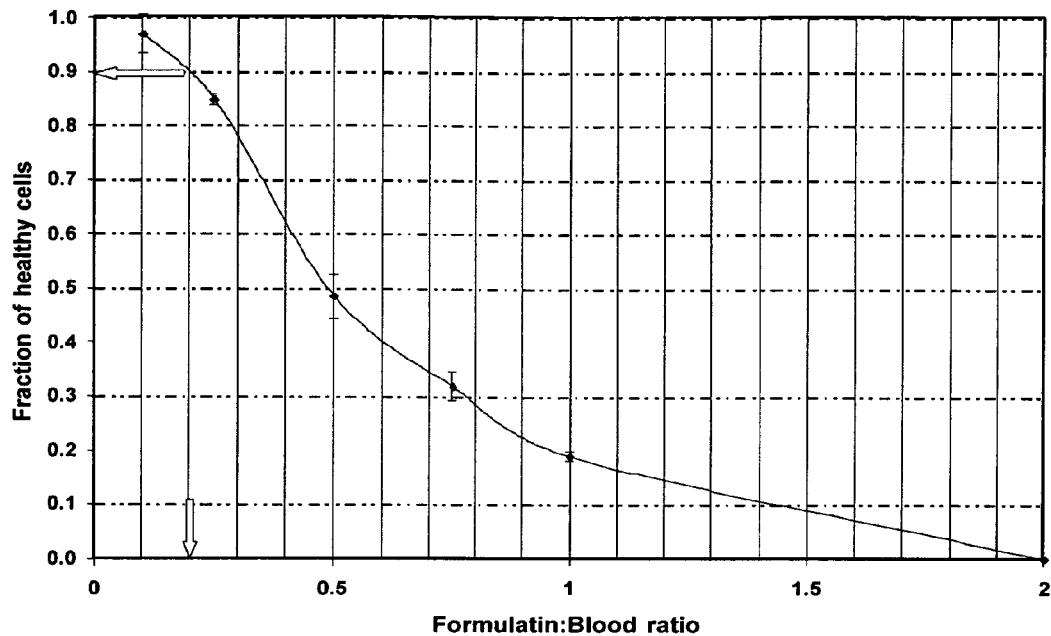

Groups of Sprague-Dawley rats were administered mebendazole either parenterally via an i.v bolus or orally via oral gavage and the mean plasma-concentration time profile was measured over a period of about 12 hours. SD rats were administered 1) 3.25 mg/kg (n=6) of a parenteral cosolvent formulation intravenously (FIG. 12A); 2) 5.0 mg/kg (n=4) of SNEDDS orally (FIG. 12B); 3) 5.0 mg/kg (n=5) of SEDDS orally (FIG. 12C); 4) 50.0 mg/kg (n=4) of an unformulated suspension orally (FIG. 12D); 5) 1.60 mg/kg (n=3) of each of parenteral microemulsions PM1 and PM2 intravenously (FIGS. 12E-12F). Note in FIG. 12D that the standard deviations of the plasma-drug concentrations are very high because of slow and erratic absorption of mebendazole from the unformulated suspension. The hemolytic potential, H10%, of the formulation is interpolated from FIG. 12G to be 0.2. Thus, because of the substantially low surfactant/cosurfactant content, i.e., about 6% to about 48%, preferably about 27% to about 42%, of SNEDDS and microemulsions PM1 and PM2, these formulations are hemolytically safe for parenteral administration. With increased volumes of the formulation used, the hemolysis increased with 90% of the cells hemolyzed at a formulation to blood ratio of 1.5.

Table XII provides a summary of pharmacokinetic parameters from intravenous cosolvent and microemulsion formulations in rats. All values are shown as mean±S.D. Differences between any two means were statistically evaluated using ANOVA, with Tukey's post-hoc analysis, at a threshold of significance at p<0.05. The *p<0.05 for comparison between cosolvent and microemulsion formulations.

TABLE XII

| Pharmacokinetic Parameters | I.V. Formulations | | |
| --- | --- | --- | --- |
| | Cosolvent | Microemulsion (PM1-37 nm) | Microemulsion (PM2-478 nm) |
| No. of SD rats | n = 6 | n = 3 | n = 3 |
| Dose (mg/kg) | 3.25 | 1.6 | 1.6 |
| AUC (μg * min/ml) | 908.6 ± 148.2 | 159.7 ± 11.1 | 170.2 ± 2.1 |
| AUC/Dose | 279.6 ± 45.6* | 99.8 ± 6.9 | 106.4 ± 1.3 |
| $C_{max}$ (μg/ml) | 11.3 ± 2.7 | 2.0 ± 0.1 | 1.8 ± 0.1 |
| $C_{max}$/Dose | 3.5 ± 0.8* | 1.3 ± 0.1 | 1.1 ± 0.1 |
| $t_{1/2, \alpha}$ (min) | 17.0 ± 3.6 | 17.9 ± 4.9 | 24.0 ± 3.9 |
| $t_{1/2, \beta}$ (min) | 173.4 ± 100.3 | 114.1 ± 27.0 | 145.7 ± 21.4 |

TABLE XI

| Pharmacokinetic Parameters | Formulations | | | |
| --- | --- | --- | --- | --- |
| | SNEDDS (35 nm) | SEDDS (143 nm) | Unformulated Suspension | Cosolvent Formulation |
| No. of subjects | n = 4 | n = 5 | n = 4 | n = 6 |
| Route of Adminstration | p.o | p.o | p.o | i.v. |
| Dose (mg/kg) | 5.0 | 5.0 | 50.0 | 3.25 |
| $C_{max}$ or $C_{o(i.v.)}$ (μg/ml) | 1.89 ± 0.37** | 0.58 ± 0.06* | 0.13 ± 0.05 | 11.30 ± 2.65 |
| AUC (min * μg/ml) | 987.76 ± 112.16** | 522.40 ± 14.40* | 40.05 ± 20.14 | 908.63 ± 148.23 |
| $t_{max}$ (min) | 67.0 ± 23.6** | 129.4 ± 39.4* | 315.0 ± 57.0 | — |
| Absolute Bioavailability (%) | 70.7** | 3.74* | 0.30 | 100 |
| Relative Bioavailability (to Unformulated Suspension) | 228* | 120* | 100 | — |

TABLE XII-continued

| Pharmaco-kinetic Parameters | Cosolvent | I.V. Formulations | |
|---|---|---|---|
| | | Microemulsion (PM1-37 nm) | Microemulsion (PM2-478 nm) |
| Clearance (ml/min) | 3.7 ± 0.6* | 10.1 ± 0.7 | 9.4 ± 0.1 |
| Vss (ml) | 692.2 ± 265.6* | 1353.6 ± 152.3 | 1584.7 ± 212.3 |
| $V_1$ (ml) | 303.4 ± 69.1* | 814.4 ± 40.4 | 895.0 ± 52.6 |
| $V_2$ (ml) | 388.8 ± 249.3 | 539.3 ± 189.3 | 689.7 ± 172.7 |
| $\alpha$ (min$^{-1}$) | 0.043 ± 0.009 | 0.041 ± 0.010 | 0.030 ± 0.005 |
| $\beta$ (min$^{-1}$) | 0.005 ± 0.003 | 0.006 ± 0.001 | 0.005 ± 0.001 |
| $k_{10}$ (min$^{-1}$) | 0.013 ± 0.004 | 0.012 ± 0.001 | 0.011 ± 0.000 |
| $k_{12}$ (min$^{-1}$) | 0.018 ± 0.005 | 0.013 ± 0.002 | 0.022 ± 0.010 |
| $k_{21}$ (min$^{-1}$) | 0.017 ± 0.006 | 0.022 ± 0.010 | 0.013 ± 0.003 |

Plasma Pharmacokinetics of Cosolvent and Microemulsions PM1 and PM2 in Mice

Plasma pharmacokinetics for Mbz from cosolvent and microemulsions (PM1 and PM2) in mice have been studied. A naive averaged data approach where mean concentration-time profiles were generated by calculating the mean concentration at each time point was employed for each formulation. The mean plasma pharmacokinetic parameters were derived from the mean concentration-time profile for each formulation by WinNonlin (Table XIII). Therefore, the values of pharmacokinetic parameters were presented as mean values derived from mean concentration-time profiles. No standard deviations were presented and statistical analysis was not performed. Bioavailability, BA, is the ratio of the AUC/dose of PM1 or PM2 to that of cosolvent.

Figure 13:
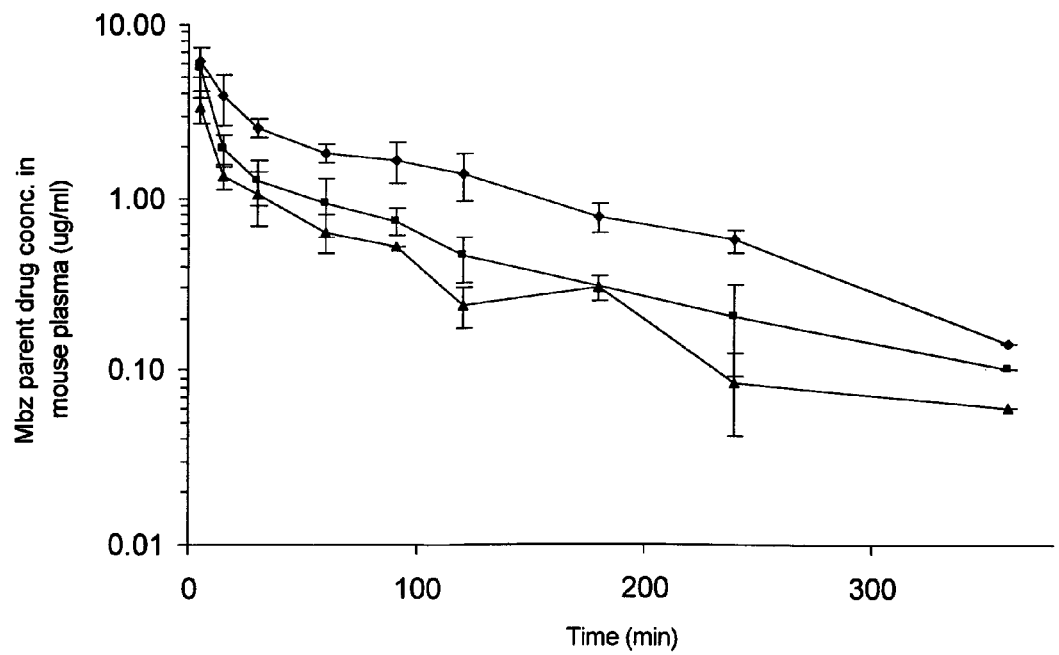
FIG. 13. Plasma concentration profiles of mebendazole from cosolvent (◆) and parenteral microemulsions PM1 (■) and PM2 (▲) formulations in mice.

For all of these three formulations, the Mbz plasma concentration declined rapidly after injection and was too low to be detected after 6 hr (FIG. 13). The plasma concentration-time profiles of Mbz from these three formulations following i.v. injection in mice were best fitted in a two-compartment model. Curves for three concentration-time profiles displayed short distribution a phase ($t_{1/2}$, $\alpha$<0.1 hr), which indicated a rapid distribution phase (Table XIII). The Mbz pharmacokinetic parameters such as AUC/dose, $t_{1/2}\alpha$, $t_{1/2}$, $\beta$, and CL were comparable among groups of cosolvent, PM1 and PM2.

However, the $C_{max/dose}$ of cosolvent was 1.45 (mg/L)/(mg/kg), only about half of those of PM1 and PM2, 3.49 and 3.24 (mg/L)/(mg/kg), respectively. In addition, $k_{10}$ for cosolvent was 1.27 hr$^{-1}$, which was about half of those for PM1 and PM2, 2.87 and 2.25 hr$^{-1}$, respectively. $k_2$ for cosolvent was 3.57 hr$^{-1}$, which was 2 times higher than those for PM1 and PM2, 1.62 and 1.76 hr$^{-1}$, respectively. The relative bioavailability was 1.07 and 1.26 for PM1 and PM2, respectively. In contrast to these differences between Mbz cosolvent and microemulsions (PM1 and PM2), all plasma pharmacokinetic parameters were comparable between PM1 and PM2.

TABLE XIII

| Pharmacokinetic Parameters | Units | Cosolvent | PM1 | PM2 |
|---|---|---|---|---|
| Dose | mg/kg | 6.5 | 3.25 | 2.5 |
| $C_{max}$/Dose | (mg/L)/(mg/kg) | 1.45 | 3.49 | 3.24 |
| AUC/Dose | (hr * mg/L)/(mg/kg) | 1.14 | 1.22 | 1.44 |
| $t_{1/2,\_}$ | hr | 0.078 | 0.068 | 0.095 |
| $t_{1/2,\_}$ | hr | 1.34 | 1.52 | 1.27 |
| $\alpha$ | 1/hr | 8.84 | 10.01 | 7.28 |
| $\beta$ | 1/hr | 0.51 | 0.46 | 0.54 |
| CL | L/hr | 0.029 | 0.027 | 0.023 |
| $V_{ss}$ | L | 0.051 | 0.044 | 0.032 |
| $V_1$ | L | 0.023 | 0.009 | 0.010 |
| $V_2$ | L | 0.028 | 0.035 | 0.022 |
| $k_{10}$ | 1/hr | 1.27 | 2.87 | 2.25 |
| $k_{12}$ | 1/hr | 4.52 | 6.17 | 3.81 |
| $k_{21}$ | 1/hr | 3.57 | 1.62 | 1.76 |
| Relative BA | | | 1.07 | 1.26 |

Biodistributions of Mbz from Cosolvent and Microemulsions (PM1 and PM2) in Mice

Figure 14A:
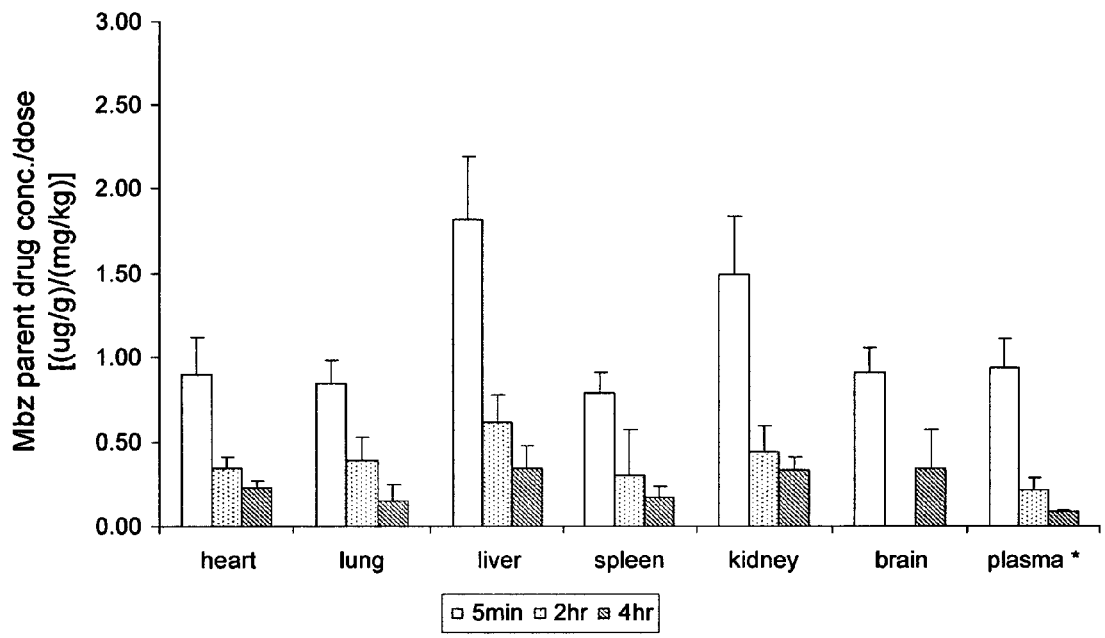
FIGS. 14A-14C. Biodistributions for cosolvent (FIG. 14A), PM1 (FIG. 14B) and PM2 (FIG. 14C) formulations in mice.
Figure 14B:
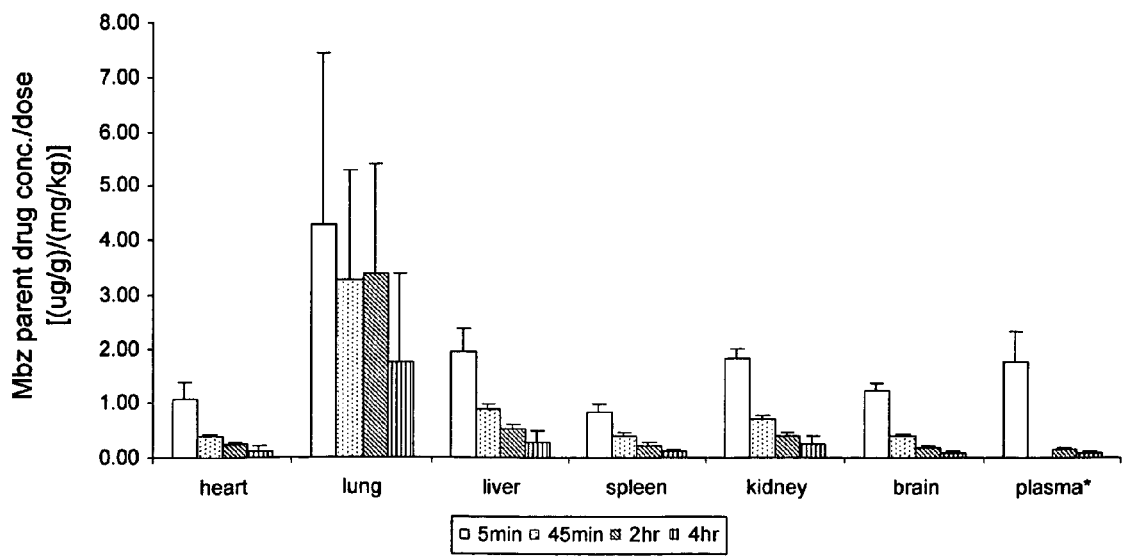
Figure 14C:
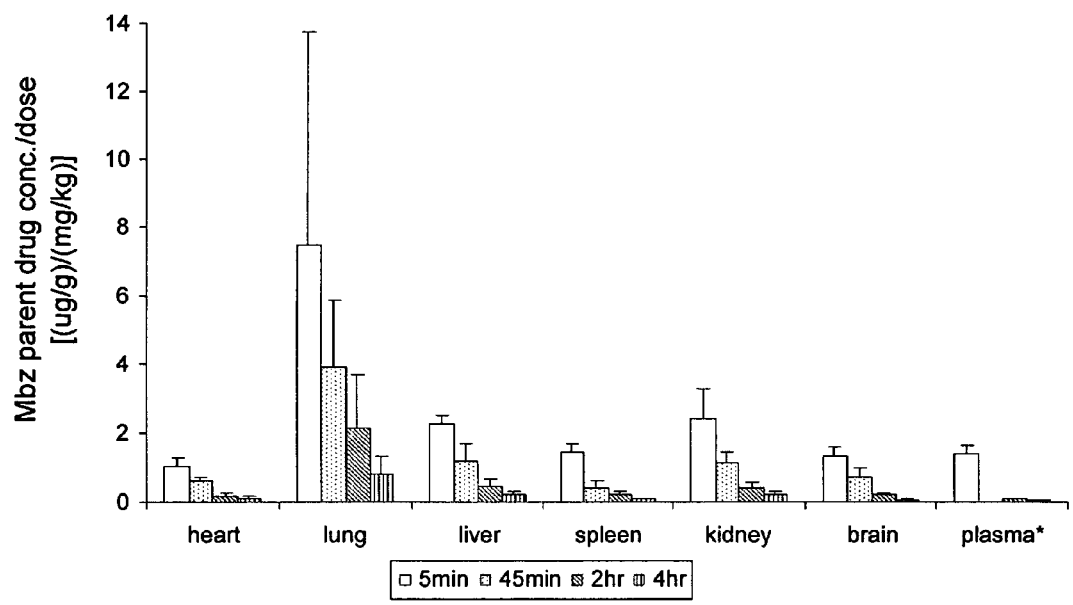

Different tissue distribution patterns among Mbz from cosolvent, PM1 and PM2 were observed which were not anticipated based on their plasma pharmacokinetic profiles (FIGS. 14A-14C). Mbz peak concentrations in different organs were reached by 5 min after injection for all formulations. For cosolvent, the top two highest peak concentrations were 1.82 (μg/g)/(mg/kg) in liver and 1.50 (μg/g)/(mg/kg) in kidneys, in contrast to 4.28 (μg/g)/(mg/kg) in lung, 1.94 (μg/g)/(mg/kg) in liver, and 1.82 (μg/g)/(mg/kg) in kidneys for PM1, and 7.46 (μg/g)/(mg/kg) in lung, 2.40 (μg/g)/(mg/kg) in kidneys, 2.24 (μg/g)/(mg/kg) in liver for PM2. Table XIV presents the biodistributions for cosolvent formulations and parenteral microemulsions PM1 with a droplet size of 37 nm and PM2 with a droplet size of 478 nm in mice (n=4-5).

Mbz in cosolvent yielded the highest exposure in liver with an AUC of 3.37 (hr*μg/g)/(mg/kg), followed by kidneys of 2.70 (hr*μg/g)/(mg/kg). However, for PM1, the AUC in lung [12.38 (hr*μg/g)/(mg/kg)] was the highest, followed by those in liver [2.69 (hr*μg/g)/(mg/kg)] and kidneys [2.19 (hr*μg/g)/(mg/kg)]. For PM2, the AUC in lung [10.82 (hr*μg/g)/(mg/kg)] was the highest too, followed by those in liver [2.95 (hr*μg/g)/(mg/kg)] and kidneys [2.78 (hr*μg/g)/(mg/kg)]. Comparing the microemulsion group (PM1 and PM2) with Mbz cosolvent, the AUCs in lung from PM1 and PM2 were 6-7 times, and the AUC in brain were 50%-60% of those from MBz cosolvent, respectively. The AUCs in the rest organs were comparable between Mbz microemulsions and cosolvent. The AUCs in all six organs were comparable between PM1 and PM2.

For cosolvent, the elimination half-lives of Mbz were similar in heart, lung, liver, spleen, and kidneys, 1.96, 1.60, 1.63, 1.79, and 1.83 hr, respectively. The elimination half-life in lung (4.54 hr) was substantially prolonged for PM1, which was about 3 times of that from cosolvent. Half-lives of Mbz from PM1 in other organs except brain were 1.38, 1.55, 1.40, and 1.44 hr in heart, liver, spleen and kidneys, respectively, similar to those from cosolvent. Half-lives of Mbz from PM2 in all organs except brain were 1.18, 1.27, 1.15, 1.03 and 1.08 hr in heart, liver, spleen and kidneys, respectively, similar to those from cosolvent and PM1. Half-lives of Mbz in brain from PM1 and PM2 were comparable, 1.05 and 0.93 hr, respectively, but much shorter than that from cosolvent (2.85 hr).

Figure 15A:
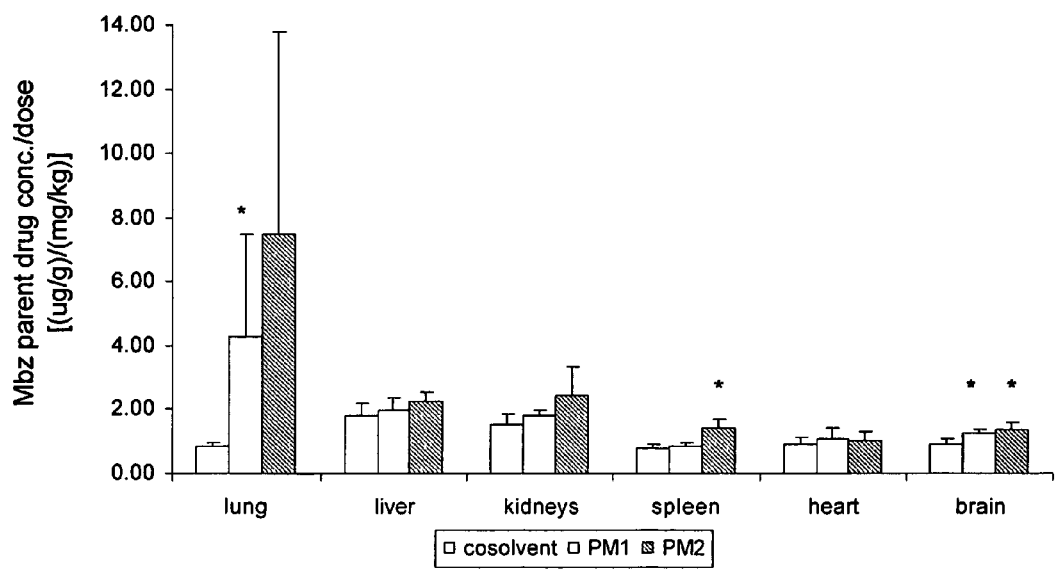
FIGS. 15A-15C. Comparison of mebendazole concentrations in organs at 5 min (FIG. 15A), 2 hr (FIG. 15B) and 4 hr (FIG. 15C) after i.v. injection of cosolvent, PM1 (37 nm), and PM2 (478 nm) in mice (n=4-5).
Figure 15B:
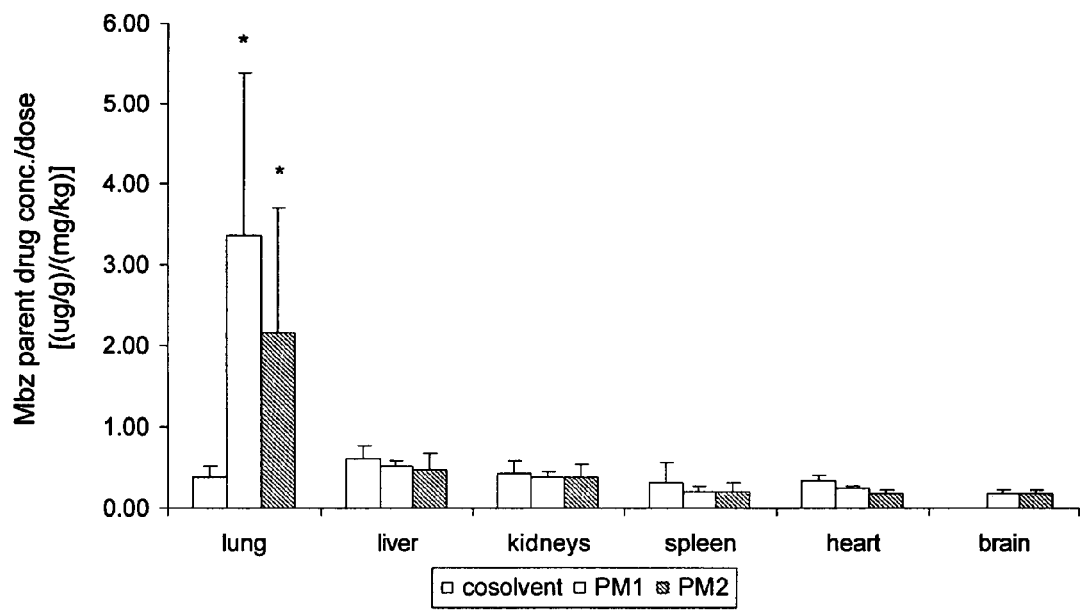
Figure 15C:
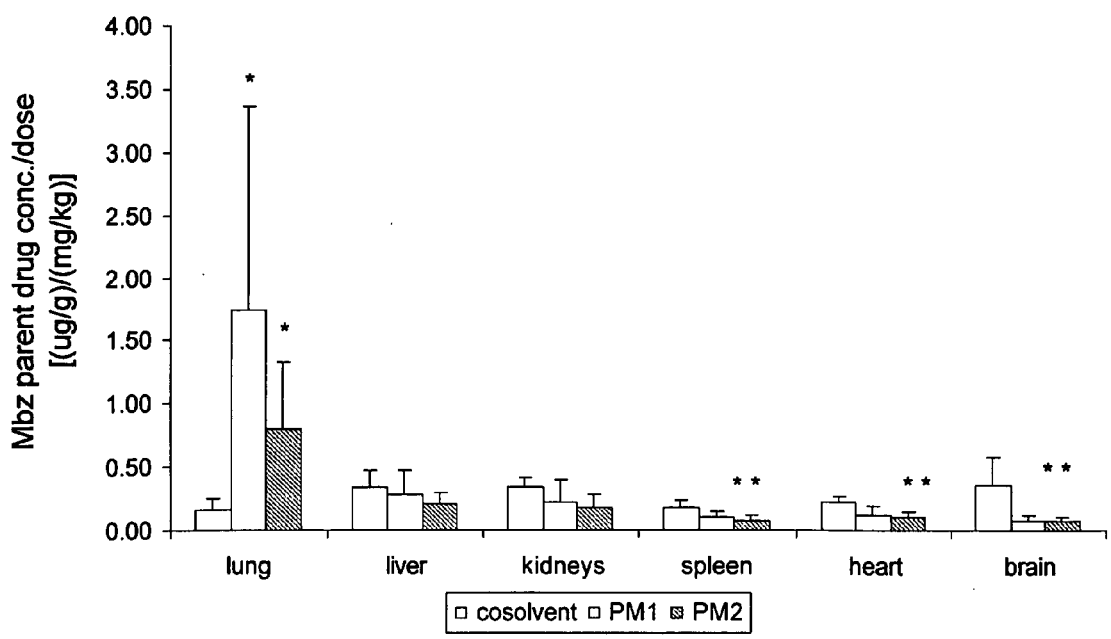
Figure 17A:
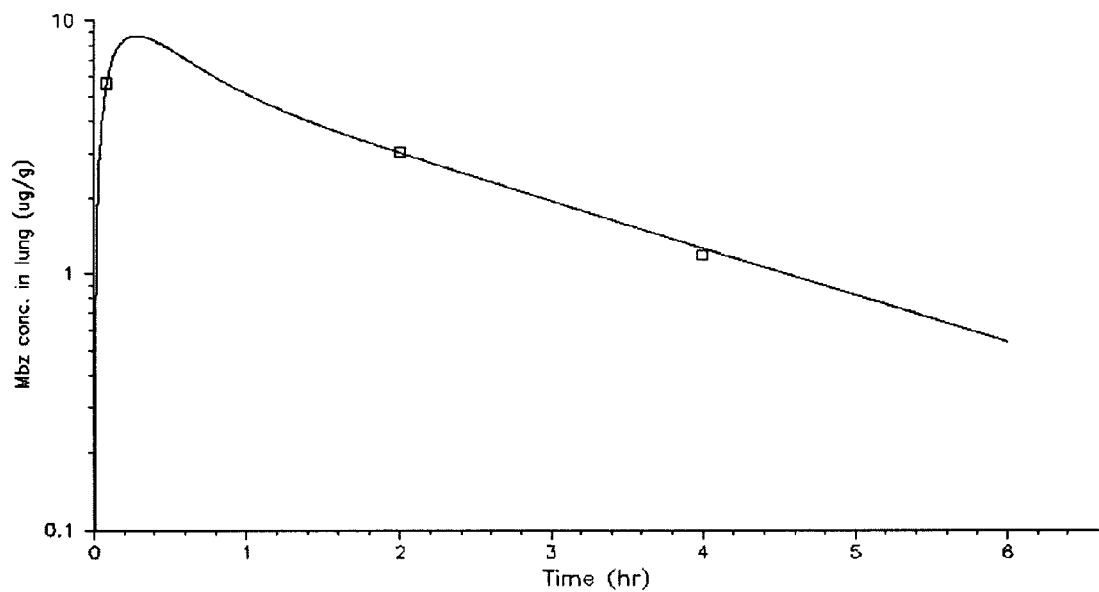
FIGS. 17A-17F. Three-compartmental model fitting of semi-log plot of mean plasma concentrations and mean lung concentrations of Mbz after i.v. administration of cosolvent (FIGS. 17A-17B), PM1 (FIGS. 17C-17D) and PM2 (FIGS. 17E-17F) formulations.
Figure 17B:
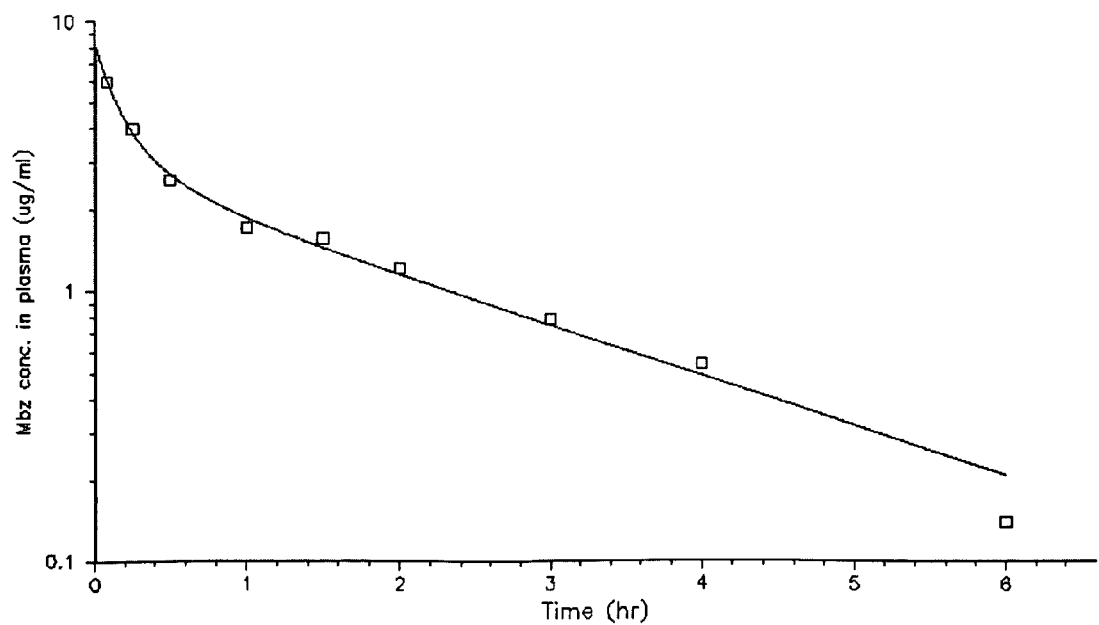
Figure 17C:
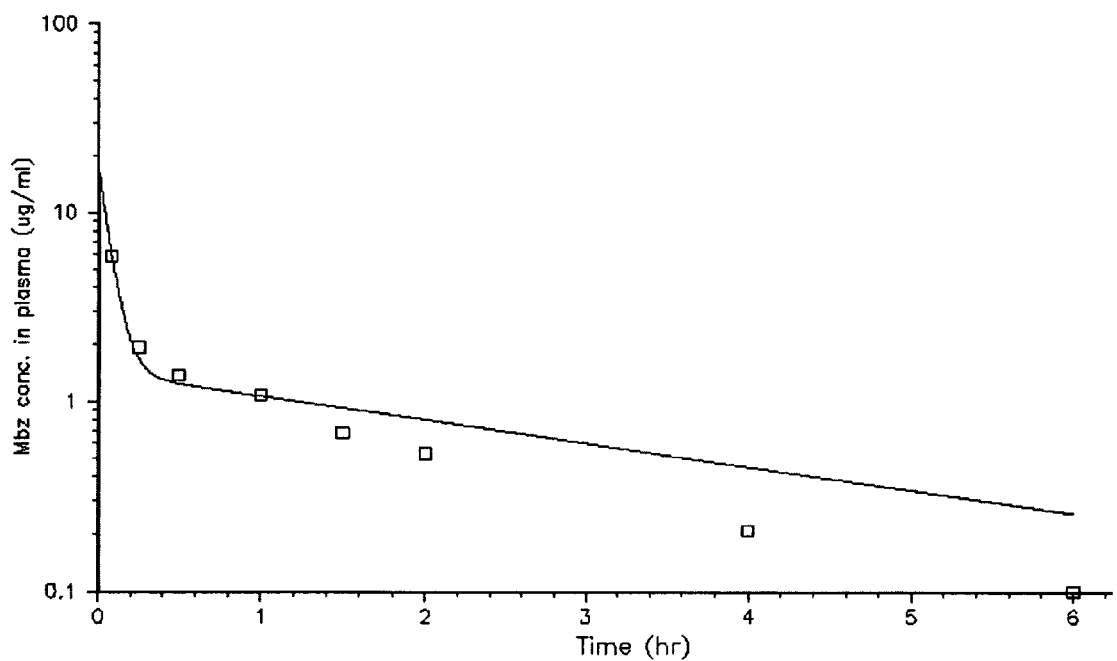
Figure 17D:
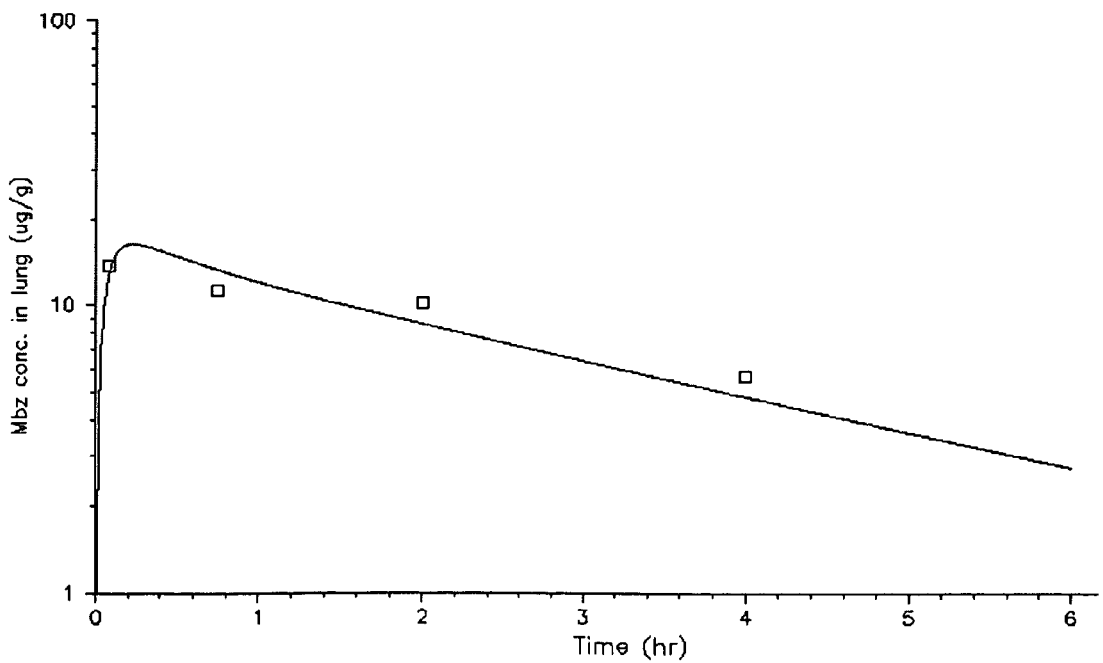
Figure 17E:
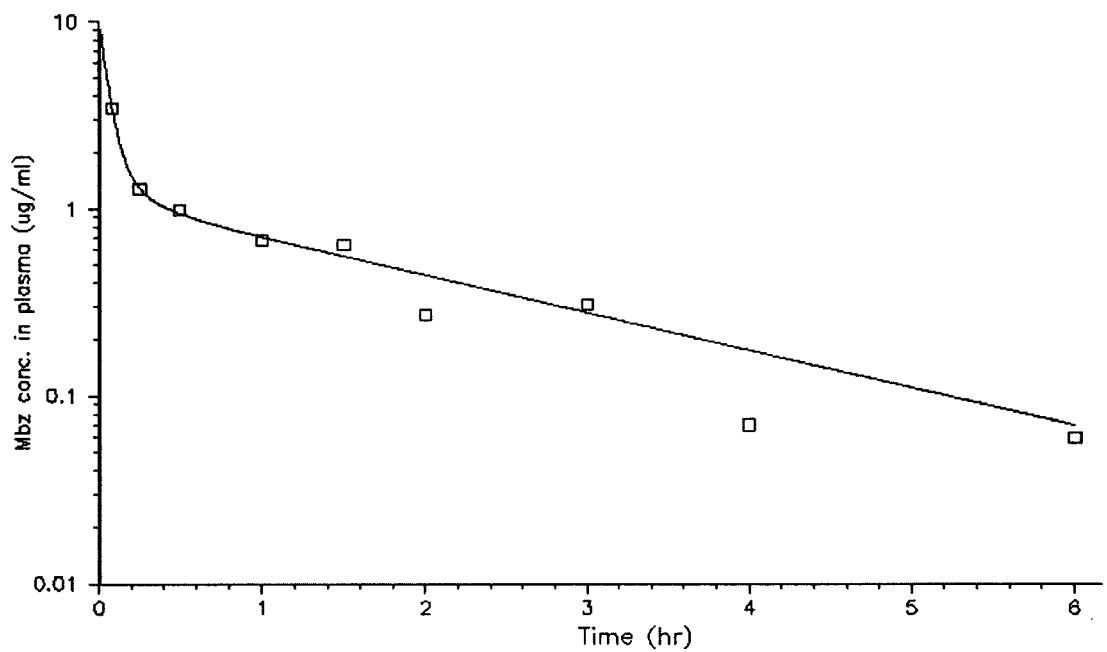
Figure 17F:
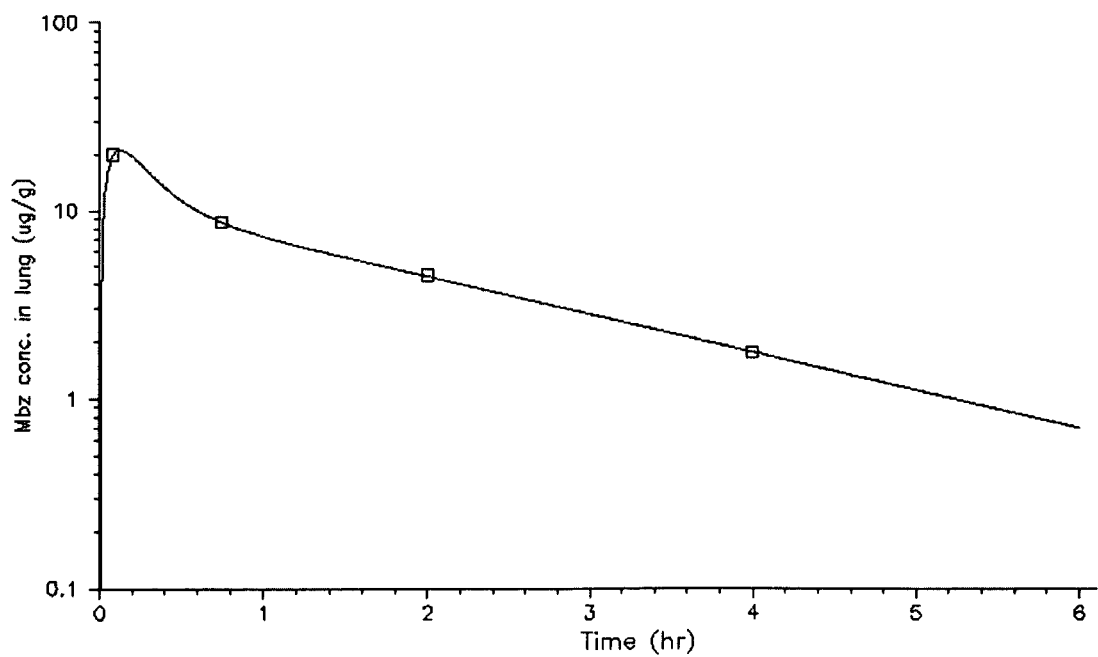

Comparing Mbz concentrations from cosolvent, PM1 and PM2 at 5 min, a significantly higher Mbz concentration at 5 min in spleen from PM2 than those from cosolvent and PM1 was found. In addition, the Mbz concentrations in lung and brain at 5 min from PM1 and PM2 were significantly higher than those from cosolvent too. The peak Mbz concentrations in liver and kidney were comparable among these three formulations (FIGS. 15A-15C). At 2 hr, PM1 and PM2 still possessed significantly higher Mbz concentrations in lung than cosolvent. At 4 hr, the Mbz concentrations in lung from PM1 and PM1 were significantly higher than that from cosolvent. In contrast, the Mbz concentrations in spleen, heart and brain were significantly lower than that from cosolvent.

The observation of substantial distributions of Mbz in lung from PM1 and PM2 was not anticipated. The retention of Mbz from PM1 in lung was prolonged from that of cosolvent. Nevertheless, the retained Mbz from PM2 was eliminated faster, resulting in a similar half-life to that of cosolvent. The significantly greater AUC and prolonged half-life of Mbz in lung from PM1 may offer potential merits of Mbz delivery for treatments of lung cancer and pulmonary infections.

TABLE XIV

| PARAMETERS | Heart | Lung | liver | spleen | kidneys | Brain |
|---|---|---|---|---|---|---|
| Cosolvent | | | | | | |
| $C_{max}$ (μg/g)/(mg/kg) | 0.90 | 0.85 | 1.82 | 0.79 | 1.50 | 0.90 |
| $AUC_{0\text{-}4\,hr}$ (hr * μg/g)/(mg/kg) | 1.79 | 1.76 | 3.37 | 1.57 | 2.70 | 2.49 |
| $t_{1/2}$ (hr) | 1.96 | 1.60 | 1.63 | 1.79 | 1.83 | 2.85 |
| PM1 | | | | | | |
| $C_{max}$ (μg/g)/(mg/kg) | 1.08 | 4.28 | 1.94 | 0.85 | 1.82 | 1.22 |
| $AUC_{0\text{-}4\,hr}$ (hr * μg/g)/(mg/kg) | 1.29 | 12.38 | 2.69 | 1.11 | 2.19 | 1.21 |
| $t_{1/2}$ (hr) | 1.38 | 4.54 | 1.55 | 1.40 | 1.44 | 1.05 |
| PM2 | | | | | | |
| $C_{max}$ (μg/g)/(mg/kg) | 1.03 | 7.46 | 2.24 | 1.41 | 2.40 | 1.34 |
| $AUC_{0\text{-}4\,hr}$ (hr * μg/g)/(mg/kg) | 1.35 | 10.82 | 2.95 | 1.36 | 2.78 | 1.56 |
| $t_{1/2}$ (hr) | 1.18 | 1.27 | 1.15 | 1.03 | 1.08 | 0.93 |

Comparison of the Formulation and Size Effect on Mbz Disposition Between Species Mbz from cosolvent and microemulsions all followed a two-compartment model after i.v. injection. In both mice and rats, Mbz microemulsions exhibited similar plasma pharmacokinetics as cosolvent. The droplet size of Mbz microemulsions did not show significant effect on Mbz plasma pharmacokinetics, as PM1 and PM2 exhibited very similar plasma pharmacokinetics in both mice and rats (Table XV). In Table XV Differences among groups were statistically evaluated using one-way ANOVA with Turkey's post hoc test at P<0.05. The asterisk * denotes P<0.05 for difference between cosolvent and microemulsion formulations (PM1 and PM2) in rats.

TABLE XV

| | Pharmacokinetic Parameters | | | | | |
|---|---|---|---|---|---|---|
| | Cosolvent | | PM1 | | PM2 | |
| | Species | | | | | |
| | Mice | Rats | Mice | Rats | Mice | Rats |
| Dose (mg/kg) | 6.5 | 3.25 | 3.25 | 1.6 | 2.5 | 1.6 |
| $C_{max}$/Dose (ug/ml/mg/kg) | 1.45 | 3.48 ± 0.83 | 3.49 | 1.25 ± 0.06 | 3.24 | 1.13 ± 0.06 |
| AUC/Dose (hr * ug/ml/mg/kg) | 1.14 | 4.66 ± 0.76 | 1.22 | 1.66 ± 0.12 | 1.44 | 1.77 ± 0.02 |
| $t_{1/2,\alpha}$ (hr) | 0.078 | 0.28 ± 0.06 | 0.068 | 0.30 ± 0.08 | 0.095 | 0.40 ± 0.07 |
| $t_{1/2,\beta}$ (hr) | 1.34 | 2.89 ± 1.67 | 1.52 | 1.90 ± 0.45 | 1.27 | 2.43 ± 0.36 |
| CL (L/hr/kg) | 0.97 | 0.73 ± 0.1* | 0.90 | 2.03 ± 0.13 | 0.77 | 1.86 ± 0.03 |
| $V_{ss}$ (L/kg) | 1.70 | 2.30 ± 0.90* | 1.47 | 4.50 ± 0.50 | 1.07 | 5.27 ± 0.70 |
| $V_1$ (L/kg) | 0.77 | 1.00 ± 0.23* | 0.30 | 2.70 ± 0.13 | 0.33 | 3.00 ± 0.17 |
| $V_2$ (L/kg) | 0.93 | 1.27 ± 0.83 | 1.17 | 1.80 ± 0.63 | 0.73 | 2.30 ± 0.57 |
| ($hr^{-1}$) | 8.84 | 2.58 ± 0.54 | 10.01 | 2.46 ± 0.60 | 7.28 | 1.80 ± 0.30 |
| ($hr^{-1}$) | 0.51 | 0.30 ± 0.12 | 1.36 | 0.36 ± 0.06 | 0.54 | 0.30 ± 0.06 |
| $k_{10}$ ($hr^{-1}$) | 1.27 | 0.78 ± 0.12 | 2.87 | 0.72 ± 0.06 | 2.25 | 0.66 ± 0.02 |
| $k_{12}$ ($hr^{-1}$) | 4.52 | 1.08 ± 0.30 | 6.17 | 0.78 ± 0.12 | 3.81 | 1.32 ± 0.60 |
| $k_{21}$ ($hr^{-1}$) | 3.57 | 1.02 ± 0.36 | 1.62 | 1.32 ± 0.60 | 1.76 | 0.78 ± 0.18 |

Development of Pharmacokinetic Models for Dispositions of Mbz in Cosolvent and Nanoformulations in Mice Interestingly, intravenous administration of Mbz microemulsions (PM1 and PM2) resulted in very high exposures and retentions in lung, different from the biodistribution pattern from the cosolvent formulation. A pharmacokinetic model was developed which linked the plasma concentrations with lung concentrations of Mbz. A three compartmental model containing central compartment (blood) and two peripheral compartments (lung and rest of the organs, respectively) was built (FIG. 16). The differential equations which described the relationships among three compartments were listed as follows:

$$dA_1/dt = -(K_{12}+K_{13}+K_{10})*A_1+K_{21}*A_2+K_{31}*A_3 \quad \text{(Eq. 1)}$$

$$dA_2/dt = K_{12}*A_1 - K_{21}*A_2 \quad \text{(Eq. 2)}$$

$$dA_3/dt = K_{13}*A_1 - K_{31}*A_2 \quad \text{(Eq. 3)}$$

where $A_1$, $A_2$ and $A_3$ are the amount of drug in the central, lung and other-organ compartments, respectively. $k_{10}$ is the elimination rate microconstant from the central compartment. $k_{12}$, $k_{21}$, $k_{13}$ and $k_{31}$, are microconstants for the transfers of the drug between the central and the peripheral compartments.

In this model, two outputs including the plasma and lung concentrations of Mbz were monitored during the studies. Two equations describing the outputs were listed as follows:

$$C_1 = A_1/V_1 \quad \text{(Eq. 4)}$$

$$C_2 = A_2*K_{21}/(V_1*K_{12}) \quad \text{(Eq. 5)}$$

By fitting experimental data (Table XVI) using ADAPT (FIGS. 17A-17F), the pharmacokinetic parameters in Equations 1-3 were estimated for cosolvent, PM1 and PM2, respectively (Table XVII). Note that the 95% C.I. for cosolvent is unavailable. The AUC Ratio=$AUC_{0\text{-}6\,hr,lung}$/Dose: $AUC_{0\text{-}6,plasma}$/Dose.

The estimated $k_{10}$, $k_{12}$, $k_{13}$, and $k_{31}$ for PM1 were 2.88, 2.99, 8.18, and 1.41 $hr^{-1}$, respectively, similar to those of cosolvent and PM2. The estimated $V_1$ was 6.74 L for PM1, also comparable to that of PM2 (9.12 L), but much less than that of cosolvent (27.77 L). The estimated $k_{21}$ for PM1 was 1.82 $hr^{-1}$, much slower than those of PM2 (5.87 $hr^{-1}$) and cosolvent (5.00 $hr^{-1}$), which could explain the longer $t_{1/2}$ of Mbz in lung from PM1 (4.54 hr) than those from PM1 (1.27 hr) and cosolvent (1.60 hr). These estimated microconstants could be used to predict Mbz concentrations in lung from Mbz concentrations in plasma for Mbz microemulsions. The ratios of AUC in lung and plasma were 8.64 and 9.13 for PM1 and PM2, respectively, much larger than that for cosolvent (2.39).

TABLE XVI

| Time (hr) | Mean plasma concentrations (µg/ml) | | | Time (hr) | Mean plasma concentrations (µg/ml) | | |
|---|---|---|---|---|---|---|---|
| | Cosolvent 6.5 mg/kg | PM1 3.25 mg/kg | PM2 2.5 mg/kg | | Cosolvent 6.5 mg/kg | PM1 3.25 mg/kg | PM2 2.5 mg/kg |
| 0.083 | 5.98 | 5.87 | 3.42 | 0.083 | 5.64 | 13.67 | 20.01 |
| 0.25 | 3.99 | 1.93 | 1.27 | 0.75 | N/A | 11.23 | 8.59 |
| 0.5 | 2.57 | 1.37 | 0.98 | 2.0 | 3.05 | 10.23 | 4.49 |
| 1.0 | 1.71 | 1.08 | 0.68 | 4.0 | 1.20 | 5.67 | 1.74 |
| 1.5 | 1.56 | 0.68 | 0.64 | | | | |
| 2.0 | 1.21 | 0.53 | 0.27 | | | | |
| 3.0 | 0.79 | N/A | N/A | | | | |
| 4.0 | 0.54 | 0.21 | 0.07 | | | | |
| 6.0 | 0.14 | 0.10 | 0.06 | | | | |

Figure 18A:
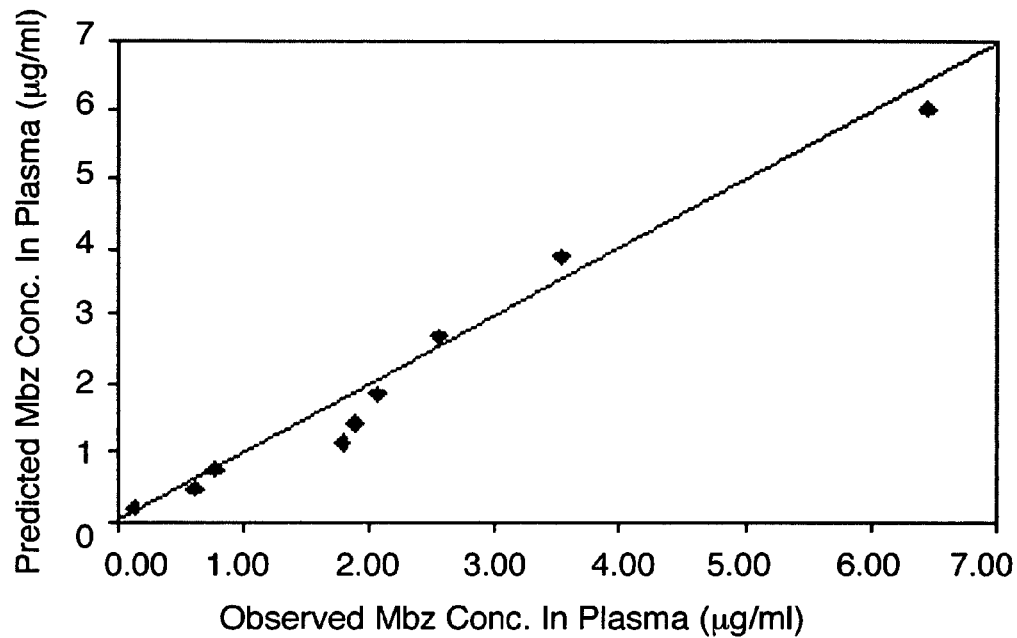
FIGS. 18A-18F. Observed vs. predicted plasma and lung concentrations for cosolvent (FIGS. 18A-18B), PM1 (FIGS. 18C-18D), and PM2 (FIGS. 18E-18F),for the three-compartment model.
Figure 18B:
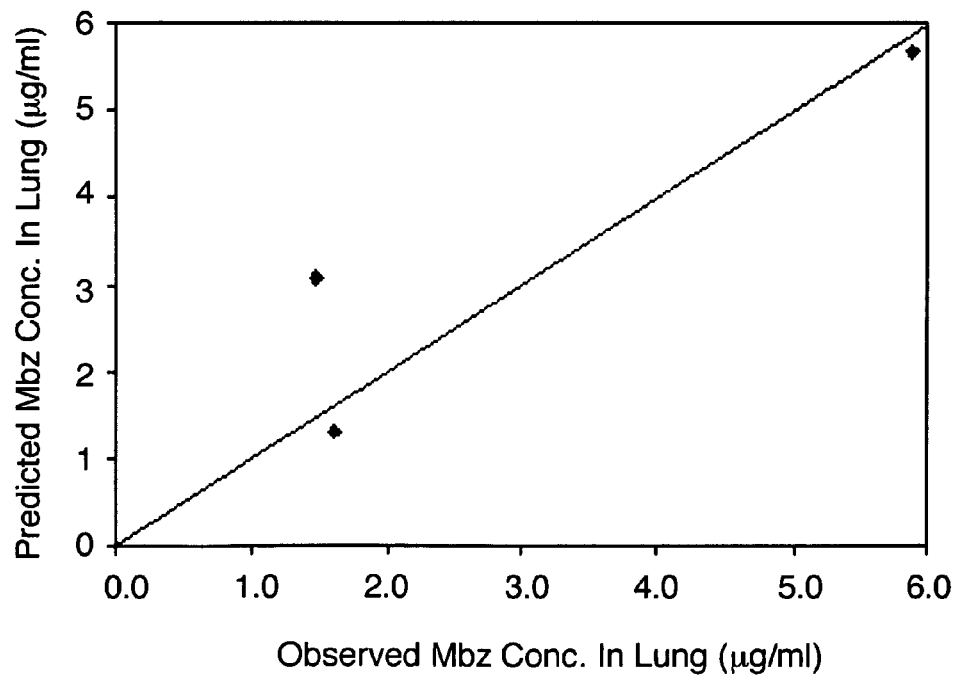
Figure 18C:
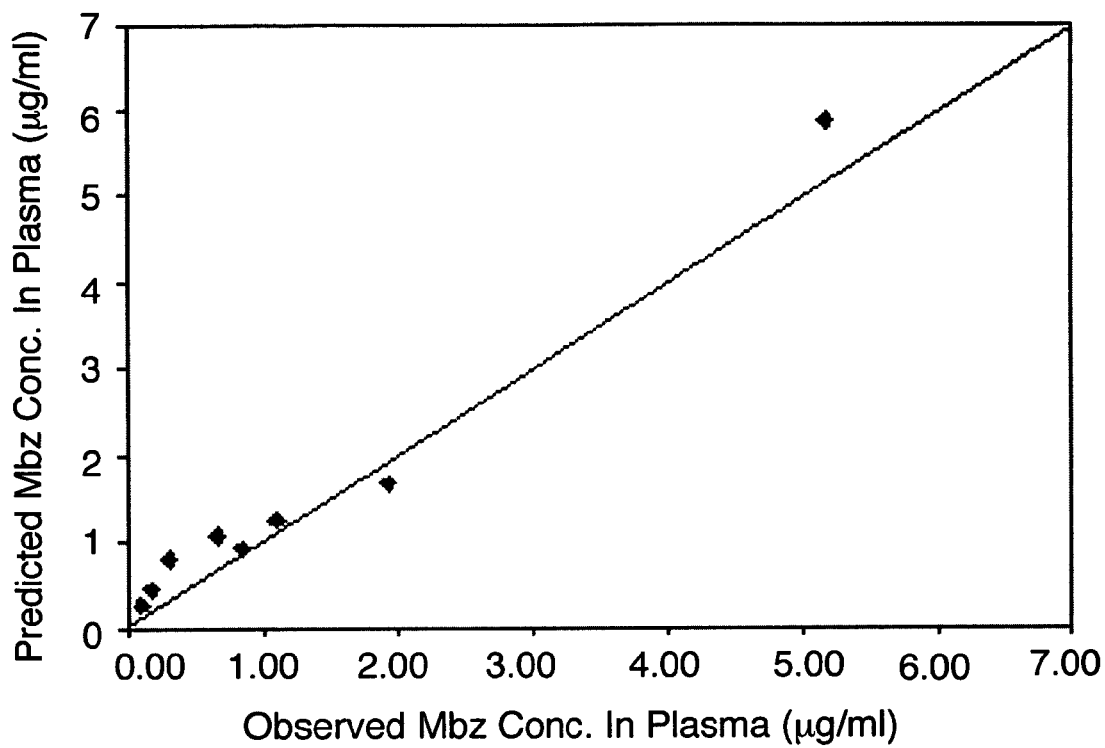
Figure 18D:
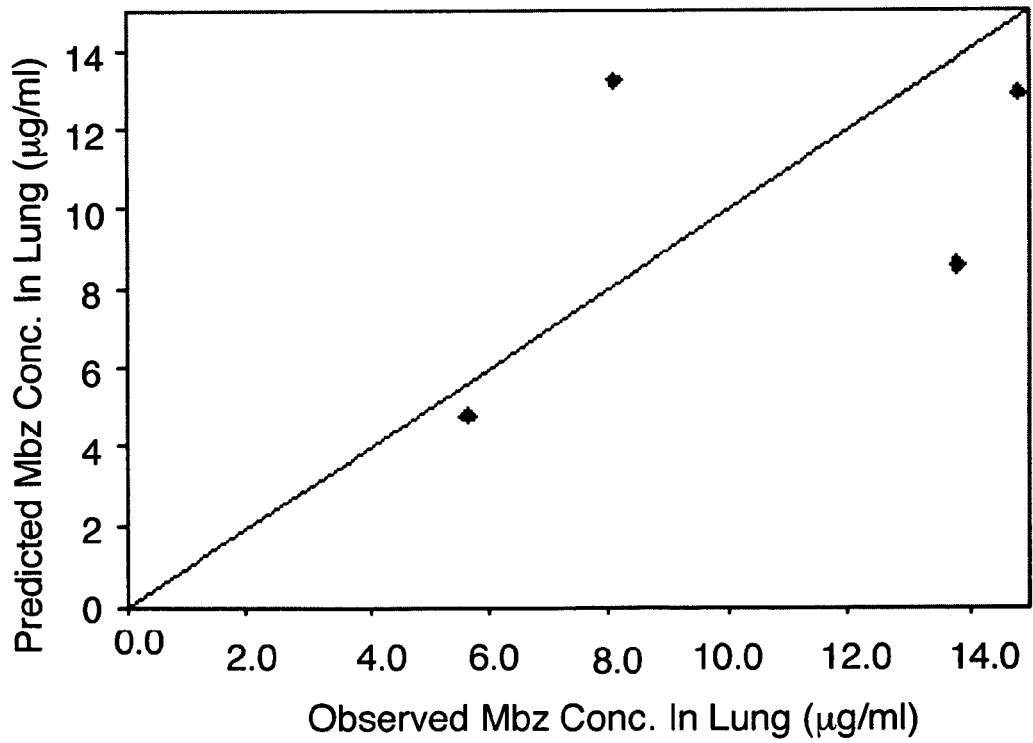
Figure 18E:
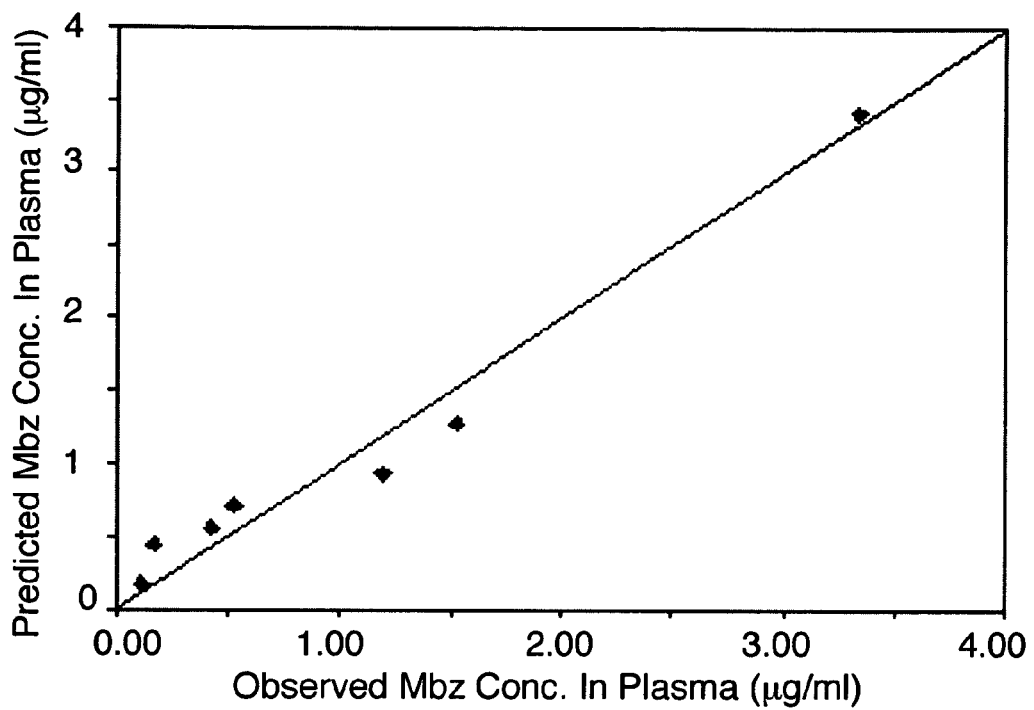
Figure 18F:
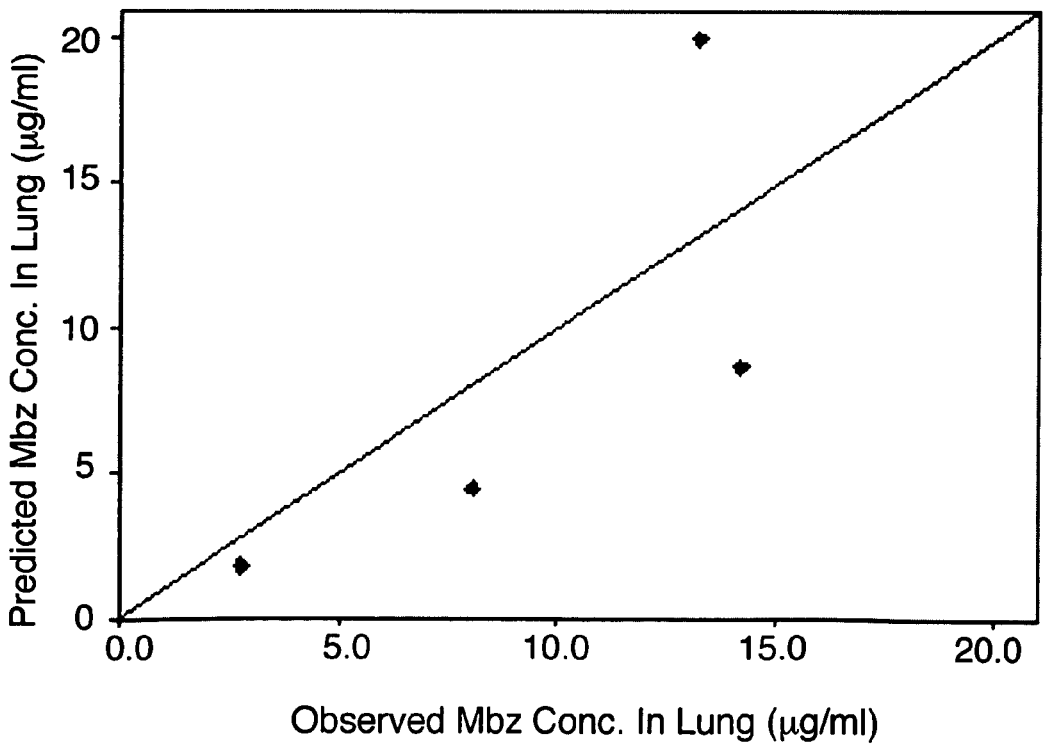
Figure 19A:
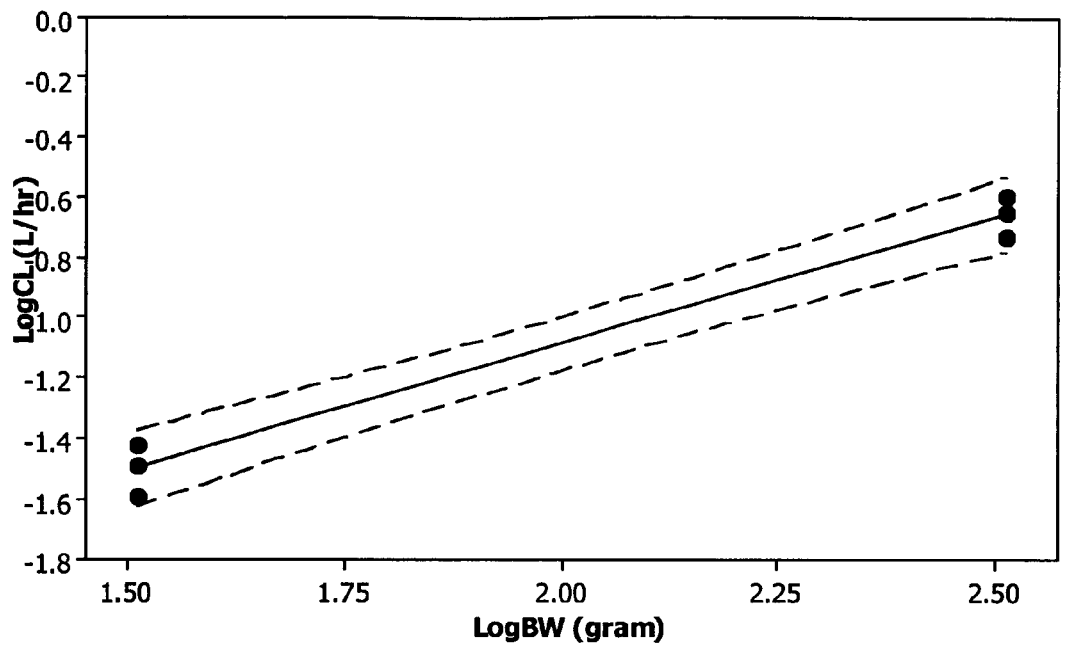
FIGS. 19A-19F. Allometric relationships between Mbz clearance (FIGS. 19A-19C) and Mbz Vss (FIGS. 19D-19F) and body weight (log-log) for cosolvent (FIGS. 19A, 19D), PM1 (FIGS. 19B, 19E) and PM2 (FIGS. 19C, 19F).
Figure 19B:
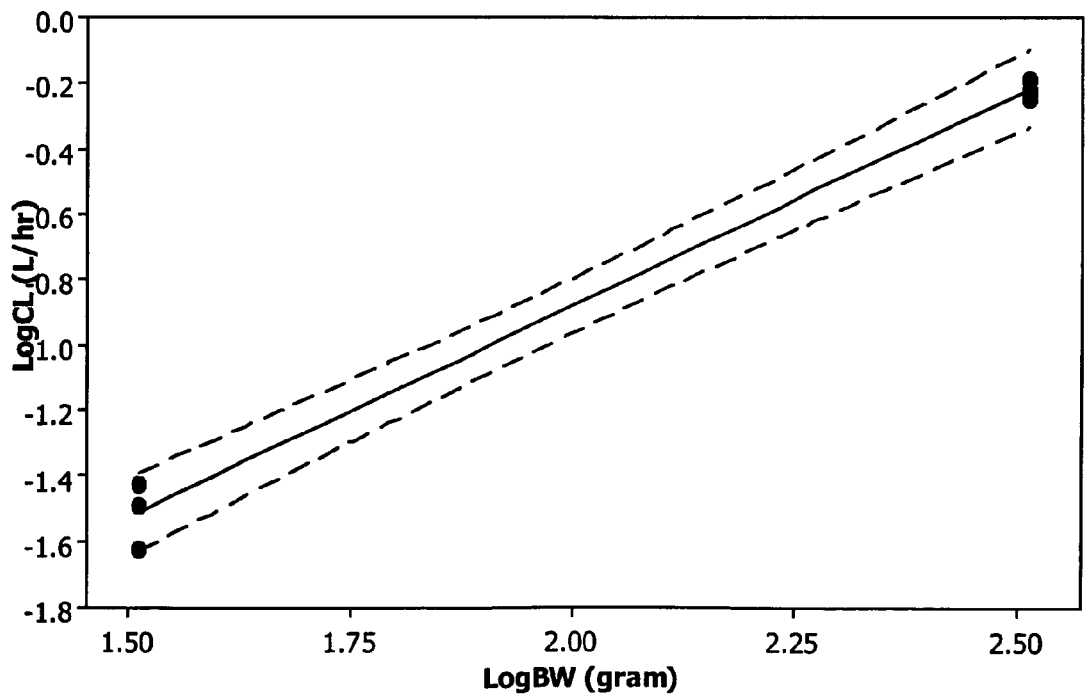
Figure 19C:
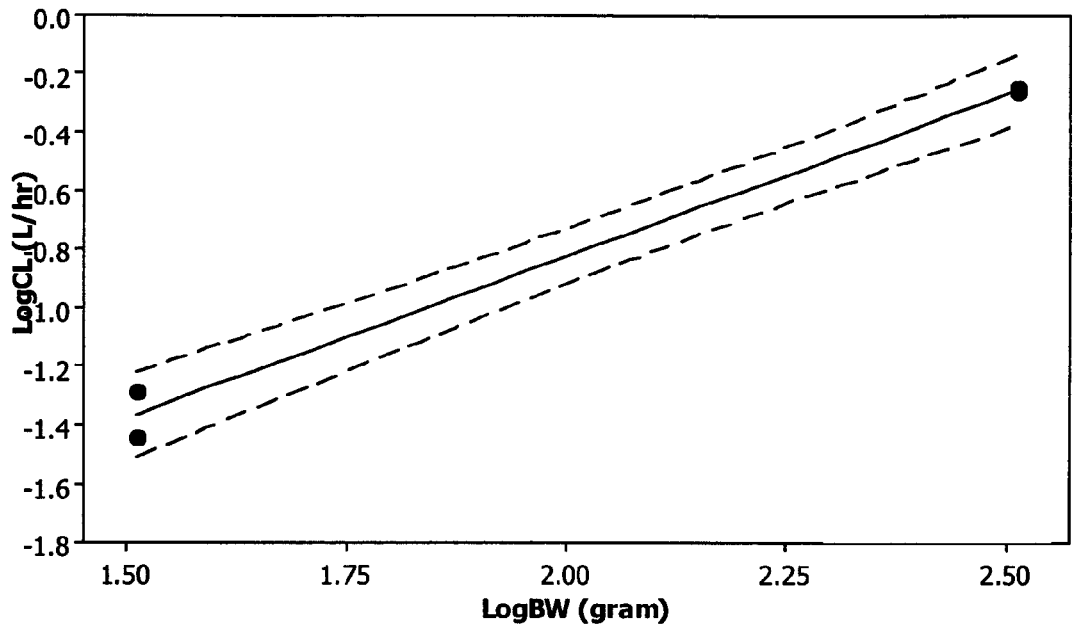
Figure 19D:
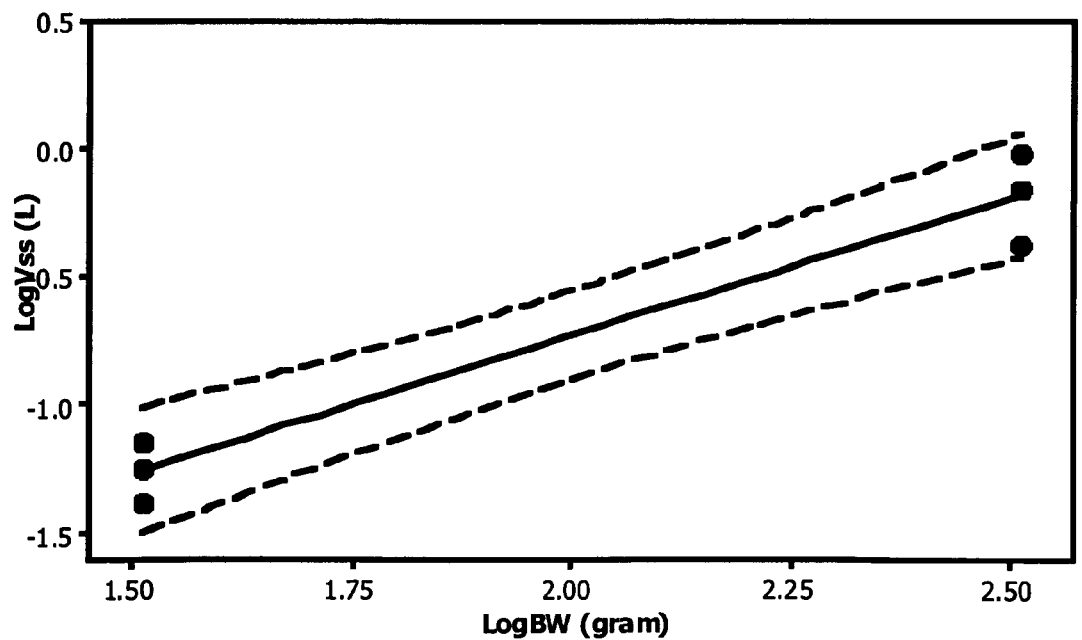
Figure 19E:
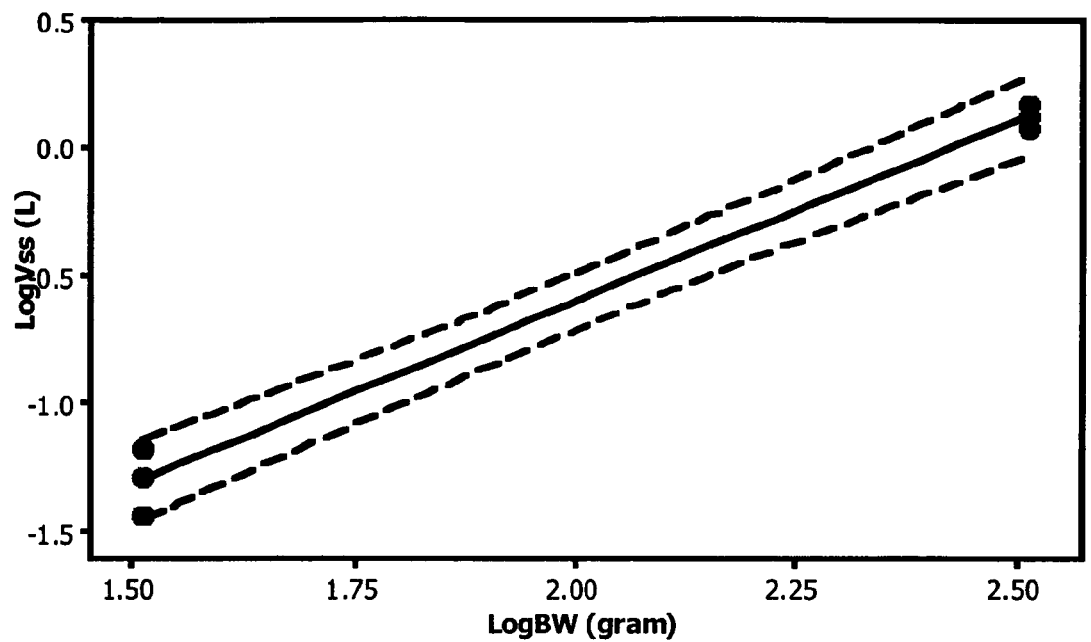
Figure 19F:
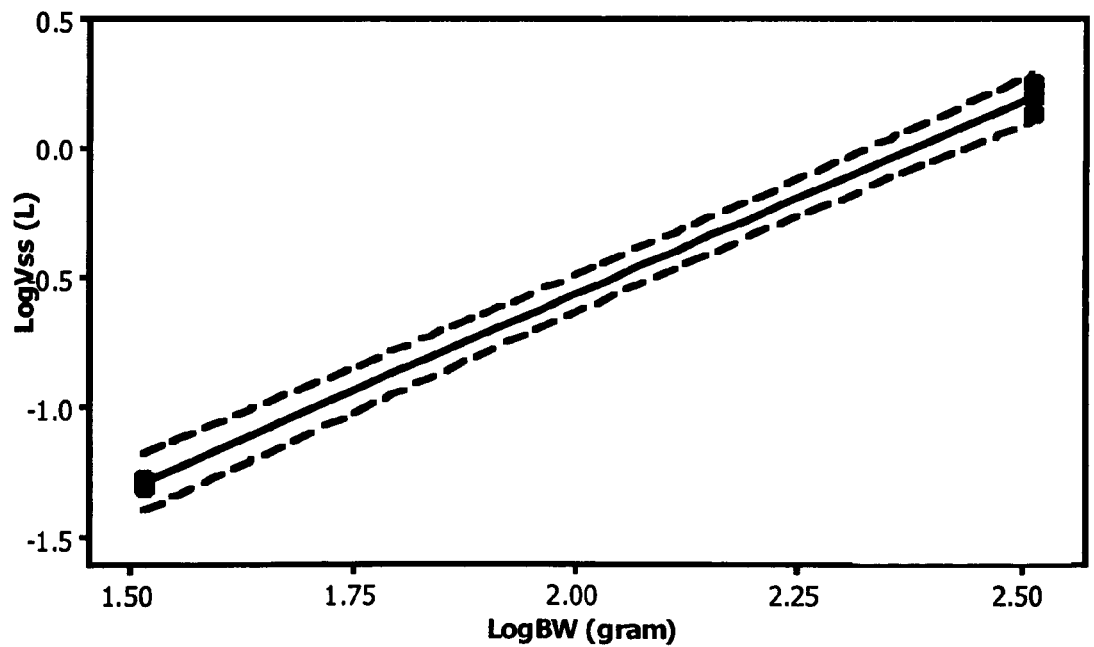
Figure 20A:
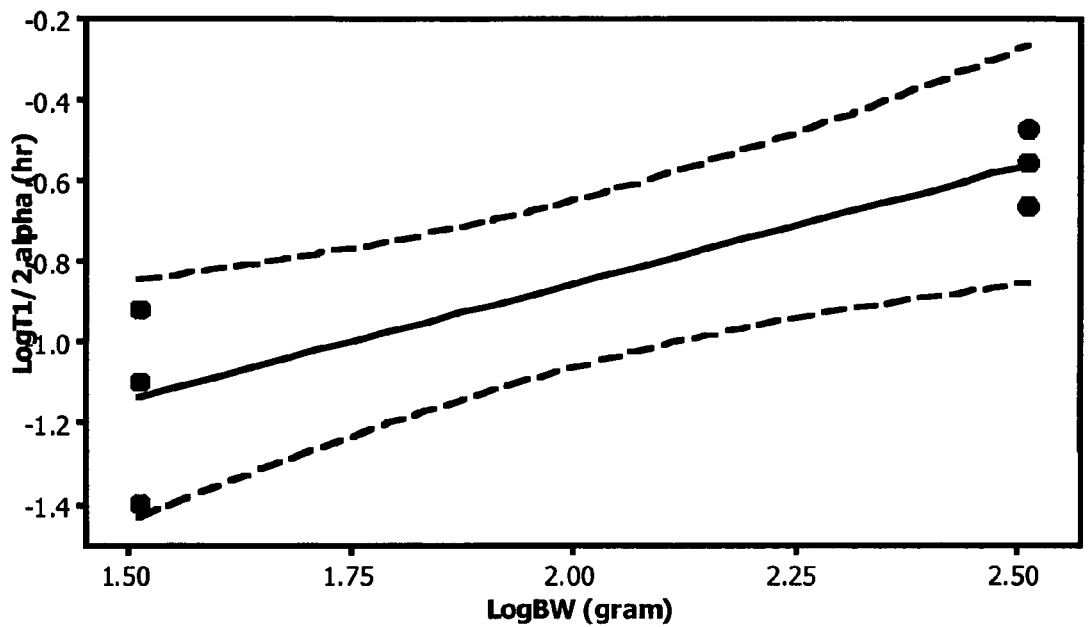
FIGS. 20A-20F. Allometric relationships between Mbz $t_{1/2,\ alpha}$ (FIGS. 20A-20C) and Mbz $t_{1/2,\ beta}$ (FIGS. 20D-20F) and body weight (log-log) for cosolvent (FIGS. 20A, 20D), PM1 (FIGS. 20B, 20E) and PM2 (FIGS. 20C, 20F).
Figure 20B:
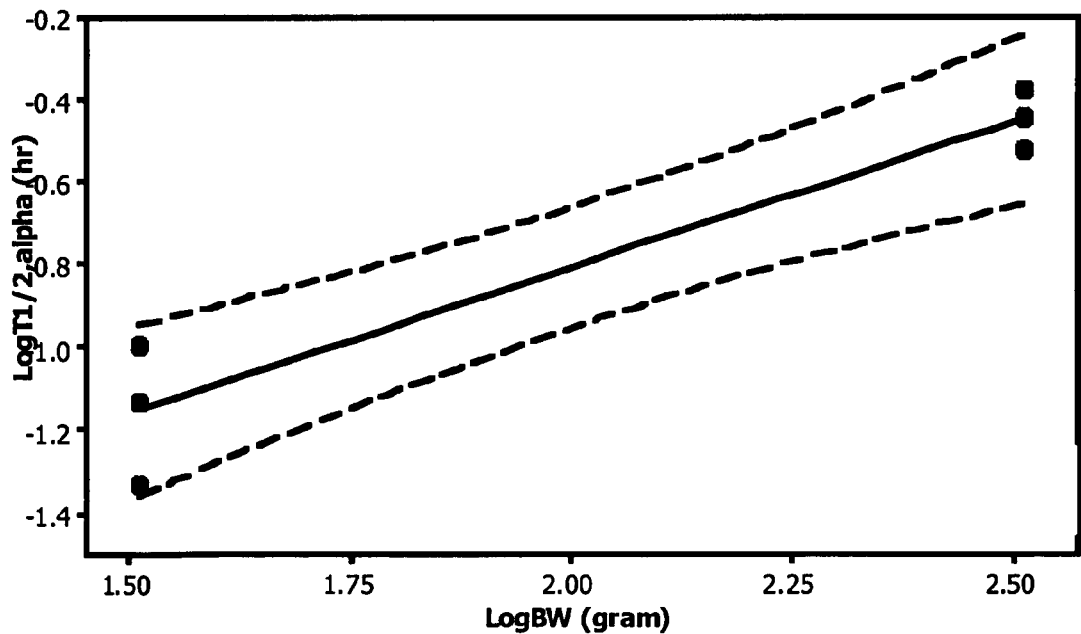
Figure 20C:
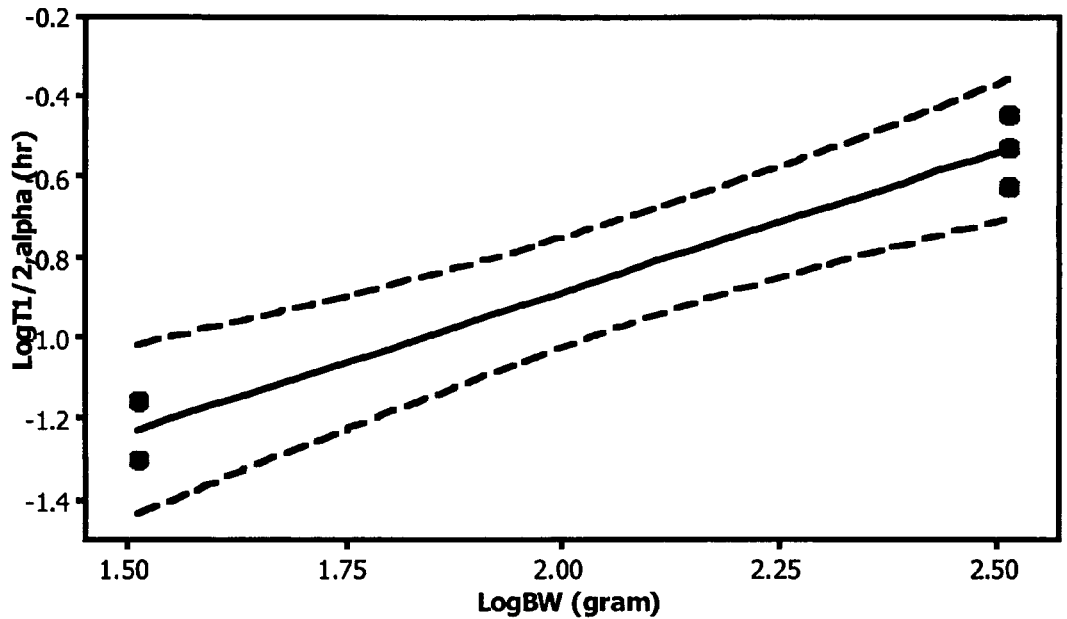
Figure 20D:
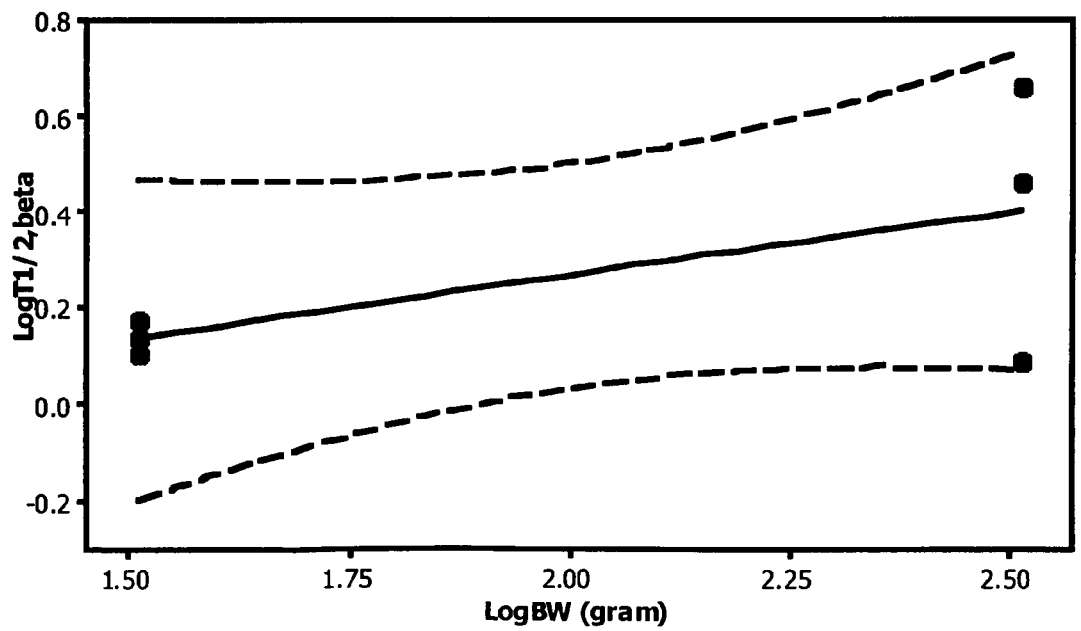
Figure 20E:
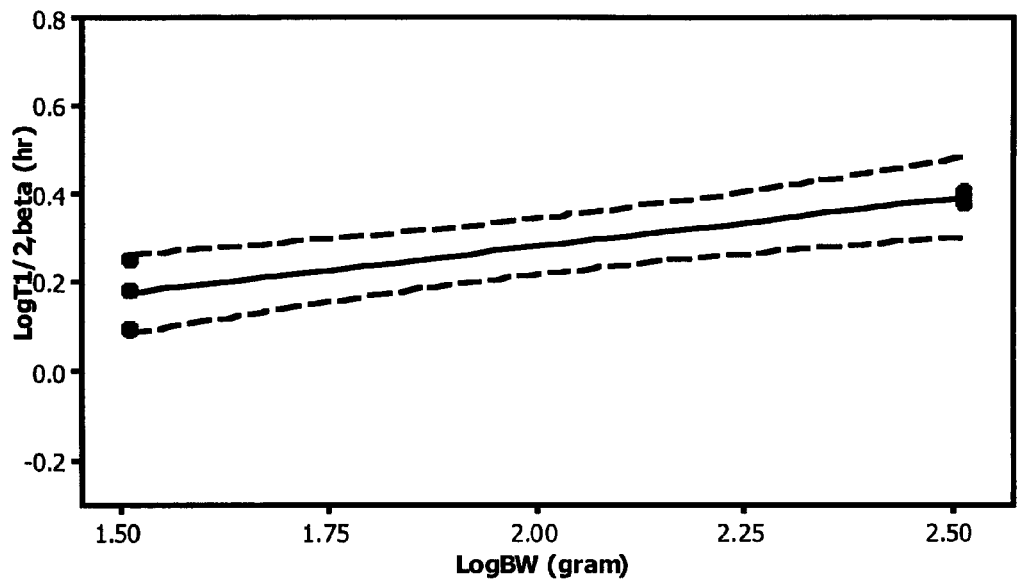
Figure 20F:
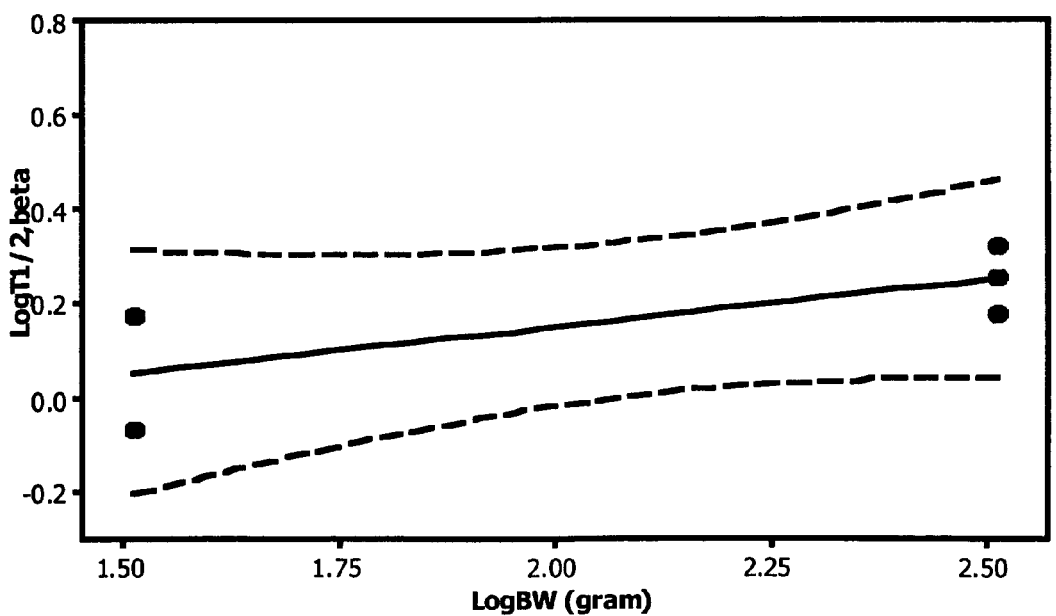

A set of Mbz concentrations in plasma and lung, respectively was used for validating the identified three-compartment model. Table XVII provides the estimated pharmacokinetic parameters of Mbz from cosolvent, PM1 and PM2 for a three-compartment model. The 95% C.I. for cosolvent is unavailable and the AUC ratio is the same. The observed Mbz concentrations in plasma and lung vs. the predicted Mbz concentrations were plotted for cosolvent (FIGS. 18A-18B), PM1 (FIGS. 18C-18D) and PM2 (FIGS. 18E-18F), respectively. The scattered plot showed that the developed model could predict Mbz concentrations in lung for cosolvent, PM1 and PM2.

TABLE XVII

| Parameter | Estimated PK Parameter Values (95% Confidence Interval) | | |
|---|---|---|---|
| | Cosolvent | PM1 | PM2 |
| $k_{10}$ (hr$^{-1}$) | 1.10 | 2.88 | 3.28 |
| | | (−9.39, 15.15) | (0.66, 5.90) |
| $k_{12}$ (hr$^{-1}$) | 1.55 | 2.99 | 3.03 |
| | | (1.48, 4.51) | (2.67, 3.38) |
| $k_{21}$ (hr$^{-1}$) | 5.00 | 1.82 | 5.87 |
| | | (−2.18, 5.83) | (3.02, 8.73) |
| $k_{13}$ (hr$^{-1}$) | 1.57 | 8.18 | 8.35 |

TABLE XVII-continued

| Parameter | Estimated PK Parameter Values (95% Confidence Interval) | | |
|---|---|---|---|
| | Cosolvent | PM1 | PM2 |
| $k_{31}$ (hr$^{-1}$) | 2.20 | (−30.18, 46.53) 1.41 | (−1.83, 18.52) 1.97 |
| $V_1$ (L) | 27.77 | (−2.59, 5.42) 6.74 | (1.09, 2.84) 9.12 |
| $AUC_{0-6\,hr,plasma}$/Dose (µg * hr/ml/mg/kg) | 1.08 | (−18.09, 31.57) 1.58 | (0.75, 17.49) 1.14 |
| $AUC_{0-6,lung}$/Dose (µg * hr/g/mg/kg) | 2.57 | 13.61 | 10.45 |
| AUC Ratio Lung/Plasma | 2.39 | 8.64 | 9.13 |

Prediction of Human Pharmacokinetic Parameters for Mbz from Cosolvent and Microemulsions (PM1 and PM2) by Allometric Scaling The allometric relationships between Mbz pharmacokinetic parameters (CL, $V_{ss}$, $t_{1/2}$, and $t_{1/2}$) (Table XVII) and body weight for cosolvent, PM1 and PM2 were plotted on a log-log scale (FIGS. 19A-19F and FIGS. 20A-20F). The 95% of confidence intervals (C.I.) of the regression slopes were displayed. All values are shown as mean±SD. Difference between any two means from one species were statistically evaluated using ANOVA, with Tukey's post-hoc analysis. The asterisk * denotes P<0.05 for comparison of pharmacokinetic parameters between cosolvent and microemulsions in rats.

TABLE XVIII

| | Formulations | | | | | |
|---|---|---|---|---|---|---|
| | Cosolvent | | PM1 | | PM2 | |
| | Animal | | | | | |
| | Mice (n = 3) | Rats (n-6) | Mice (n = 3) | Rats (n-3) | Mice (n = 3) | Rats (n-3) |
| CL (L/hr) | 0.032 ± 0.006 | 0.22 ± 0.036* | 0.032 ± 0.008 | 0.61 ± 0.04 | 0.044 (0.036, 0.052) | 0.56 ± 0.01 |
| Vss (L) | 0.057 ± 0.015 | 0.69 ± 0.27* | 0.052 ± 0.015 | 1.35 ± 0.15 | 0.052 (0.054, 0.050) | 1.58 ± 0.21 |
| $t_{1/2}$, α (hr) | 0.08 ± 0.04 | 0.28 ± 0.06 | 0.074 ± 0.027 | 0.30 ± 0.08 | 0.060 (0.070, 0.050) | 0.40 ± 0.01 |
| $t_{1/2}$, β (hr) | 1.37 ± 0.11 | 2.89 ± 1.67 | 1.51 ± 0.27 | 1.90 ± 0.45 | 1.17 (1.49, 0.86) | 2.43 ± 0.36 |

The pharmacokinetic parameters in humans predicted from the relationships estimated by inter-species scaling of Mbz from different microemulsion formulations and the 95% C.I. were also compiled in Table XIX. Compared the CL with 95% C.I. (0.09-0.97 L/hr) for cosolvent in humans, the CL for PM1 (3.05-28.50 L/hr) and PM2 (0.94-10.84 L/hr) were faster than that for cosolvent. The V in humans were (9.44-178.57, 95% C.I.) 41.14 L/kg and (26.00-175.75, 95% C.I.) 67.59 L/kg for PM1 and PM2, respectively, which were about 10-20 folds of that for cosolvent. In addition, although the alpha half-lives appeared to be similar among these three formulations, the beta half-lives appeared to be distinct between cosolvent and microemulsions (PM1 and PM2).

TABLE XIX

| Formulations | PK Parameters | CL (L/hr/kg) | Vss (L/kg) | t1/2, α (hr) | t1/2, β (hr) |
|---|---|---|---|---|---|
| Cosolvent | Predictions for Humans | 0.30 (0.09, 0.97) | 2.95 (0.04, 29.17) | 6.24 (0.4, 97.72) | 22.65 (0.47, 239.88) |
| | Allometric Relationships | $1.65 * 10^{-3} * BW^{0.84}$ | $1.36 * 10^{-3} * BW^{1.07}$ | $0.009 * BW^{0.58}$ | $0.54 * BW^{0.27}$ |
| PM1 | Predictions for Humans | 9.33 (3.05, 28.50) | 41.14 (9.44, 178.57) | 15.74 (2.26, 109.55) | 7.94 (3.42, 18.44) |
| | Allometric Relationships | $3.38 * 10^{-4} * BW^{1.29}$ | $.55 * 10^{-4} * BW^{1.43}$ | $0.006 * BW^{0.70}$ | $0.70 * BW^{0.22}$ |
| PM1 | Predictions for Humans | 3.20 (0.94, 10.84) | 67.59 (26.00, 175.75) | 12.74 (2.24, 72.71) | 5.20 (0.61, 44.29) |
| | Allometric Relationships | $9.01 * 10^{-4} * BW^{1.11}$ | $2.98 * 10^{-4} * BW^{1.48}$ | $0.005 * BW^{0.70}$ | $0.56 * BW^{0.20}$ |

The following references are cited herein.

Brugmans et al. JAMA, 217:313-316, 1971.

Chow and Gupta, Final Technical Report Phase 1: Effects of Particle Size on Pharmacokinetic Properties of Nano-Formulations, Pfizer Global Research & Development, Groton, Conn., Jul. 31, 2006.

Davis and Rowley, In Processing of Bone Marrow for Transplantation, McCarthey et al. (Eds), American Assoc. Blood Banks, Calif., 41-62, 1990.

Friedman and Platzer, Biochim. Biophys. Acta, 544(3):605-614, 1978.

Friedman and Platzer, Biochim. Biophys. Acta, 630(2):271-278, 1980

Gorin, Clin. Haematol., 15:19-48, 1986.

Gorin, In: Bone Marrow and Stem Cell Processing: A Manual of Current Techniques, Areman et al. (Eds. O, F.A. Davis Co., PA, 292-362, 1992.

Gottschall et al., Endocrinology, 127(1):272-277, 1990.

Gupta, P., Ph.D. Dissertation: Oral Bioavailability Enhancement of Mebendazole from Self-Nanoemulsifying Drug Delivery System (SNEDDS) and Self-Emulsifying Drug Delivery System (SEDDS), and Particle Size Effects on Mebendazole Disposition from Parenteral Formulations, University of Houston, June 2006.

Gupta et al., Abstract: Oral Microemulsion Formulation for Mebendazole, A Novel Anticancer Agent. In: The 18th National Meeting, American Association of Pharmaceutical Scientists (AAPS), Baltimore, Md., Nov. 10, 2004.

Gupta et al., Abstract: Self-Nanoemulsifying Drug Delivery System (SNEDDS) for Improved Oral Bioavailability of Mebendazole. In: The 32$^{nd}$ Annual Meeting and Exposition of the Controlled Release Society (CRS), Jun. 21-22, 2005.

Gupta et al., Abstract: comparative bioavailability studies of Oral Self-Nanoemulsifying Formulation Versus Intravenous Co-Solvent and Microemulsion Formulations of Antineoplastic Mebendazole. In: The 19th Annual Meeting, AAPS, Nashville, Tenn., Nov. 9, 2005.

Gupta et al., Abstract: Self-Emulsifying (SEDDS) and Self-Nanoemulsifying Drug Delivery Systems (SNEDDS) for Improved Oral Bioavailability of Mebendazole: Effects of Particle Size and Lipid Digestion. In: The 33$^{rd}$ Annual Meeting and Exposition of the CRS, Vienna, Austria, Jul. 22-26, 2006.

Keating et al. Leukemia and Lymphoma, 10: 153-157, 1993.

Keystone and Murdoch, Ann. Intern. Med., 91:582-586, 1979.

Kim, Drug. Metab. Rev., 19:345-368, 1988.

Kohler and Bachmann, Mol. Biochem. Parasitol., 4(506): 325-336, 1981.

Lacey and Watson, Biochem. Pharmacol., 34(7):1073-1077, 1985.

Lacey, Int. J. Parasitol, 18(7):885-936, 1988.

Liang et al., www.aapspharmsci.org. 2002.

Lockard et al. Epilepsia, 2077-2084, 1979.

McGann, Cryobiology, 15:3820-390, 1978.

Michiels et al., Arch. Int. Pharmacodyn Ther., 256(2):180-191, 1982.

Mukhopadhyay et al., Clin. Cancer Res., 8(9):2963-2969, 2002.

Russell et al., Biochem Pharmacol., 43(5): 1095-1100, 1992.

Sasaki et al., Mol. Cancer. Ther., 1(13):1201-1209, 2002.

Spiegel and Noseworthy, J. Pharm. Sci., 52:917-927, 1963.

U.S. Department of Health and Human Services: NCI Investigational Drugs, N.H. Pub. No. 94-2141, 1984.

Van den Bossche et al., Chemother., 19:67-128, 1982.

Van den Bossche, Ann. Soc. Belg. Med. Trop., 61:287-296, 1981.

Watts et al., Biochem. Pharmacol., 31:3035-3040, 1982.

Weiss et al., Cancer Chemother. Rep., 16:477-485, 1962.

Wilson et al., Am. J. Trop. Med. Hyg., 37:162-168, 1987.

Witassek et al., Eur. J. Clin. Pharmacol., 20:427-433, 1981.

Yalkowsky and Roseman, In: Techniques of Solubilization of Drugs, Yalkowsky (Ed.), Marcel Dekker Inc., NY, 91-134, 1981

Qi, Y., Ph.D. Dissertation: Impacts of Size on Pharmacokinetics and Biodistributions of Mebendazole Nanoformulations in Mice and Rats, University of Houston, May 2008.

Qi et al., Abstract: Comparative Pharmacokinetics and Biodistributions of Mebendazole from Cosolvent and Nanoemulsion Formulations in Nude Athymic Mice. In: The 98 Annual Meeting of American Association for Cancer Research (AACR), Los Angeles, Calif., Apr. 16, 2007.

Qi et al., Abstract: Comparative Inter-Species Scaling and Prediction of Human Pharmacokinetic Parameters of Antineoplastic Mebendazole from Nanoemulsions of Different Droplet Sizes. In: The 99$^{th}$ Annual Meeting of AACR, San Diego, Calif., Apr. 12-16, 2008.

Any patents or publications mentioned in this specification are indicative of the levels of those skilled in the art to which the invention pertains. Further, these patents and publications are incorporated by reference herein to the same extent as if each individual publication was specifically and individually incorporated by reference.

What is claimed is:

1. A drug delivery composition, comprising:
a) a benzimidazole derivative having the formula:

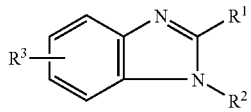

wherein $R^3$ is selected from the group consisting of H, carboxyl (—$CO_2H$), hydroxyl, amino, chloro, difluormethoxy, benzoyl, phenyl-thio, pyridinyl, propyl-thio, diphenyl, 5-methoxy, fluorophenylmethyl-2-chloro, propenyl, chloropropyl or esters (—$CO_2R^4$) wherein $R^4$ is selected from the group consisting of alkoxy, haloalkyl, alkenyl, and cycloalkyl, wherein the alkyl groups have from 1-8 carbons, or $CH_3CH_2(OCH_2CH_2)n$-, or $CH_3CH_2CH_2(OCH_2CH_2CH_2)n$-, or $(CH_3)_2CH(OCH(CH_3)CH_2)n$-, wherein n is from 1-3 wherein $R^1$ is OH, Cl, SH, carbamate or piperidin-4-yl, and $R^2$ is hydrogen, α-methylvinyl, 3-chloropropyl or piperidin-4-yl, or the pharmaceutically effective organic or inorganic salts thereof, or mixtures thereof;
b) an oil;
c) a surfactant;
d) a cosurfactant; and
e) a dipolar aprotic solvent, wherein said delivery composition forms as a parenterally-deliverable microemulsion having a droplet diameter of about 478 nm to less than 500 nm.

2. The drug delivery composition of claim 1, further comprising water.

3. The drug delivery composition of claim 2, wherein water to composition weight ratio is about 50%.

4. The drug delivery composition of claim 1, wherein the benzimidazole derivative is methyl 5-benzoylbenzimidazole-2-carbamate, methyl 5-(phenylthio)-2-carbamate,

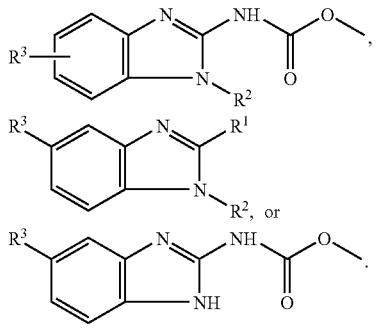

5. The drug delivery composition of claim 4, wherein the benzimidazole derivative is methyl 5-benzoylbenzimidazote-2-carbamate at a concentration of about 0.9 mg/ml to about 2 mg/ml.

6. The drug delivery composition of claim 1, wherein the oil is propylene glycol dicaprylate/dicaprate or triglycerides from coconut oil.

7. The drug delivery composition of claim 6, wherein the oil to composition has a weight ratio of about 14% to about 42%.

8. The drug delivery composition of claim 1, wherein the surfactant is polysorbate 80 and the cosurfactant is diethylene glycol monoethyl ether or C8/C10 mono-/diglyeride.

9. The drug delivery composition of claim 8, wherein the surfactant to composition and the cosurfactant to composition have individual weight ratios of about 6% to about 48 %.

10. The drug delivery composition of claim 9, wherein a ratio of surfactant:cosurfactant is about 1:0.5 to about 1:1.

11. The drug delivery composition of claim 1, wherein the dipolar aprotic solvent is dimethylsulfoxide.

12. The drug delivery composition of claim 11, wherein dimethylsulfoxide to composition has a weight ratio of about 5% to about 10%.

13. A drug delivery composition, comprising:
methyl 5-benzoylbenzimidazole-2-carbamate;
about 4% to about 42% by weight of an oil;
about 20% to about 41% by weight each of a surfactant and a cosurfactant in about a 1:0.75 to about 1:1 ratio of surfactant:cosurfactant; and
about 5% to about 10% by weight of dimethylsulfoxide, wherein said delivery composition forms a parenterally-deliverable microemulsion having a droplet diameter of about 478 nm to less than 500 nm.

14. The drug delivery composition of claim 13, comprising about 4% to about 9% by weight each of propylene glycol dicaprylate/dicaprate as the oil and about 20% to about 41% by weight of polysorbate 80 as the surfactant and either diethylene glycol monoethyl ether or C8/C10 mono-/diglyceride as the co-surfactant.

15. The drug delivery composition of claim 14, further comprising about 50% by weight of water.

16. The drug delivery composition of claim 13, comprising about 42% by weight of propylene glycol dicaprylate/dicaprate or C8/C10 triglycerides from coconut oil as the oil, about 27% by weight of polysorbate 80 combined with diethylene glycol monoethyl ether as the surfactant and about 21% of by weight of C8/C10 mono-/diglyceride as the co-surfactant.

17. The drug delivery composition of claim 13, wherein the methyl 5-benzoylbenzimidazole-2-carbamate is at a concentration of about 0.9mg/ml to about 2 mg/ml.

* * * * *